US010167341B2

(12) United States Patent
Cheung et al.

(10) Patent No.: US 10,167,341 B2
(45) Date of Patent: *Jan. 1, 2019

(54) HIGH AFFINITY ANTI-GD2 ANTIBODIES

(71) Applicant: Memorial Sloan-Kettering Cancer Center, New York, NY (US)

(72) Inventors: Nai-Kong V. Cheung, Purchase, NY (US); Mahiuddin Ahmed, New York, NY (US); Qi Zhao, Tseung Kwan (CN)

(73) Assignee: Memorial Sloan Kettering Cancer Center, New York, NY (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/776,298

(22) PCT Filed: Mar. 14, 2014

(86) PCT No.: PCT/US2014/029308
§ 371 (c)(1),
(2) Date: Sep. 14, 2015

(87) PCT Pub. No.: WO2014/144763
PCT Pub. Date: Sep. 18, 2014

(65) Prior Publication Data
US 2016/0032009 A1 Feb. 4, 2016

Related U.S. Application Data

(60) Provisional application No. 61/801,287, filed on Mar. 15, 2013.

(51) Int. Cl.
*C07K 16/00* (2006.01)
*C07K 16/30* (2006.01)
*A61K 51/10* (2006.01)
*A61K 47/68* (2017.01)

(52) U.S. Cl.
CPC ...... *C07K 16/3084* (2013.01); *A61K 47/6851* (2017.08); *A61K 51/1045* (2013.01); *C07K 2317/24* (2013.01); *C07K 2317/31* (2013.01); *C07K 2317/33* (2013.01); *C07K 2317/55* (2013.01); *C07K 2317/565* (2013.01); *C07K 2317/622* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. | |
| 6,180,370 B1 | 1/2001 | Queen et al. | |
| 6,884,879 B1 | 4/2005 | Baca et al. | |
| 7,423,114 B2 | 9/2008 | Gagnon et al. | |
| 9,315,585 B2 | 4/2016 | Cheung et al. | |
| 9,688,772 B2 | 6/2017 | Cheung et al. | |
| 9,802,995 B2 * | 10/2017 | Ahmed | C07K 16/468 |
| 2003/0003097 A1 | 1/2003 | Reff et al. | |
| 2003/0147808 A1 | 8/2003 | Cheung et al. | |
| 2003/0147881 A1 | 8/2003 | Cheung et al. | |
| 2003/0157108 A1 | 8/2003 | Presta | |
| 2004/0220084 A1 | 11/2004 | Sandhu | |
| 2004/0259771 A1 | 12/2004 | Stahl et al. | |
| 2005/0002930 A1 | 1/2005 | Johnson et al. | |
| 2005/0101770 A1 | 5/2005 | Presta | |
| 2009/0004674 A1 | 1/2009 | Sims et al. | |
| 2010/0150910 A1 | 6/2010 | Birkle et al. | |
| 2013/0216528 A1 | 8/2013 | Cheung et al. | |
| 2017/0253660 A1 | 9/2017 | Cheung et al. | |

FOREIGN PATENT DOCUMENTS

| | | |
|---|---|---|
| CN | 1726227 A | 1/2006 |
| EP | 0239400 A2 | 9/1987 |
| JP | 2002-532079 A | 10/2002 |
| JP | 2005-511706 A | 4/2005 |
| JP | 2007-537719 A | 12/2007 |
| JP | 2008-505174 A | 2/2008 |
| JP | 2009-506790 A | 2/2009 |
| RU | 2462476 C2 | 9/2012 |
| WO | WO-1991/09967 A1 | 7/1991 |
| WO | WO-1992/018629 A1 | 10/1992 |
| WO | WO-00/35483 A1 | 6/2000 |
| WO | WO-03/048321 A2 | 6/2003 |
| WO | WO-2005/070967 A2 | 8/2005 |
| WO | WO-2006/019447 A1 | 2/2006 |
| WO | WO-2007/030642 A2 | 3/2007 |
| WO | WO-2010/017598 A1 | 2/2010 |
| WO | WO-2011/160119 A2 | 12/2011 |

(Continued)

OTHER PUBLICATIONS

Mariuzza et al. (Annu. Rev. Biophys. Biophys. Chem., 16: 139-159, 1987).*
Gussow et al (Methods in Enzymology, 203: 99-121, 1991).*
Winkler et al (J. Imm., 265:4505-4514, 2000).*
MacCallum et al. (J. Mol. Biol. Oct. 11, 1996; 262 (5): 732-745).*
Arai, S. et al., Infusion of the allogeneic cell line NK-92 in patients with advanced renal cell cancer or melanoma: a phase I trial, Cytotherapy, 10(6):625-632 (2008).
Arbit, E. et al., Quantitative studies of monoclonal antibody targeting to disialoganglioside G d2 in human brain tumors, European Journal of Nuclear Medicine, 22(5):419-426 (1995).
Bargou, R. et al., Tumor regression in cancer patients by very low doses of a T cell-engaging antibody, Science, 321(5891):974-7 (2008).

(Continued)

*Primary Examiner* — Brad Duffy
(74) *Attorney, Agent, or Firm* — Choate, Hall & Stewart, LLP; Brenda Herschbach Jarrell; Tracy L. Vrablik

(57) ABSTRACT

In this application are described high affinity anti-GD2 antibody agents, and various methods and reagents related thereto, including for example for the detection, prevention, and/or therapeutical treatment of GD2-related diseases, in particular, neuroblastoma.

26 Claims, 3 Drawing Sheets
Specification includes a Sequence Listing.

(56) References Cited

FOREIGN PATENT DOCUMENTS

| WO | WO-2013/004842 A2 | 1/2013 |
|---|---|---|
| WO | WO-2014/144763 A2 | 9/2014 |

OTHER PUBLICATIONS

Barker, E. and Reisfeld, R.A., A mechanism for neutrophil-mediated lysis of human neuroblastoma cells, Cancer Research, 53(2):362-367 (1993).
Barker, E. et al., Effect of a chimeric anti-ganglioside GD2 antibody on cell-mediated lysis of human neuroblastoma cells, Cancer Research, 51(1):144-149 (1991).
Basu, E. et al., Phase I Study of Anti-GD2 Humanized 3F8 (hu3F8) Monoclonal Antibody (MAb) in Patients with Relapsed or Refractory Neuroblasoma (NB) or Other GD2-Positive Solid Tumors, Advances in Neuroblastoma Research, Information Book, 242 (2014).
Bergman, I. et al., Comparison of in vitro antibody-targeted cytotoxicity using mouse, rat and human effectors, Cancer Immunology, Immunotherapy, 49: 259-266 (2000).
Bindon, C.I. et al., Human Monoclonal IgG Isotypes Differ in Complement Activating Function at the Level of C4 as well as C1q, Journal of Experimental Medicine, 168:127-142 (1988).
Brandl, C. et al., The effect of dexamethasone on polyclonal T cell activation and redirected target cell lysis as induced by a CD19/CD3-bispecific single-chain antibody construct, Cancer Immunology, Immunotherapy, 56(10):1551-1563 (2007).
Brentjens, R.J. et al., Genetically targeted T cells eradicate systemic acute lymphoblastic leukemia zenografts, Clinical Cancer Research, 13(18):5426-5435 (2007).
Brischwein, K. et al., Strictly target cell-dependent activation of T cells by bispecific single-chain antibody constructs of the BiTE class, The Journal of Immunology, 30(8):798-807 (2007).
Brischwein, K., et al. MT110: a novel bispecific single-chain antibody construct with high efficacy in eradicating established tumors, Mol. Immunol., 43(8):1129-43 (2006).
Brooks, B.R. et al., CHARMM: The biomolecular simulation program, Journal of Computational Chemistry, 30(10)1 545-1614 (2009).
Casset, F. et al., A peptide mimetic of an anti-CD4 monoclonal antibody by rational design, Biochemical and Biophysical Research Communications, 307:198-205 (2003).
Chames, P. et al., Therapeutic antibodies: successes, limtations, and hopes for the future, British Journal of Pharmacology, 157(2):220-233 (2009).
Chang, H.R. et al., Expression of disialogangliosides GD2 and GD3 on human soft tissue sarcomas, Cancer, 70(3):633-638 (1992).
Chantada, G.L. et al., An aggressive bone marrow evaluation including immunocytology with GD2 for advanced retinoblastoma, Journal of Pediatric Hematology/Oncology, 28(6):369-373 (2006).
Chen, S. et al., CD59 expressed on a tumor cell surface modulates decay-accelerating factor expression and enhances tumor growth in a rat model of human neuroblastoma, Cancer Reserach, 60(11):3013-3018 (2000).
Chennamsetty, N. et al., Design of therapeutic proteins with enhanced stability, Proceedings of the Natural Academy of Sciences of the United States of America, 106(29):11937-11942 (2009).
Cheung, N.-K. V. et al., Monoclonal antibodies to a glycolipid antigen on human neuroblastoma cells, Cancer Research, 45(6):2642-2649 (1985).
Cheung, N.K. et al., Decay-accelerating factor protects human tumor cells from complement-mediated cytotoxicity in vitro, Journal of Clinical Investigation, 81(4):1122-1128 (1988).
Cheung, N.V. et al., Complete Tumor Ablation With Iodine 131-Radiolabeled Disialoganglioside GD2-Specific Monoclonal Antibody Against Human Neuroblastoma Xenografted in Nude Mice, JNCI 77(3):739-745 (1986).
Cheung, N.V. et al., Detection of Neuroblastoma Cells in Bone Marrow Using GD2 Specific Monoclonal Antibodies, Journal of Clinical Oncology 4(3): 363-369 (1986).
Cheung, N.V. et al., Disialoganglioside GD2 Anti-idiotypic monoclonal antibodies, Int. J. Cancer 54:499-505 (1993).
Cheung, N.V. et al., *FCGR2A* Polymorphism Is Correlated With Clinical Outcome After Immunotherapy of Neuroblastoma With Anti-GD2 Antibody and Granulocyte Macrophage Colony-Stimulating Factor, Journal of Clinical Oncology, 24(18): 2885-2890 (2006).
Cheung, N.V. et al., Ganglioside GD2 Specific Monoclonal Antigody 3F8: A Phase I Study in Patients With Neuroblastoma and Malignant Melanoma, Journal of Clinical Oncology, 5(9):1430-1440 (1987).
Cheung, N.V. et al., Humanizing murine IgG3 anti-GD2 antibody m3F8 substantially improves antibody-dependent cell-mediated cytotoxicity while retaining targeting in vivo, OncoImmunology, 1(4):477-489 (2012).
Cheung, N.V. et al., Single-Chain Fv-Streptavidin Substantially Improved Therapeutic Index in Multistep Targeting Directed at Disialoganglioside GD2, The Journal of Nuclear Medicine, 45:867-877 (2004).
Choi, B.S. et al., Phase I trial of combined treatment with ch14.18 and R24 monoclonal antibodies and interleukin-2 for patients with melanoma or sarcoma, Cancer Immunology, Immunotherapy, 55(7):761-774 (2006).
Coloma et al., Design and production of novel tetravalent bispecific antibodies, Nat. Biotechnol., 15:159-63 (1997).
Daldrup-Link, H.E. et al., In vivo tracking of genetically engineered, anti-HER2/neu directed natural killer cells to HER2/neu positive mammary tumors with magnetic resonance imaging, Eur. Radiol., 15(1): 26 pages (2005).
Dangl, J.L. et al., Segmental flexibility and complement fixation of genetically engineered chimeric human, rabbit and mouse antibodies, The EMBO Journal, 7(7):1989-1994 (1988).
Davies, D.M. and Maher, J., Adoptive T-cell immunotherapy of cancer using chimeric antigen receptor-grafted T cells, Arch. Immunol. Ther. Exp. (Warsz)., 58(3):165-78 (2010), Nov. 4, 2017.
De Pascalis, R. et al., Grafting of "Abbreviated" Complementarity-Determining Regions Containing Specificity-Determining Residues Essential for Ligand Contact to Engineer a Less Immunogenic Humanized Monoclonal Antibody, The Journal of Immunology, 169:3076-3084 (2002).
Dillman, S.L. et al., Activation of Human Complement by Totally Human Monoclonal Antibodies, Molecular Immunology, 32(13):957-964 (1995).
Drier, T. et al., Extremely potent, rapid and costimulation-independent cytotoxic T-cell response against lymphoma cells catalyzed by a single-chain bispecific antibody, International Journal of Cancer, 100(6):690-697 (2002).
Eshhar, Z. et al., Specific activation and targeting of cytotoxic lymphocytes through chimeric single chains consisting of antibody-binding domains and the γ or zeta subunits of the immunoglobulin and T-cell receptors, Proc. Natl. Acad. Sci. USA, 90:720-724 (1993).
Extended European Search Report for EP 11796578.0, 9 pages (Nov. 15, 2013).
Finney, H.M. et al., Activation of resting human primary T cells with chimeric receptors: costimulation from CD28, inducible costimulatory, CD134, and CD137 in series with signals from the TCR zeta chain, The Journal of Immunology, 172(1):104-113 (2004).
Fitzgerald, K. et al., Improved tumour targeting by disulphide stabilized diabodies expressed in Pichia pastoris, Protein Eng., 10(10):1221-5 (1997).
Furukawa, K. et al., GD2 ganglioside on human T-lymphotropic virus type I-infected T cells: possible activation of beta-1,4-N-acetylgalactosaminyltransferase gene by p40tax, Proceedings of the Natural Academy of Sciences of the United States of America, 90(5):1972-1976 (1993).
Gillies, S.M. et al., High-level expression of chimeric antibodies using adapted cDNA variable region cassettes, Journal of Immunological Methods, 125(1-2):191-202 (1989).
Gilman, A.L. et al., Phase I study of ch14.18 with granulocyte-macrophage colony-stimulating factor and interleukin-2 in children with neuroblastoma after autologous bone marrow transplantation or stem-cell rescue: a report from the Children's Oncology Group, Journal of Clinical Oncology, 27(1):85-91 (2009).

(56) References Cited

OTHER PUBLICATIONS

Gong, M.C. et al., Cancer Patient T Cells Genetically Targeted to Prostate-Specific Membrane Antigen Specifically Lyse Prostate Cancer Cells and Release Cytokines in Response to Prostate-Specific Membrane Antigen, Neoplasia,1(2):123-127 (1999).
Grabert, R.C. et al., Human T cells armed with Her2/neu bispecific antibodies divide, are cytotoxic, and secrete cytokines with repeated stimulation, Clinical Cancer Research, 12(2):569-576 (2006).
Grant, S.C. et al., Targeting of small-cell lung cancer using the anti-GD2 ganglioside monoclonal antibody 3F8: a pilot trial, European Journal of Nuclear Medicine and Molecular Imaging, 23(2):145-149 (1996).
Haynes, N.M. et al., Rejection of syngeneic colon carcinoma by CTLs expressing single-chain antibody receptors codelivering CD28 costimulation, The Journal of Immunology, 169(10):5780-5786 (2002).
Haynes, N.M. et al., Single-chain antigen recognition receptors that costimulate potent rejection of established experimental tumors, Blood, 100(9): 3155-3163 (2002).
Heiner, J.P. et al., Localization of GD2-specific monoclonal antibody 3F8 in human osteosarcoma, Cancer Research, 47(20):5377-5381 (1987).
Helene, M. et al., Inhibition of graft-versus-host disease. Use of a T cell-controlled suicide gene, J. Immunol., 158(11):5079-82 (1997).
Imai, C. and Campana, D., Genetic modification of T cells for cancer therapy, J. Biol. Regul. Homeost. Agents., 18(1):62-71 (2004).
Imai, C. et al., Chimeric receptors with 4-1BB signaling capacity provoke potent cytotoxicity against acute lymphoblastic leukemia, Leukemia. 16(4):676-84 (2004).
International Preliminary Report on Patentability for PCT/US2011/041082, 8 pages (Mar. 21, 2012).
International Search Report for PCT/US2011/041082, 5 pages (Mar. 21, 2012).
International Search Report for PCT/US2014/029308, 6 pages (Oct. 7, 2014).
Irving, B.A. and Weiss, A., The cytoplasmic domain of the T cell receptor zeta chain is sufficient to couple to receptor-associated signal transduction pathways, Cell, 64(5):891-901 (1991).
Jones, P.T. et al., Replacing the complementarity-determining regions in a human antibody with those from a mouse, Nature, 321(6069): 522-525 (1986).
Jurcic, J. et al., Monoclonal antibody therapy of cancer, Cancer Chemotherapy and Biological Response Modifiers Modifiers Annual 17, 10:195-216 (1997).
Khaw, B.A. et al., Technetium-99m labeling of antibodies to cardiac myosin Fab and to human fibrinogen, J. Nucl. Med., 23(11):1011-9 (1982).
Kiewe, P. et al., Phase I trial of the trifunctional anti-HER2 x anti-CD3 antibody ertumaxomab in metastatic breast cancer, Clinical Cancer Research, 12(10):3085-3091 (2006).
Koehne, G. et al., Quantitation, selection, and functional characterization of Epstein-Barr virus specific and alloreactive T cells detected by intracellular interferon-gamma production and growth of cytotoxic precursors, Blood, 99(5):1730-1740 (2002).
Korbelik. M. and Sun, J., Cancer treatment by photodynamic therapy combined with adoptive immunotherapy using genetically altered natural killer cell line, International Journal of Cancer, 93(2):269-274 (2001).
Kowolik, C.M. et al., CD28 Costimulation Provided through a CD19-Specific Chimeric Antigen Receptor Enhances In vivo Persistence and Antitumor Efficacy of Adoptively Transferred T Cells, Cancer Research, 66(22):10995-11004 (2006).
Kramer, K. et al., Phase I study of targeted radioimmunotherapy for leptomeningeal cancers using intra-Ommaya 131-I-3F8, Journal of Clinical Oncology, 24(34):5465-5470 (2007).
Krause, A. et al., Antigen-dependent CD28 Signaling Selectivity Enhances Survival and Proliferation in Genetically Modified Activated Human Primary T Lymphocytes, The Journal of Experimental Medicine, 188(4):619-626 (1998).

Kruschinski, A. et al., Engineering antigen-specific primary human NK cells against HER-2 positive carcinomas, PNAS, 105(45):17481-17486 (2008).
Kushner, B. H. et al., Anti-GD2 monoclonal antibody 3F8 plus granulocytemacrophage colony-stimulating factor (GM-CSF) for primary refractory neuroblastoma (NB) in bone marrow (BM), Journal of Clinical Oncology, ASCO Annual Meeting Proceedings, vol. 25, No. 18S: 9502 (2007).
Kushner, B. H. et al., High-dose cyclophosphamide inhibition of humoral immune response to murine monoclonal antibody 3F8 in neuroblastoma patients: broad implications for immunotherapy, Pediatr Blood Cancer, 48(4):430-4 (2007).
Kushner, B.H. and Cheung, N.K., Absolute requirement of CD11/CD18 adhesion molecules, FcRII and the phosphatidylinositol-linked FcRIII for monoclonal antibody-mediated neurotrophil anti-human tumor cytotoxicity, Blood, 79(6):1484-1490 (1992).
Kushner, B.H. et al., Hyperfractionated low-dose radiotheraphy for high-risk neuroblastoma after intensive chemotherpahy and surgery, Journal of Clinical Oncology 19(11):2821-2828 (2001).
Kushner, B.H. et al., Phase II Trial of the Anti-GD2 Monoclonal Antibody 3F8 and Granulocyte-Macrophage Colony-Stimulating Factor for Neuroblastoma, Journal of Clinical Oncology 19(22):4189-4194 (2001).
Kushner, B.H. et al., Successful Multifold Dose Escalation of Anti-GD2 Monoclonal Antibody 3F8 in Patients With Neuroblastoma: A Phase I Study, Journal of Clinical Oncology, 29(9):1168-1174 (2011).
Lamzin, V.S. and Wilson, K.S., Automated refinement of protein models, Acta Crystallographica Section D Biological Crystallography, 49(Pt 1):129-147 (1993).
Lazar, G.A. et al., Engineered antibody Fc variants with enhanced effector function, PNAS USA, 103(11): 4005-4010 (2006).
Longee, D.C. et al., Disialoganglioside GD2 in human neuroextodermal tumor cell lines and gliomas, Acta Neuropathologica, 82(1):45-54 (1991).
Loskog, A. et al., Addition of the CD28 signaling domain to chimeric T-cell receptors enhances chimeric T-cell resistance to T regulatory cells, Leukemia, 20(10):1819-28 (2006).
Lutterbuese, R. et al., Potent control of tumor growth by CEA/CD3-bispecific single-chain antibody constructs that are not competitively inhibited by soluble CEA, The Journal of Immunology, 32(4):341-352 (2009).
Mack, M. et al., A small bispecific antibody construct expressed as a functional single-chain molecule with high tumor cell cytotoxicity, Proc. Natl. Acad. Sci. U S A, 92(15):7021-5 (1995).
Mackall, C. L. et al., T-Cell Immunodeficiency Following Cytotoxic Antineoplastic Therapy: A Review, Stem Cells, 18: 10-18 (2000).
Mackall, C.L. et al., Prolonged CD4 depletion after sequential autologous peripheral blood progenitor cell infusions in children and young adults, Blood, 96(2):754-762 (2000).
Maher, J. et al., Human T-lymphocyte cytotoxicity and proliferation directed by a single chimeric TCRzeta/CD28 receptor, Nat. Biotechnol., 20(1):70-5 (2002).
McCoy, A.J. et al., Phaser crystallographic software, Journal of Applied Crystallography, 40(Pt.4):658-674 (2007).
Metelitsa, L.S. et al., Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis, Blood, 99(11):4166-4173 (2002).
Modak, S. and Cheung, N.V., Disialoganglioside Directed Immunotherapy of Neuroblastoma, Cancer Investigation 25:67-77 (2007).
Modak, S. et al., Monoclonal Antibody 8H9 Targets a Novel Cell Surface Antigen Expressed by a Wide Spectrum of Human Solid Tumors, Cancer Research, 61: 4048-4054 (2001).
Moeller, M. et al., A functional role for CD28 costimulation in tumor recognition by single-chain receptor-modified T cells, Cancer Gene Ther., 11(5):371-9 (2004).

(56) References Cited

OTHER PUBLICATIONS

Mueller, B.M. et al., Serum half-life and tumor localization of chimeric antibody deleted of the CH2 domain and directed against the disialoganglioside GD2, Proceedings of the National Academy of Sciences of the United States of America, 87(15):5702-5705 (1990).
Mujoo, K. et al., Functional properties and effect on growth suppression of human neuroblastoma tumors by isotype switch variants of monoclonal antiganglioside GD2 antibody 14.18, Cancer Research, 49(11):2857-2861 (1989).
Murshudov, G.N. et al., Refinement of macromolecular structures by the maximum-likelihood method, Acta Crystallographica Section D Biological Crystallography, 53(Pt 3):240-255 (1997).
Navid, F. et al., Anti-GD2 Antibody Therapy for GD2-expressing Tumors, Current Cancer Drug Targets, 10(2): 200-209 (2010).
Nguyen, P. and Geiger, T.L., Antigen-specific targeting of CD8+ T cells with receptor-modified T lymphocytes, Gene Ther., 10(7):594-604 (2003).
O'Reilly, R.K. et al., Adoptive transfer of unselected or leukemia-reactive T-cells in the treatment of relapse following allogeneic hematopoietic cell transplantation, Seminars in Immunology, 22(3):162-172 (2010).
Offner, S. et al., Induction of regular cytolytic T cell synapses by bispecific single-chain antibody constructs on MHC class I-negative tumor cells, Molecular Immunology, 43(6):763-771 (2006).
Orcutt, K.D. et al., A modular IgG-scFv bispecific antibody topology, Protein Eng. Des. Sel., 23(4):221-8 (2010).
Orlandi, R. et al., Cloning immunoglobulin variable domains for expression by the polymerase chain reaction, Proceedings of the Natural Academy of Sciences of the United States of America, 86(10):3833-3837 (1989).
Papapetrou, E.P. et al., Harnessing endogenous miR-181a to segregate transgenic antigen receptor expression in developing versus post-thymic T cells in murine hematopoietic chimeras, The Journal of Clinical Investigation, 119(1):157-168 (2009).
Patel, K. et al., Monoclonal antibody 3F8 recognises the neural cell adhesion molecule (NCAM) in addition to ganglioside GD2, Br. J. Cancer, 60: 861-866 (1989).
Paul, W.E., Fundamental Immunology, 3rd Edition, 292-295 (1993).
Pegram, H.J. et al., Adoptive transfer of gene-modified primary NK cells can specifically inhibit tumor progression in vivo, the Journal of Immunology, 181(5):3449-3455 (2008).
Prados, J. et al., Induction of drug resistance in embryonal rhabdomyosarcoma treated with conventional chemotherapy is associated with HLA class I increase, Neoplasma, 53(3):226-231 (2006).
Pulè M.A. et al., A chimeric T cell antigen receptor that augments cytokine release and supports clonal expansion of primary human T cells, Mol. Ther., 12(5):933-41 (2005).
Queen, C. et al., A humanized antibody that binds to the interleukin 2 receptor, Proceedings of the Natural Academy of Sciences of the United States of America, 86(24):10029-10033 (1989).
Raffaghello, L. et al., Multiple defects of the antigen-processing machinery components in human neuroblastoma immunotherapeutic implications, Oncogene, 24(29):4634-4644 (2005).
Riechmann, L. et al., Reshaping human antibodies for therapy, Nature, 332(6162): 323-327 (1988).
Roberts, M.R. et al., Antigen-specific cytolysis by neutrophils and NK cells expressing chimeric immune receptors bearing zeta or gamma signaling domains, The Journal of Immunology, 161(1):375-384 (1998).
Romeo, C. et al., Sequence requirements for induction of cytolysis by the T cell antigen/Fc receptor zeta chain, Cell, 68(5):889-97 (1992).
Rossig, C. and Brenner, M.K., Genetic modification of T lymphocytes for adoptive immunotherapy, Mol. Ther., 10(1):5-18 (2004).
Rossig, C. et al., Epstein-Barr virus-specific human T lymphocytes expressing antitumor chimeric T-cell receptors: potential for improved immunotherapy, Blood, 99(6):2009-2016 (2002).
Rossig, C. et al., Targeting of G(D2)-positive tumor cells by human T lymphocytes engineered to express chimeric T-cell receptor genes, Int. J. Cancer, 94(2):228-36 (2001).
Rudikoff, S. et al., Single amino acid substitution altering antigen-binding specificity, Proceedings of the National Academy of Science, 79:1979-1983 (1982).
Saarinen, U.M. et al., Eradiction of Neuroblastoma Cells in Vitro by Monoclonal Antibody and Human Complement: Method for Purging Autologous Bone Marrow, Cancer Research, 45: 5969-5975 (1985).
Sadelain, M. et al., The Basic Principles of Chimeric Antigen Receptor Design, Cancer Discovery, 3:388-398 (2013).
Saleh, M.N. et al., Phase I trial of the chimeric anti-GD2 monoclonal antibody ch14.18 in patients with malignant melanoma, Human Antibodies & Hybridomas, 3(1):19-24 (1992).
Seino, J. et al., Activation of human complement by mouse and mouse/human chimeric monoclonal antibodies, Clinical Experimental Immunology, 94:291-296 (1993).
Simon, T. et al., Consolidation treatment with chimeric anti-GD2-antibody ch14.18 in children older than 1 year with metastatic neuroblastoma, Journal of Clinical Oncology, 22(17):3549-3557 (2004).
Sondermann, P. et al., The 3.2-A crystal structure o fthe human IgG1 Fc fragment-Fc gammaRIII complex, Nature, 406:267-273 (2000).
Sorkin, L.S. et al., Anti-GD2 with an FC point mutation reduces complement fixation and decreases antibody-induced allodynia, PAIN, 149:135-142 (2010).
Tam, Y.K. et al., Immunotherapy of Malignant Melanoma in a SCID Mouse Model Using the Highly Cytotoxic Natural Killer Cell Line NK-92, Journal of Hematotherapy, 8:281-290 (1999).
Teng, M.W. et al., Immunotherapy of cancer using systemically delivered gene-modified human T lymphocytes, Hum. Gene Ther., 15(7):699-708 (2004).
Thakur, A. and Lum, L.G., Cancer therapy with bispecific antibodies: clinical experience, Current Opinion in Molecular Therapeutics, 12(3):340-349 (2010).
Topp et al., Blood (ASH Annual Meeting Abstracts) 114, 840 (2009).
Valim, Y.M and Lachmann, P.J., The effect of antibody isotype and antigenic epitope density on the complement-fixing activity of immune complexes: A systematic study using chimaeric anti-NIP antibodies with human Fc regions, Clinical Experimental Immunology, 84:1-8 (1991).
Vera, J. et al., T lymphocytes redirected against the κ light chain of human immunoglobulin efficiently kill mature B lymphocyte-derived malignant cells, Blood, 108(12):3890-3897 (2006).
Verhoeyen, M. et al., Reshaping human antibodies: grafting an antilysozyme activity, Science, 239(4847): 1534-1536 (1988).
Wang, G. et al., A T cell-independent anitutmor response in mice with bone marrow retrovirallytransduced with an antibody/Fc-γ chain chimeric receptor gene recognizing a human ovarian cancer antigen, Nature Medicine, 4(2): 168-172 (1998).
Wang, J. et al, Optimizing adoptive polyclonal T cell immunotherapy of lymphomas, using a chimeric T cell receptor possessing CD28 and CD137 costimulatory domains, Hum. Gene Ther., 18(8):712-25 (2007).
Weijtens, M.E. et al., Single chain Ig/gamma gene-redirected human T lymphocytes produce cytokines, specifically lyse tumor cells, and recycle lytic capacity, J. Immunol., 157(2):836-43 (1996).
Wilkie, S. et al., Retargeting of human T cells to tumor-associated MUC1: the evolution of a chimeric antigen receptor, The Journal of Immunology, 180(7):4901-4909 (2008).
Written Opinion for PCT/US2011/041082, 7 pages (dated Mar. 21, 2012).
Written Opinion for PCT/US2014/029308, 7 pages (dated Oct. 7, 2014).
Wölfl, M. et al., Expression of MHC class I, MHC class II, and cancer germline antigens in neuroblastoma, Cancer Immunology, Immunotherapy, 54(4):400-406 (2005).
Yu, A.L. et al., Anti-GD2 Antibody with GM-CSF, Interleukin-2, and Isotretinoin for Neuroblastoma, The New England Journal of Medicine, 363(14): 1324-1334 (2010).

(56) References Cited

OTHER PUBLICATIONS

Zakrzewski, J. L. et al., Adoptive transfer of T-cell precursors enhances T-cell reconstitution after allogeneic hematopoietic stem cell transplantation, Nature Medicine, 12(9):1039-1047 (2006).
Zakrzewski, J.L. et al., Tumor immunotherapy across MHC barriers using allogeneic Tcell precursors, Nat. Biotechnol., 26(4):453-461 (2008).
Zhang, S. et al., Selection of tumor antigens as targets for immune attack using immunohistochemistry: I. Focus on gangliosides, International Journal of Cancer, 73(1):42-49 (1997).
Zhao, Q. et al., Human monoclonal antibody fragments binding to insulin-like growth factors I and II with picomolar affinity, Molecular Cancer Therapeutics, 10(9):1677-1685 (2011).
Author Unknown, Table 1: Toxicities of hu3F8 and ch14.18, presentation slide, 1 page (2017).
Cheung, I. Y. et al, Phase I trial of anti-GD2 monoclonal antibody hu3F8 plus GM-CSF: Impact of body weight, immunogenicity and anti-GD2 response on pharmacokinetics and survival, OncoImmunology, Accepted manuscript, 33 pages (2017).
Harding, F. A. et al, The Immunogenicity of humanized and fully human antibodies: Residual immunogenicity resides in the CDR regions, mAbs, 2(3): 256-265 (2010).
Kushner, B. H. et al, Phase I Study of Humanized Anti-GD2 Monoclonal Antibody hu3F8 and Granulocyte-Macrophage Colony-Stimulating Factor in Patients with Resistant Neuroblastoma, Abstract, 3 pages (2017).
Roitt, A. et al, Immunology, Moscow Mir., 200: 110-111 (1998). (corresponding excerpt from English textbook provided).
Singer, M. et al, Genes and Genomes, Moscow Mir., 1:63-64 (1998). (corresponding excerpt from English textbook provided).
Tong, W. et al, Small-molecule ligands of GD2 ganglioside, designed from NMR studies, exhibit induced-fit binding and bioactivity, Chem. Biol. 17(2): 183-94 (2010), with Supplemental Information, Chemistry and Biology, 27 pages.
Vajdos, F. F. et al, Comprehensive functional maps of the antigen-binding site of an anti-ErbB2 antibody obtained with shotgun scanning mutagenesis, J. Mol. Biol., 320(2): 415-428 (2002).
Zhuangsheng, T. et al, Immunotoxicology, Peking University Medical Press, 28-29 (2011). [No known English translation].

* cited by examiner

| Tumor type | hu3F8scFv Positive staining | Staining Intensity V1 | V1 D32H | V1 D32H E1K |
|---|---|---|---|---|
| Ewings | 3/9=33% | 3 | 4 | 4 |
| | | 3 | 4 | 4 |
| | | 4 | 4 | 4 |
| DSRCT | 6/10=60% | 0 | 1 | 1 |
| | | 0 | 1 | 1 |
| | | 1 | 3 | 3 |
| | | 1 | 4 | 4 |
| | | 3 | 4 | 4 |
| | | 3 | 4 | 4 |
| OS | 6/10=60% | 0 | 1 | 1 |
| | | 1 | 1 | 1 |
| | | 1 | 2 | 2 |
| | | 1 | 2 | 2 |
| | | 1 | 2 | 2 |
| | | 3 | 3 | 3 |
| RMS | 5/10=50% | 0 | 1 | 1 |
| | | 0 | 2 | 2 |
| | | 0 | 1 | 1 |
| | | 1 | 1 | 1 |
| | | 3 | 3 | 3 |

| Tumor type | hu3F8scFv Positive staining | Staining Intensity V1 | V1 D32H | V1 D32H E1K |
|---|---|---|---|---|
| NB | 14/14=100% | 0 | 2 | 3 |
| | | 0 | NA | 3 |
| | | 1 | 2 | 2 |
| | | 1 | 4 | NA |
| | | 2 | 4 | 4 |
| | | 2 | NA | 3 |
| | | 3 | 3 | 4 |
| | | 3 | 4 | 4 |
| | | 3 | NA | 4 |
| | | 3 | NA | 3 |
| | | 3 | NA | 4 |
| | | 4 | 4 | 4 |
| | | 4 | 4 | 4 |
| | | 4 | 4 | 4 |
| Sarcoma (adult trial) | 13/18=72% | 0 | 1 | 1 |
| | | 0 | 2 | 2 |
| | | 0 | 2 | 2 |
| | | 1 | 2 | 3 |
| | | 2 | 3 | 3 |
| | | 2 | 2 | 2 |
| | | 2 | 3 | 3 |
| | | 3 | 4 | 4 |
| | | 3 | 3 | 4 |
| | | 3 | 4 | 4 |
| | | 4 | 4 | 4 |
| | | 4 | 4 | 4 |
| | | 4 | 4 | 4 | scFv concentration is 3 μg/ml;
NB, Neuroblastoma; OS, osteosarcoma; RMS, Rhabdomyosarcoma; Ewings, Ewing's sarcoma; DSRCT, Desmoplastic small round cell tumor. The strength is defined as 0, 1 (weak, heterogeneous membrane staining), 2 (weak, homogeneous membrane staining), 3 (strong, heterogeneous membrane staining) and 4 (strong, homogeneous membrane staining).

FIG. 1

B184 (biotin-GD2)
Neu5Aca2-8Neu5Aca2-3[GalNAcb1-4]Galb1-4Glcb-SpNH-LC-LC-Biotin
from
Consortium for functional glycomics
Protein –glycan interaction core
Emory University
Biotin-PEG-GD2
Made from azido-GD2-oligosaccharide, reacted with biotin-(PEG)4-alkyne (using Click Chemistry)
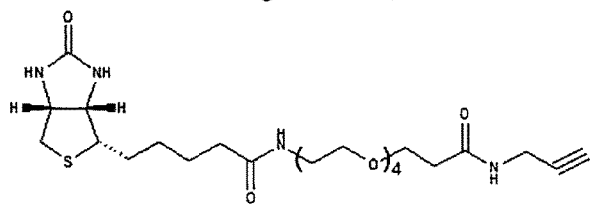
+
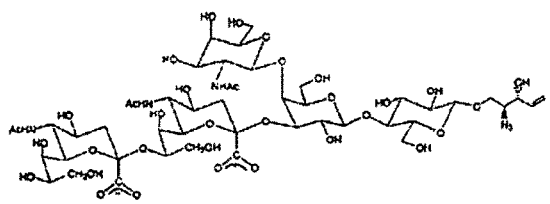
FIG. 2

HIGH AFFINITY ANTI-GD2 ANTIBODIES

CROSS REFERENCE TO RELATED APPLICATIONS

This application is a national stage entry under 35 USC § 371 of International Patent Application No. PCT/US2014/029308, filed Mar. 14, 2014 (the '308 application). The present application claims the benefit of priority thereto. The present application and the '308 application each claim the benefit of the filing date under 35 USC § 119(e) of U.S. Provisional Patent Application Ser. No. 61/801,287, filed Mar. 15, 2013 (the '287 application). The entire contents of each of the '308 and '287 applications are incorporated herein by reference.

SEQUENCE LISTING

The present specification makes reference to a sequence listing submitted in electronic Form as an ascii .txt file named "2003080-0638_ST25" on Mar. 14, 2014. The .txt file was generated on Mar. 12, 2014 and is 94 kb in size.

INTRODUCTION

Monoclonal antibody (MoAb) therapy is an accepted treatment modality for cancers, with five MoAbs having received FDA approval for solid tumors in adults, including colorectal and breast cancer, non small cell lung cancer, squamous cell carcinoma, and melanoma (Boyiadzis et al., 2008, Expert Opin Biol Ther 8, 1151-8; Yan et al., 2008, Cancer J 14, 178-83).

Among other things, the present invention provides the insight that MoAb therapy has remained inadequately exploited for the treatment of pediatric cancers. Unlike chemotherapy or radiation, MoAb therapy is not myelosuppressive and genotoxic, generally with few long term toxicities. These are critical considerations for young children. More importantly, MoAb is effective against metastatic cancer in blood, bone marrow and bone, typically found in high risk neuroblastoma (NB). As a class of agents, the pharmacokinetics and toxicities of human or humanized IgG1 antibodies have been extensively studied. In addition, antibodies can carry cytotoxic payloads, whether immune based, radioisotopes, toxins or enzymes, thereby increasing the options for targeted therapy.

SUMMARY

The present invention provides antibody agents that bind to GD2 and are variants of a reference 3F8 antibody in that they contain one or more particular structural features that are not found in the reference 3F8 antibody and are described herein. In some embodiments, provided antibody agents show improved stability and/or reduced immunogenicity relative to an otherwise identical 3F8 antibody lacking the one or more structural features described herein. In some embodiments, provided antibody agents are useful in medicine, for example in the diagnosis and/or treatment of NB. In some embodiments, provided antibody agents are associated with, comprise, and/or deliver one or more payloads (e.g., a detectable payload and/or a therapeutic payload). A variety of methodolodies for identifying, characterizing, preparing, and/or using such antibody agents are also provided by the present invention.

In this application are specifically described high affinity Anti-GD2 antibodies with a new hu3F8 framework, hu3F8V5, that is designed to have reduced immunogenicity but enhanced stability. The hu3F8V5 antibodies were designed by optimizing the framework structure of hu3F8V1 (described in WO 2011/160119 and Cheung et al., 2012, Oncoimmunology 1: 477-486), for reduced immunogenicity based on computational methods. First, the hu3F8V1 heavy chain and light chain sequences were compared to human germline sequences humIGHV 199 and humIGKV025, respectively (EMBL database). Molecular simulations using CHARMm (CHemistry at Harvard Molecular mechanics) force fields (B. R. Brooks et al., J. Comp. Chem. 30, 1545-1615 (2009)) were run on each potential humanizing mutation based on the crystal structure of murine 3F8 (protein data bank accession 3VFG), to determine if the mutation was structurally permissive. Additionally, MHC class II T-cell eptiopes in hu3F8V1 were identified using NN-align method on the Immune Epitope Database and minimized based on structurally permissive mutations. Based on a computational model of GD2 docked to the 3F8 crystal structure (built using CDOCKER and Discovery Studio softwares, Accelrys, San Diega, Calif.), CDR residues that were not modeled to directly interact with the GD2 antigen were considered for humanization mutations.

Nine point mutations were made in the hu3F8V1 to make hu3F8V5 (see Table 2) in an effort to reduce potential immunogenicity. All nine mutations were found to be structurally permissive to the computational model of 3F8 bound to its antigen GD2. All of the mutations involve changing murine residues left in the humanization on 3F8, to the human germline sequences. (LC:K24R, LC:S56T, LC:V58I, HC:I20L, HC:M92V) involve framework residues. We additionally found 4 mutations in CDR H2 (HC: A62S, HC: F63V, HC: M64K, HC: S56G) that removed a strong T-cell epitope as identified by in silico methods. We were surprised that our computational model of 3F8 bound to GD2 allowed suggested mutations in the CDR region since it is uncommon for one skilled in the art of antibody humanization by grafting methods to change CDR residues.

To perform affinity maturation based on yeast display methods, we first synthesized a novel biotinylated GD2 derivative to use for selection. We had previously been unsuccessful using a standard biotinylated GD2 antigen (obtained from Consortium for functional glycomics). A novel synthetic GD2-azido derivative (FIG. 2) was created by fusing a PEG spacer in order to observe GD2 in flow cytometry. Using this novel analog, we selected 2 mutations from a random library of hu3F8 ScFvs displayed on the surface of yeast, which had enhanced binding to the synthetic GD2 analog. The first one was LC:D32H which is located on CDR L1, and the second one was LC:E1K, which is a framework residue. The two mutations (LC: E1K and LC: D32H were tested in recombinantly expressed hu3F8V1 ScFv and hu3F8V5 ScFv constructs and binding affinities for native GD2 were measured using Biacore analysis. Based on structural modeling, all hu3F8 ScFv were made in the VL-VH format, because it allows for less restricted access to the antigen binding pocket. This is in contrast to most conventional ScFvs, which are constructed in the VH-VL format. Several variants were also tested in the full IgG1 format.

Therefore, the present invention provides novel high affinity anti-GD2 antibody agents, including intact antibodies, single chain variable fragments (scFv), and other formats, containing specific structural features (mutations relative to 3F8 and/or to hu3F8V1) which reduce immunogenicity and increase affinity of the antibody to GD2.

In one embodiment, the present invention provides a new framework for anti-GD2 3F8 antibody, namely hu3F8V5, having specific structural features (mutations relative to 3F8 and/or to hu3F8V1) which reduce its immunogenicity and remove a T-cell epitope.

It another embodiment, the present invention provides anti-GD2 antibody agents with increased affinity to GD2, the antibody agents having specific structural features in the light chain (LC), D32H located on CDR L1, and E1K a framework residue.

Anti-GD2 antibody agents with a particular structural feature in the heavy chain (HV), G54I, are also provided.

Antibody agents of the present invention can have a single structural feature described above, or two structural features in any combination as double features, or more than two structural features in any combination as triple features. In some embodiments, these structural features can be introduced into any form of a 3F8 antibody, for example into hu3F8V1, or in combination with other structural features already present in the 3F8 molecule for similar or alternative purposes, for example hu3F8V5. While antibodies and single chain variable fragment (scFv) harboring these structural features in both hu3F8V1 and hu3F8V5 are described herein, it is understood that the mutations can be incorporated into any 3F8 antibody sequence in order to effect enhanced affinity.

In one embodiment, the invention is directed to an 3F8 Anti-GD2 antibody having a light chain (LC) with one structural feature, either E1K or D32H, or two structural features, E1K and D32H, and/or a heavy chain (HC) with a G54I structural feature, as well as antibody compositions, glycoforms of the antibody, antibodies with enhanced stability, antibodies with enhanced binding to Fc receptors, antibodies with enhanced affinity to GD2, bispecific antibodies engineered to express a second distinct binding site or a bispecific T-cell engager, or use of the Fv fragments of any of the antibodies of the present invention in modular IgG construction for bispecific, tandem scFv bispecific antibodies that engage T cells (BiTE) antibodies, trispecific or multispecific antibodies. Such antibodies and encoding or complementary nucleic acids, vectors, host cells, compositions, formulations, devices, transgenic animals, transgenic plants related thereto, and methods of making and using thereof, as described and enabled herein, in combination with what is known in the art are part of the present invention. Surprisingly, the hu3F8 harboring any combination of the structural features E1K, D32H, and G54I show significantly more affinity to GD2, and significantly more PMN-ADCC and PBMC-ADCC activities than the parental hu3F8V1, with low complement mediated cytotoxicity (CMC). The low CMC is desirable since it is believed to mediate the pain side-effect associated with anti-GD2 immunotherapy. This superiority was consistently observed in ADCC asays irrespective of donors or if NK92 transfected with human CD16 or CD32 were used as killers. This was important since ADCC is the proven mechanism for anti-tumor effects of MoAb in patients in general.

In one embodiment the invention is directed to a 3F8 antibody agent comprising a light chain and a heavy chain based on hu3F8V1 or hu3F8V5 but differing in the presence of one or more structural features described herein, said antibody agent binding with high affinity to GD2 and mediating a desired effect, e g inhibiting cell growth in vitro, blocking pain side effects due to anti-GD2 antibody therapy, to name a few.

In one aspect, antibody agent of the invention include hu3F8V1 IgGs with a single structural feature described herein, e.g. hu3F8V1-E1K, hu3F8V1-D32H, hu3F8V1-G54I; hu3F8V1 IgGs with a double structural feature as described herein, e.g. hu3F8V1-E1KD32H, hu3F8V1-E1KG54I, and hu3F8V1-D32HG54I; hu3F8V1 IgGs with a triple structural feature as described herein, e.g. hu3F8V1-E1KD32HG54I; hu3F8V5 IgG; hu3F8V5 IgGs with a single structural feature as described herein, e.g. hu3F8V5-E1K, hu3F8V5-D32H, hu3F8V5-G54I; hu3F8V5 IgGs with a double structural feature as described herein, e.g. hu3F8V5-E1KD32H, hu3F8V5-E1KG54I, and hu3F8V5-D32HG54I; and hu3F8V5 IgGs with a triple structural feature as described herein, e.g. hu3F8V5-E1KD32HG54I.

The invention also includes fragments or a derivative of such an antibody, such as one or more portions of the antibody chain, such as the heavy chain constant, joining, diversity or variable regions, or the light chain constant, joining or variable regions. The antibodies can be of any class such as IgG, IgM, or IgA or any subclass such as IgG1, IgG2a, IgG4, and other subclasses known in the art. Antibodies useful in the present invention also include antigen-binding antibody fragments of the antibodies of the present invention including, but are not limited to, Fab, Fab' and F(ab')2, Fd, single-chain variable fragment (scFv), single-chain antibodies, disulfide-linked or disulfide-stabilized Fvs (sdFv or dsFv).

Single chain variable fragments of the present invention include hu3F8V1-E1K scFv, hu3F8V1-D32H scFv, hu3F8V1-G54I scFv; hu3F8V1 scFv with a double structural feature as described herein, e.g. hu3F8V1-E1KD32H scFv, hu3F8V1-E1KG54I scFv, and hu3F8V1-D32HG54I scFv; hu3F8V1 scFv with a triple structural feature as described herein, e.g. hu3F8V1-E1KD32HG54I scFv; hu3F8V5 scFv; hu3F8V5 scFv with a single structural feature as described herein, e.g. hu3F8V5-E1K scFv, hu3F8V5-D32H scFv, hu3F8V5-G54I scFv; hu3F8V5 scFv with a double structural feature as described herein, e.g. hu3F8V5-E1KD32H scFv, hu3F8V5-E1KG54I scFv, and hu3F8V5-D32HG54I scFv; hu3F8V5 scFv with a triple structural feature as described herein, e.g. hu3F8V5-E1KD32HG54I scFv, and combinations thereof.

The invention also includes single-domain antibodies comprising either a VL or VH domain. Further, the antibodies can be produced by any method, such as phage display, or produced in any organism, egg, or cell line, including bacteria, insect, yeast (fungi), mammal or other type of cell or cell line which produces antibodies with desired characteristics, such as humanized antibodies. The antibodies can also be formed by combining a Fab portion and a Fc region from different species, or by keeping the complementarity-determining regions and modifying the framework regions to that of another species.

Preferred anti-GD 2 antibodies of the present invention comprise any of the following peptide sequences:
  hu3F8V1 light chain with D32H structural feature identified as SEQ ID NO:1,
  hu3F8V1 light chain with E1K structural feature identified as SEQ ID NO:2,
  hu3F8V1 light chain with a double structural feature, D32H and E1K, identified as SEQ ID NO:3,
  hu3F8V1 heavy chain with G54I structural feature identified as SEQ ID NO:4,
  hu3F8V5 heavy chain gamma 1 identified as SEQ ID NO:5,
  hu3F8V5 light chain kappa identified as SEQ ID NO:6,
  hu3F8V5 light chain with D32H structural feature identified as SEQ ID NO:7, hu3F8V5 light chain with E1K structural feature identified as SEQ ID NO:8,
hu3F8V5 light chain with a double structural feature E1K and D32H identified as SEQ ID NO:9,
hu3F8V5 heavy chain with G54I structural feature identified as SEQ ID NO:10,
hu3F8V1 single chain variable fragment (scFv) having light chain variable region with D32H structural feature identified in SEQ ID NO:11,
hu3F8V1 scFv having light chain variable region with D32H structural feature and heavy chain variable region with G54I structural feature identified as SEQ ID NO:12,
hu3F8V1 scFv having light chain variable region with E1K structural feature identified as SEQ ID NO:13,
hu3F8V1 scFv having light chain variable region with E1K structural feature and heavy chain variable region with G54I structural feature identified as SEQ ID NO:14,
hu3F8V1 scFv having light chain variable region with E1K and D32H double structural feature identified as SEQ ID NO:15,
hu3F8V1 scFv having light chain variable region with E1K and D32H double structural feature and heavy chain variable region with G54I structural feature identified as SEQ ID NO:16,
hu3F8V1 scFv having heavy chain variable region with G54I structural feature identified as SEQ ID NO:17
hu3F8V5 scFv identified as SEQ ID NO:18,
hu3F8V5 scFv having light chain variable region with D32H structural feature identified as SEQ ID NO:19,
hu3F8V5 scFv having heavy chain variable region with G54I structural feature identified as SEQ ID NO:20.
hu3F8V5 scFv having light chain variable region with D32H structural feature and heavy chain variable region with G54I structural feature identified as SEQ ID NO:21,
hu3F8V5 scFv having light chain variable region with E1K structural feature identified as SEQ ID NO:22,
hu3F8V5 scFv having light chain variable region with E1K structural feature and heavy chain variable region with G54I structural feature identified as SEQ ID NO:23,
hu3F8V5 scFv having light chain variable region with E1K and D32H double structural feature identified as SEQ ID NO:24, and
hu3F8V5 scFv having light chain variable region with E1K and D32H double structural feature and heavy chain variable region with G54I structural feature identified as SEQ ID NO:25.

In another embodiment, the single chain variable fragments described above can be linked, with or without linkers or spacers, to other scFv with specificity to another antigen, to produce bivalent or bispecific anti-GD2 antibodies. For example, the scFv sequence for huOKT3 with a linker and spacer identified as SEQ ID NO:26, or without a spacer identified as SEQ ID NO:27, can follow any of the scFvs described in SEQ ID NOs: 11-25. Alternatively, the scFv sequence for C825, anti-DOTA identified as SEQ ID NO:28 can follow any of the scFv sequences identified in SEQ ID NO:11-25. Some examples of bispecific antibodies include:
hu3F8V1 scFv-linker-huOKT3 scFv with ADTKGP spacer identified as SEQ ID NO:29,
hu3F8V1 scFv-linker-huOKT3 scFv without spacer identified as SEQ ID NO:30, and
hu3F8V1 scFv-C825 scFv identified in SEQ ID NO:31.

In some embodiments of the present invention, provided antibody agents can be additionally modified with carbohydrate composition, for example to increase effector function, with a particular triple residue feature DEL (S239D/A330L/I332E) in the heavy chain of hu3F8V1, one or more structural features in the heavy chain and/or in the VH-VL Ala43Ser interface for enhanced stability, and/or combinations thereof.

Preferred antibody agents of the present invention are those that bind human GD2 and perform the desired function, i.e. effector function, blocking pain, or inhibiting cell growth. Certain representative methods for determining monoclonal antibody specificity and affinity by competitive inhibition can be found in Harlow, et al, Antibodies: A Laboratory Manual, Cold Spring Harbor Laboratory Press, Cold Spring Harbor, N. Y., 1988), hereby incorporated by reference thereto. At least one antibody of the invention binds at least one specified epitope specific to human GD2, subunit, fragment, portion or any combination thereof. The epitope can comprise at least one antibody binding region, which epitope is preferably comprised of at least 1-5 sugar residues or ceramide of at least one portion of GD2.

In one aspect, the present invention provides at least one isolated hu3F8 Anti-GD2 antibody of the present invention comprising any of the LC or HV harboring any of the structural features defined herein in any combination, and the nucleic acid sequences encoding same wherein:
hu3F8V1 light chain with single structural feature D32H is encoded by the polynucleotide identified in SEQ ID NO:32,
hu3F8V1 light chain double structural feature E1K and D32H is encoded by the polynucleotide identified in SEQ ID NO:33,
hu3F8V5 heavy chain is encoded by the polynucleotide identified in SEQ ID NO:34,
hu3F8V5 light chain is encoded by the polynucleotide identified in SEQ ID NO:35,
hu3F8V5 single structural feature D32H light chain is encoded by the polynucleotide identified in SEQ ID NO:36,
hu3F8V5 double structural feature E1K and D32H light chain is encoded by the polynucleotide identified in SEQ ID NO:37,
hu3F8V5 single structural feature G54I heavy chain is encoded by the polynucleotide identified in SEQ ID NO:38,
hu3F8V1 scFv with single structural feature D32H in the light chain region is encoded by the polynucleotide identified in SEQ ID NO:39,
hu3F8V1 scFv with double structural feature E1K and D32H in the light chain region is encoded by the polynucleotide identified in SEQ ID NO:40,
hu3F8V1 scFv triple structural feature with E1K and D32H structural features in the light chain region and G54I structural feature in the heavy chain region is encoded by the polynucleotide identified in SEQ ID NO:41,
hu3F8V5 scFv is encoded by the polynucleotide identified in SEQ ID NO:42,
hu3F8V5 scFv with a single structural feature D32H in the light chain region is encoded by the polynucleotide identified in SEQ ID NO:43,
hu3F8V5 scFv with double structural feature E1K and D32H in the light chain region is encoded by the polynucleotide identified in SEQ ID NO:44, and hu3F8V5 scFv with a triple structural feature, E1K and D32H in the light chain region and G54I in the heavy chain region is encoded by the polynucleotide identified in SEQ ID NO:45.

In some aspects, the present invention provides a diagnostic/detection or therapeutic immunoconjugate comprising an antibody component that comprises any of the 3F8 MoAbs or fragments thereof of the present invention, or an antibody fusion protein or fragment thereof that comprises any of the 3F8 antibodies or fragments thereof of the present invention, wherein the antibody component is bound to at least one diagnostic/detection agent or at least one therapeutic agent.

In some aspects, the present invention provides a therapeutic immunoconjugate comprising a therapeutic agent, for example selected from the group consisting of a radionuclide, boron, gadolinium or uranium atoms, an immunomodulator, such as a cytokine, a stem cell growth factor, a lymphotoxin, such as tumor necrosis factor (TNF), a hematopoietic factor such as an interleukin (IL), a colony stimulating factor (CSF) such as granulocyte-colony stimulating factor (G-CSF) or granulocyte macrophage-colony stimulating factor (GM-CSF)), an interferon (IFN) such as interferons-alpha, -beta or -gamma, and a stem cell growth factor, a hematopoietic factor, erythropoietin, thrombopoietin, an antibody, a hormone, a hormone antagonist, an enzyme, an enzyme inhibitor, a photoactive therapeutic agent, a cytotoxic drug, such as antimitotic, alkylating, antimetabolite, angiogenesis-inhibiting, apoptotic, alkaloid, COX-2-inhibiting and antibiotic agents, a cytotoxic toxin, such as plant, microbial, and animal toxins, and a synthetic variations thereof, an angiogenesis inhibitor, a different antibody and a combination thereof.

In some aspects, the present invention also provides a multivalent, multispecific antibody or fragment thereof comprising one or more antigen-binding sites having affinity toward an antigen recognized by the 3F8 antibody and one or more hapten binding sites having affinity towards epitopes or haptens besides GD2. In one embodiment, the multivalent, multispecific antibody or fragment thereof comprises a diagnostic/detection or therapeutic agent.

In some aspects, the present invention provides a method of delivering a diagnostic/detection agent, a therapeutic agent, or a combination thereof to a target, comprising: (i) administering to a subject a multivalent, multispecific antibody or fragment thereof of the present invention; (ii) waiting a sufficient amount of time for an amount of the non-binding protein to clear the subject's blood stream; and (iii) administering to said subject a carrier molecule comprising a diagnostic/detection agent, a therapeutic agent, or a combination thereof, that binds to a binding site of said antibody. In some embodiments, the diagnostic/detection agent or therapeutic agent is selected from the group comprising isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA, and combinations thereof. The second specificity also includes hapten(s) conjugated to any from the group of agents described. These haptens include, but not limited to biotin and its derivatives, DOTA and its derivatives, DTPA and its derivatives, fluorescein and its derivatives, histamine and its derivatives, Deferoxamine and its derivatives).

In any of the methods of the present invention, the subject is preferably a mammal, such as a human or domestic pet.

In some embodiments of the present invention is a method of treating or identifying diseased tissues in a subject, comprising: (A) administering to said subject a bi-specific antibody or antibody fragment having at least one arm that specifically binds a diseased tissue-associated marker and at least one other arm that specifically binds a targetable conjugate, wherein said diseased tissue-associated marker is an antigen recognized by the 3F8 MoAb; (B) optionally, administering to said subject a clearing composition, and allowing said composition to clear non-localized antibodies or antibody fragments from circulation; and (C) administering to said subject a first targetable conjugate which comprises a carrier portion which comprises or bears at least one epitope recognizable by said at least one other arm of said bi-specific antibody or antibody fragment, and one or more conjugated therapeutic or diagnostic agents. Preferably, at least one arm that specifically binds a targeted tissue is an Anti-GD2 antibody or a fragment of Anti-GD2 antibody of the present invention.

In some aspects, the present invention provides a method for detecting or treating tumors expressing an antigen recognized by a 3F8 MoAb in a mammal, comprising: (A) administering an effective amount of a bispecific antibody or antibody fragment comprising at least one arm that specifically binds a targeted tissue and at least one other arm that specifically binds a targetable conjugate, wherein said one arm that specifically binds a targeted tissue is a 3F8 antibody of the present invention or fragment thereof; and (B) administering a targetable conjugate. The targetable conjugate can be selected from the group consisting of (i) DOTA-Phe-Lys(HSG)-D-Tyr-Lys(HSG)-NH2; (ii) Ac-Lys(HSG)D-Tyr-Lys(HSG)-Lys(Tscg-Cys)-NH2; (iii) DOTA-D-Asp-D-Lys(HSG)-D-Asp-D-Lys(HSG)-NH2; (iv) DOTA-D-Glu-D-Lys(HSG)-D-Glu-D-Lys(HSG)-NH2; (v) DOTA-D-Tyr-D-Lys(HSG)-D-Glu-D-Lys(HSG)-NH2; (vi) DOTA-D-Ala-D-Lys(HSG)-D-Glu-D-Lys(HSG)-NH2; (vii) DOTA-D-Phe-D-Lys(HSG)-D-Tyr-D-Lys(HSG)-NH2; (viii) Ac-D-Phe-D-Lys(DOTA)-D-Tyr-D-Lys(DOTA)-NH2; (ix) Ac-D-Phe-D-Lys(DTPA)-D-Tyr-D-Lys(DTPA)-NH2; (x) Ac-D-Phe-D-Lys(Bz-DTPA)-D-Tyr-D-Lys(Bz-DTPA)-NH2; (xi) Ac-D-Lys(HSG)-D-Tyr-D-Lys(HSG)-D-Lys(Tscg-Cys)-NH2; (xii) DOTA-D-Phe-D-Lys(HSG)-D-Tyr-D-Lys(HSG)-D-Lys(Tscg-Cys)-NH2; (xiii) (Tscg-Cys)-D-Phe-D-Lys(HSG)-D-Tyr-D-Lys(HSG)-D-Lys(DOTA)-NH2; (xiv) Tscg-D-Cys-D-Glu-D-Lys(HSG)-D-Glu-D-Lys(HSG)-NH2; (xv) (Tscg-Cys)-D-Glu-D-Lys(HSG)-D-Glu-D-Lys(HSG)-NH2; (xvi) Ac-D-Cys-D-Lys(DOTA)-D-Tyr-D-Ala-D-Lys(DOTA)-D-Cys-NH2; (xvii) Ac-D-Cys-D-Lys(DTPA)-D-Tyr-D-Lys(DTPA)-NH2; (xviii) Ac-D-Lys(DTPA)-D-Tyr-D-Lys(DTPA)-D-Lys(Tscg-Cys)-NH2; (xix) Ac-D-Lys(DOTA)-D-Tyr-D-Lys(DOTA)-D-Lys(Tscg-Cys)-NH2; flurorescein and its derivatives; desferrioxamine and its derivatives.

In some aspects, the present invention provides a method of targeting wherein the method comprises: (A) injecting a subject who is to undergo such a procedure with a bispecific antibody F(ab)2 or F(ab')2 fragment, or single-chain Fv fragment, wherein the bispecific antibody or fragment has a first antibody binding site which specifically binds to an antigen recognized by an 3F8 MoAb of the present invention, and has a second antibody binding site which specifically binds to a hapten, and permitting the antibody fragment to accrete at target sites; (B) optionally clearing non-targeted antibody fragments using a clearing agent if the bispecific fragment is not largely cleared from circulation within about 24 hours of injection, and injecting a hapten-modified dextran, or dendrimers, or polymers, which quickly remove nontargeted antibody or fragments into the liver for degradation (C) detecting the presence of the hapten by nuclear imaging or close-range detection of elevated levels of accreted label at the target sites using scanners or probes, within hours of the first injection, and conducting said procedure, wherein said detection is performed without the use of a contrast agent or subtraction agent. In a preferred embodiment, the hapten is labeled with a diagnostic/detection radioisotope, a MRI image-enhancing agent, a fluorescent label or a chemiluminescent label. Fluorescent labels can include rhodamine, fluorescein, renographin, fluorescein isothiocyanate, phycoerytherin, phycocyanin, allophycocyanin, o-phthaldehyde and fluorescamine. Chemiluminescent labels can include luminol, isoluminol, an aromatic acridinium ester, an imidazole, an acridinium salt and an oxalate ester. MRI image-enhancing agents include gadolinium and ferromagnetic substances. Imaging of antibody-hapten localization detects intact tumor cells that carry GD2, which is critical for tumor staging, measurement of tumor response to treatment, detection of early relapse and tumor surveillance. Detection of antibody-hapten localization intraoperatively gives precise location of tumor and uncovers occult sites of disease, to allow complete surgical resection as part of a curative therapy for cancer.

Also considered in the present invention is a multivalent, multispecific antibody or fragment thereof comprising one or more antigen-binding sites having affinity toward an antigen recognized by the 3F8 antibody and one or more hapten binding sites having affinity towards epitopes or haptens on cells (lymphocytes, natural killer cells, neutrophils, myeloid cells, stem cells, neuro stem cells, mesenchymal stem cells, leukemia cells, cytotoxic lymphocytes and B-lymphocytes). These bispecific antibodies or fragments can be administered through various routes, including intravenous, intrathecally, and intratumorally into mammals including humans to target endogenous cells or exogenously infused cells to sites or tissues or cells that carry the antigen GD2. Alternatively, cells can be armed ex vivo using these bispecific antibodies or fragments before administration into mammals including humans.

Also considered in the present invention is the use of sequences of 3F8 or fragments there of, to create chimeric surface receptors specific for GD2 using genetic methods, to redirect cells (lymphocytes, natural killer cells, neutrophils, myeloid cells, stem cells, neuro stem cells, mesenchymal stem cells, leukemia cells, cytotoxic lymphocytes and B-lymphocytes) to GD2 bearing tissues, organs or tumors, both for diagnostic and for therapeutic applications.

The present invention provides, in one aspect, isolated nucleic acid molecules comprising, complementary, or hybridizing to, a polynucleotide encoding the aforementioned specific Anti-GD2 antibodies, comprising at least one specified sequence, domain, portion or variant thereof.

The present invention further provides recombinant vectors comprising said Anti-GD2 antibody nucleic acid molecules, host cells containing such nucleic acids and/or recombinant vectors, as well as methods of making and/or using such antibody nucleic acids, vectors and/or host cells. Thus, the invention comprises isolated nucleic acid encoding at least one isolated mammalian Anti-GD2 antibody or fragment thereof; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, CHO-S, DG44, BSC-1, Hep G2, 653, SP2/0, 293, HeLa, myeloma, or lymphoma cells, or any derivative, immortalized or transformed cell thereof. Also provided is a method for producing at least one Anti-GD2 antibody, comprising translating the antibody encoding nucleic acid under conditions in vitro, in vivo or in situ, such that the antibody is expressed in detectable or recoverable amounts, including methods that use vectors which allow protein expression to be amplified using growth and survival selection under the control of metabolic pathways or enzymes that include but are not limited to dhfr (dihydrofolate reductase) or GS (glutamine synthase).

The present invention also provides at least one method for expressing at least one aforementioned Anti-GD2 antibody in a host cell, comprising culturing a host cell as described herein under conditions wherein at least one Anti-GD2 antibody is expressed in detectable and/or recoverable amounts.

The present invention also provides at least one composition comprising (a) an isolated Anti-GD2 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition. In some of these compositions, the chimeric or humanized antibodies are conjugated to a cytotoxic agent (i.e., an agent that impairs the viability and/or the functions of a cell) such as a cytotoxic drug, a toxin or a radionuclide.

The present invention further provides at least one Anti-GD2 antibody method or composition, for administering a therapeutically effective amount to modulate or treat at least one GD2 related condition in a cell, tissue, organ, animal or patient and/or, prior to, subsequent to, or during a related condition, as known in the art and/or as described herein. Thus, the invention provides a method for diagnosing or treating a GD2 related condition in a cell, tissue, organ or animal, comprising contacting or administering a composition comprising an effective amount of at least one isolated Anti-GD2 antibody or fragment thereof of the invention with, or to, the cell, tissue, organ or animal. The method can optionally further comprise using an effective amount of 0.001-50 mg/kilogram of an Anti-GD2 antibody of the invention to the cells, tissue, organ or animal. The method can optionally further comprise the contacting or the administrating by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrathecal, intra-Ommaya, intravitreous, intraocular, intrasynovial, intrathoracic, intrauterine, intravesical, bolus, vaginal, rectal, buccal, sublingual, intranasal, or transdermal. The method can optionally further comprise administering, prior, concurrently, or after the antibody contacting or administering at least one composition comprising an effective amount of at least one compound or protein or cell selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromsucula-r blocker, an antimicrobial, an antipsoriatic, a corticosteriod, an anabolic steroid, an erythropoietin, an immunization, an immunoglobulin, antibody or antibody derived conjugates, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, an anti-proliferative agent, a cytokine, interleukin, growth factors, a cytokine antagonist, and an anti-TNFα, white cells, T-cells, LAK cells, TIL cells, natural killer (NK) cells, monocytes, NKT cells, engineered T cells or NK cells or monocytes or granulocytes.

The present invention further provides at least one Anti-GD2 antibody method for diagnosing at least one GD2 related condition in a cell, tissue, organ, animal or patient and/or, prior to, subsequent to, or during a related condition, as known in the art and/or as described herein.

The present invention also provides at least one composition, device and/or method of delivery for diagnosing of at least one Anti-GD2 antibody condition, according to the present invention.

Also provided is a composition comprising at least one isolated humanized Anti-GD2 antibody of the present invention and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an anti-proliferative agent, a cytokine, or a cytokine antagonist, a TNF antagonist, an antirheumatic, a muscle relaxant, a narcotic, a non-steroid anti-inflammatory drug (NTHE), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical; an antidepressant, an antipsychotic, a stimulant, an asthma medication, a beta agonist, an inhaled steroid, an epinephrine or analog.

Also provided is a medical device, comprising at least one isolated mammalian Anti-GD2 antibody of the invention, wherein the device is suitable to contacting or administering the at least one Anti-GD2 antibody by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intravitreous, intraocular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one chimeric or humanized Anti-GD2 antibody or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, mannitol, sucrose, mannose, other sugars, tween 80, or mixtures thereof in an aqueous diluent. In one aspect, in the kit, the concentration of Anti-GD2 antibody or specified portion or variant in the first container is reconstituted to a concentration of about 0.1 mg/ml to about 500 mg/ml with the contents of the second container. In another aspect, the second container further comprises an isotonicity agent. In another aspect, the second container further comprises a physiologically acceptable buffer. In one aspect, the disclosure provides a method of treating at least one GD2 characterized condition, comprising administering to a patient in need thereof a formulation provided in a kit and reconstituted prior to administration.

Also provided is an article of manufacture for human pharmaceutical or diagnostic use, comprising packaging material and a container comprising a solution or a lyophilized form of at least one isolated chimeric or humanized Anti-GD2 antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intravitreous, intraocular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

BRIEF DESCRIPTION OF THE DRAWING

The Drawing included herein, which is comprised of the following Figures, is for illustration purposes only not for limitation.

FIG. 1 shows the strength of staining intensity of different tumor types with hu3F8V1 scFvs.

FIG. 2 shows the chemical structure of Biotin-PEG-GD2 made from azido-GD2-oligosaccharide reacted with biotin-(PEG)4-alkyne using Click Chemistry.

DETAILED DESCRIPTION OF CERTAIN EMBODIMENTS

Certain Definitions

Figure 3:
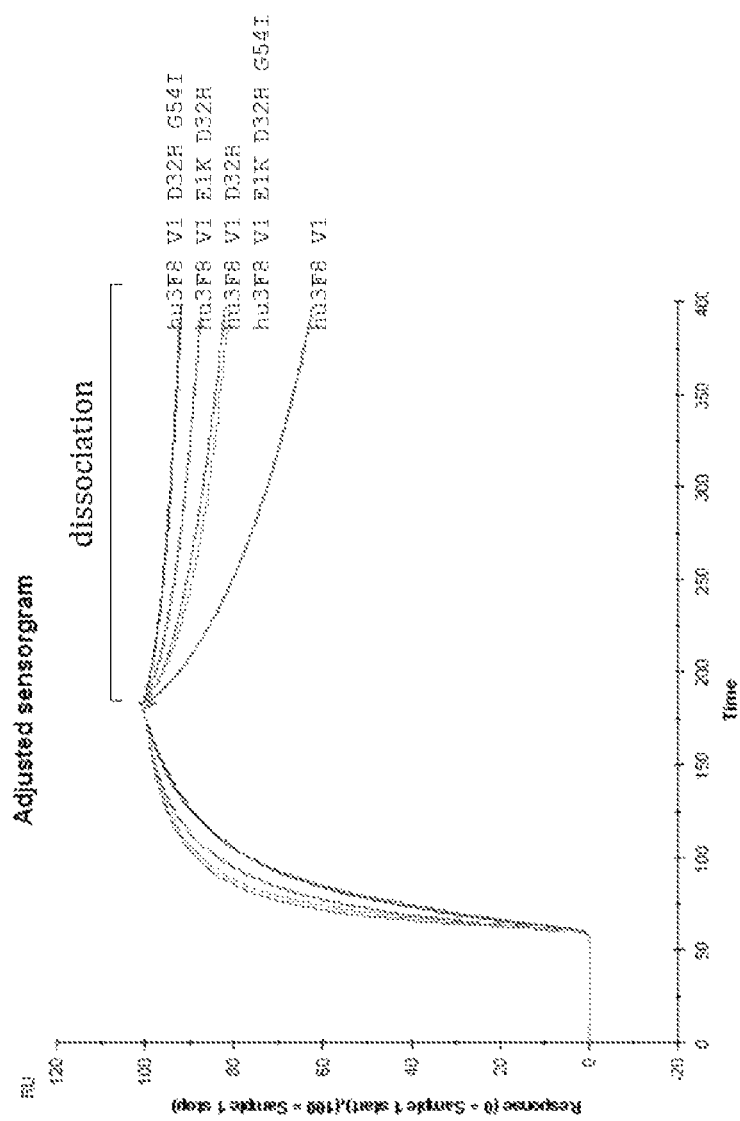
FIG. 3 shows Biacore sensorgrams of dissociation rates for exemplary hu3F8V1 IgGs.

In the description that follows, a number of terms used in recombinant DNA and immunology are extensively utilized. In order to provide a clearer and consistent understanding of the specification and claims, including the scope to be given such terms, the following definitions are provided.

Adult: As used herein, the term "adult" refers to a human eighteen years of age or older. Body weights among adults can vary widely with a typical range being 90 pounds to 250 pounds.

Affinity: As is known in the art, "affinity" is a measure of the tightness with a particular ligand (e.g., an antibody) binds to its partner (e.g., an epitope). Affinities can be measured in different ways.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by DV. In some embodiments, an animal may be a transgenic animal, genetically engineered animal, and/or a clone.

Antibody: The term "antibody" is art-recognized terminology and is intended to include molecules or active fragments of molecules that bind to known antigens. Examples of active fragments of molecules that bind to known antigens include Fab and F(ab')2 fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982). The term "antibody" also includes bispecific and chimeric antibodies, and other available formats.

In some embodiments, an antibody, as described herein, is or comprises to a full-length immunoglobulin molecule (e.g., an IgG antibody) or an immunologically active (i.e., specifically binding) portion of an immunoglobulin molecule, like an antibody fragment.

An antibody fragment is a portion of an antibody such as F(ab')2, F(ab)2, Fab', Fab, Fv, sFv and the like. Regardless of structure, an antibody fragment binds with the same antigen that is recognized by the intact antibody. For example, an 3F8 monoclonal antibody fragment binds with an epitope recognized by 3F8. The term "antibody fragment" also includes any synthetic or genetically engineered protein that includes antigen-binding structures of and acts like an antibody by binding to a specific antigen to form a complex. For example, antibody fragments include isolated fragments consisting of the variable regions, such as the "Fv" fragments consisting of the variable regions of the heavy or light chains, recombinant single chain polypeptide molecules in which light and heavy variable regions are connected by a peptide linker ("scFv proteins"), and minimal recognition units consisting of the amino acid residues that are or mimic the hypervariable region.

For example, in some embodiments, an antibody fragment comprises one or more, and in some embodiments all, of the complement determining regions (CDRs) found in a heavy or light chain of the parent antibody. In some embodiments, and antibody fragment further includes a sequencence adjacent a CDR. In some embodiments, an antibody fragment includes a sequence identical to a portion of the parent intact antibody; in some embodiments, the portion includes 1, 2, or 3 CDRs; in some embodiments, the portion corresponds to a full-length chain. In some embodiments, the portion is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50 or more amino acids in length.

The language "monoclonal antibody" is art-recognized terminology. Monoclonal antibodies are monospecific antibodies that are the same because they are made by one type of immune cell that are all clones of a unique parent cell.

A variety of methods exist in the art for the production of monoclonal antibodies. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NS0 cells, Simian COS cells, Chinese hamster ovary (CHO) cells, yeast cells, algae cells, eggs, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains of a desired species in place of the homologous human sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiments, an "antibody agent" is or comprises an antibody or fragment thereof, or an agent that comprises or consists of such antibody or fragment thereof.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Corresponding to: As used herein, the term "corresponding to" is often used to designate the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Epitope: The term "epitope" is art-recognized. It is generally understood by those of skill in the art to refer to the region of an antigen or antigens that interacts with an antibody. An epitope of a peptide or protein or sugar antigen can be linear or conformational, or can be formed by contiguous or noncontinguous amino acid and/or sugar sequences of the antigen. The GD2 molecule, like many carbohydrates, contains many epitopes. Those skilled in the art will appreciate that, in some embodiments, provided antibody agents may bind (e.g., cross-react) with variants of their target epitopes, for example that may contain substitutions, modifications, additions, deletions, or chemical mimetics of one or more amino acid or sugar residues. Such variant epitopes, and their use in accordance with provided antibody agents, are within the scope of the present invention. Anti-idiotypic antibodies are an embodiment of the present invention. In some embodiments, amino acid or sugar epitopes, or mimetic peptides/chemicals, or anti-idiotypic antibodies, offer a convenient method, for example, for eluting GD2 from MoAb or MoAb from GD2 on immunoaffinity columns. Further truncation of these epitopes may be possible.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Naked: In some embodiments, an antibody agent may be referred to as "naked" if it is not conjugated to payload (e.g., a diagnostic or therapeutic agent). Such naked antibody agents are useful in a variety of contexts, including because the Fc portion of the antibody molecule provides effector functions, such as complement fixation and ADCC (antibody-dependent cell cytotoxicity), which set mechanisms into action that may result in cell lysis. Naked antibodies include both polyclonal and monoclonal antibodies, as well as certain recombinant antibodies, such as chimeric, humanized or human antibodies. However, it is possible that the Fc portion is not required for therapeutic function, rather an antibody exerts its therapeutic effect through other mechanisms, such as induction of cell cycle resting and apoptosis. In this case, naked antibodies also include the unconjugated antibody fragments defined above.

Chimeric: A "chimeric" antibody is a recombinant protein that contains the variable domains including the complementarity-determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

Humanized: A "humanized" antibody is a recombinant protein in which the CDRs from an antibody from one species; e.g., a rodent antibody, are transferred from the heavy and light variable chains of the rodent antibody into human heavy and light variable domains. The constant domain of the antibody molecule is derived from those of a human antibody.

Human: The term "human" is often used to refer to an antibody obtained from transgenic mice that have been "engineered" to produce specific human antibodies in response to antigenic challenge. In such a technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993).

Human antibodies may also be generated by in vitro activated B cells. See U.S. Pat. Nos. 5,567,610 and 5,229,275, which are incorporated in their entirety by reference.

Therapeutic agent: A therapeutic agent is an entity that, when administered according to a particular regimen, tends to achieve a desired therapeutic benefit. In some embodiments, a therapeutic agent may be administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

Diagnostic agent: A diagnostic agent is an entity that is detectable when administered. In some embodiments, a diagnostic agentis administered conjugated to an antibody moiety, i.e., antibody or antibody fragment, or subfragment, and is useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In some embodiments, a diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as 223Ra for RAIT are encompassed by the invention.

Immunoconjugate: An "immunoconjugate" is a conjugate (i.e., a covalent linkage) of an antibody component with a payload (e.g., atherapeutic or diagnostic agent).

Immunomodulator: An "immunomodulator" is an agent hat when present, typically stimulates immune cells to proliferate or become activated in an immune response cascade, such as macrophages, B-cells, and/or T cells. An example of an immunomodulator as described herein is a cytokine. As the skilled artisan will understand, certain interleukins and interferons are examples of cytokines that stimulate T cell or other immune cell proliferation.

Expression Vector: An "expression vector" is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

Host cell: A recombinant "host cell" may be any prokaryotic or eukaryotic cell that contains either a cloning vector or expression vector. This term also includes those prokaryotic or eukaryotic cells, as well as transgenic animals, that have been genetically engineered to contain the cloned gene(s) in the chromosome or genome of the host cell or cells of the host cells.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Multispecific: A "multispecific" antibody is an antibody that can bind simultaneously to at least two targets that are of different structure, e.g., two different antigens, two different epitopes on the same antigen, or a hapten and an antigen or epitope. One specificity would be for, for example, a B-cell, T-cell, myeloid-, plasma-, or mast-cell antigen or epitope. Another specificity could be to a different antigen on the same cell type, such as CD20, CD19, CD21, CD23, CD46, CD80, HLA-DR, CD74, or CD22 on B-cells. Multispecific, multivalent antibodies are constructs that have more than one binding site, and the binding sites are of different specificity. For example, a bispecific diabody, where one binding site reacts with one antigen and the other with another antigen.

Bispecific: A "bispecific" antibody is an antibody that can bind simultaneously to two targets which are of different structure. Bispecific antibodies (bsAb) and bispecific antibody fragments (bsFab) have at least one arm that specifically binds to, for example, GD2 and at least one other arm that specifically binds to a targetable conjugate that bears a therapeutic or diagnostic agent. A variety of bispecific fusion proteins can be produced using molecular engineering. In one form, the bispecific fusion protein is divalent, consisting of, for example, a scFv with a single binding site for one antigen and a Fab fragment with a single binding site for a second antigen. In another form, the bispecific fusion protein is tetravalent, consisting of, for example, an IgG with two binding sites for one antigen and two identical scFv for a second antigen.

Recent methods for producing bispecific MoAbs include engineered recombinant MoAbs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering.

Bispecific fusion proteins linking two or more different single-chain antibodies or antibody fragments are produced in similar manner. Recombinant methods can be used to produce a variety of fusion proteins. In some embodiments, a flexible linker connects the scFv to the constant region of the heavy chain of the 3F8 antibody. Alternatively, the scFv can be connected to the constant region of the light chain of another humanized antibody. Appropriate linker sequences necessary for the in-frame connection of the heavy chain Fd to the scFv are introduced into the VL and Vkappa domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an hu3F8 antibody. The resulting vector can be used to transfect an appropriate host cell, such as a mammalian cell for the expression of the bispecific fusion protein.

In some embodiments, hu3F8 antibodies and fragments thereof of the present invention can also be used to prepare functional bispecific single-chain antibodies (bscAb), also called diabodies, and can be produced in mammalian cells using recombinant methods. See, e.g., Mack et al., Proc. Natl. Acad. Sci., 92: 7021-7025, 1995, incorporated herein by reference. For example, bscAb are produced by joining two single-chain Fv fragments via a glycine-serine linker using recombinant methods. The V light-chain and V heavy-chain domains of two antibodies of interest are isolated using standard PCR methods known in the art. Bispecific single-chain antibodies and bispecific fusion proteins are included within the scope of the present invention.

In some embodiments, the ultimate use of the bispecific diabodies described herein is for pre-targeting GD2 positive cells for subsequent specific delivery of diagnostic/detection or therapeutic agents. These diabodies bind selectively to targeted antigens allowing for increased affinity and a longer residence time at the desired location. Moreover, non-antigen bound diabodies are cleared from the body quickly and exposure of normal tissues is minimized. In certain particular embodiments, diabodies for use herein may comprise or be conjugated to one or more diagnostic/detection and/or therapeutic agents such as, for example, isotopes, drugs, toxins, cytokines, hormones, growth factors, conjugates, radionuclides, and metals. For example, gadolinium metal is used for magnetic resonance imaging (MRI). Radionuclides are also available as diagnostic and therapeutic agents (whether with diabodies or otherwise), especially those in the energy range of 60 to 4,000 keV.

The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may be used.

Peptide: Peptides having as few as two amino-acid residues may be used, preferably two to ten residues, in some embodiments also coupled to other moieties such as chelating agents.

Polypeptide: The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 4, 5, 10, and the light chain immunoglobulin molecules represented in SEQ ID NOS: 1, 2, 3, 6, 7, 8, 9, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

Linker: In some embodiments, a "linker" utilized in a conjugate should have a low molecular weight as compared with the conjugate, preferably having a molecular weight of less than 50,000 daltons, and advantageously less than about 20,000 daltons, 10,000 daltons or 5,000 daltons, including the metal ions that may be in chelates. In some embodiments, the presence of hydrophilic chelate moieties on the linker moieties can help to ensure rapid in vivo clearance. In addition to hydrophilicity, chelators may be chosen for their metal-binding properties, and may be changed at will since, at least for those linkers whose bsAb epitope is part of the peptide or is a non-chelate chemical hapten, recognition of the metal-chelate complex is no longer an issue.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Chelator: A chelator such as DTPA, DOTA, TETA, or NOTA may be utilized in any of a variety of circumstances, including in conjugates. The same chelators, when complexed with non-radioactive metals, such as Mn, Fe and Gd can be used for MRI, when used along with the bsAbs of the invention. Macrocyclic chelators such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

Conjugate: In some embodiments, provided antibody agents are utilized in conjucgates. In some particular embodiments, A chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Joni et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130: 1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Prevent: As used herein, the terms "prevent", "preventing" and "prevention" refer to the prevention of the recurrence or onset of one or more symptoms of a disorder in a subject as result of the administration of a prophylactic or therapeutic agent.

Combination: As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

Effector Function: "Effector function" as used herein is meant a biochemical event that results from the interaction of an antibody Fc region with an Fc receptor or ligand. Effector functions include but are not limited to antibody dependent cell mediated cytotoxicity (ADCC), antibody dependent cell mediated phagocytosis (ADCP), and complement mediated cytotoxicity (CMC). Effector functions include both those that operate after the binding of an antigen and those that operate independent of antigen binding.

Effector Cell: "Effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, large granular lymphocytes, Langerhans' cells, natural killer (NK) cells, T-lymphoctes, B-lymphocytes and may be from any organism including but not limited to humans, mice, rats, rabbits, and monkeys.

Fc Ligand: "Fc ligand" as used herein is meant a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FcεRII (CD23), FcRn, Clq, C3, staphylococcal protein A, streptococcal protein G, and viral FcγR. Fc ligands may include undiscovered molecules that bind Fc.

Derivative: As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

Fragment: As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

Effective amount: Effective Amount: As used herein, the term "effective amount" refers to an amount of a given compound, conjugate or composition that is necessary or sufficient to realize a desired biologic effect. An effective amount of a given compound, conjugate or composition in accordance with the methods of the present invention would be the amount that achieves this selected result, and such an amount can be determined as a matter of routine by a person skilled in the art, using assays that are known in the art and/or that are described herein, without the need for undue experimentation. For example, an effective amount for treating or preventing cancer metastasis could be that amount necessary to prevent migration and invasion of a tumor cell across the basement membrane or across an endothelial layer in vivo. The term is also synonymous with "sufficient amount." The effective amount for any particular application can vary depending on such factors as the disease, disorder or condition being treated, the particular composition being administered, the route of administration, the size of the subject, and/or the severity of the disease or condition. One of ordinary skill in the art can determine empirically the effective amount of a particular compound, conjugate or composition of the present invention, in accordance with the guidance provided herein, without necessitating undue experimentation.

About: As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

Isolated: By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Small Molecule: In general, a "small molecule" is a molecule that is less than about 5 kilodaltons (kD) in size. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the terms "treatment," "treat," "treated" or "treating" refer to prophylaxis and/or therapy, particularly wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. By "subject" or "individual" or "animal" or "patient" or "mammal," is meant any subject, particularly a mammalian subject, for whom diagnosis, prognosis, or therapy is desired. Mammalian subjects include humans and other primates, domestic animals, farm animals, and zoo, sports, or pet animals such as dogs, cats, guinea pigs, rabbits, rats, mice, horses, cattle, cows, and the like.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Neuroblastoma

Neuroblastoma (NB) is the most common extracranial solid tumor of childhood. In ~50% of cases, curative strategies must tackle both soft tissue mass and metastases in the bone marrow (BM). Dose-intensive chemotherapy improves tumor resectability, and post-surgical irradiation reduces the risk of relapse in the primary site to <10% (Kushner et al., 2001, J Clin Oncol 19, 2821-8). However, BM disease, as evidenced by histology or metaiodobenzylguanidine (MIBG) scan, often persists and forebodes a lethal outcome (Matthay et al., 2003, J Clin Oncol 21, 2486-91; Schmidt et al., 2008, Eur J Cancer 44, 1552-8). In addition, osteomedullary relapse is common, despite achieving near complete remission after induction therapy. Attempts at treatment intensification have met with both acute and long-term side effects, both of grave concern for young patients. There is a scarcity of promising new agents, and to date, few if any target/pathway-specific small molecules have shown major clinical benefit in patients with NB, although many promising leads continue to accumulate. With a cure rate of <30% at toxicity limits among stage 4 patients diagnosed at >18 months of age, there is substantial room for improvement (Pearson et al., 2008, Lancet Oncol 9, 247-56).

The present invention encompasses the recognition that several factors make NB well suited for MoAb targeted immunotherapy. First, MoAb mediates highly efficient antibody-dependent cellular cytotoxicity (ADCC) of NB in the presence of human white cells. Second, MoAb induces complement-mediated cytotoxicity (CMC) of NB cells, which lack decay accelerating factor CD55 (Cheung et al., 1988, J Clin Invest 81, 1122-8) and homologous restriction factor CD59 (Chen et al., 2000, Cancer Res 60, 3013-8). Complement deposition on NB cells enhances ADCC through activation of the iC3b receptor on neutrophils (Kushner and Cheung, 1992, Blood 79, 1484-90, Metelitsa et al., 2002, Blood 99, 4166-73), available even after dose-intensive or myeloablative chemotherapy plus stem cell transplantation, if colony stimulating factors are given (Mackall, C L, 2000, Stem Cells 18, 10-8). Third, the use of intensive chemotherapy (standard of care for NB) to achieve clinical remission causes prolonged lymphopenia and immunosuppression (Mackall et al., 2000, Blood 96, 754-762), such that patients are less likely to reject murine, chimeric or humanized MoAbs (Kushner et al., 2007, Pediatr Blood Cancer 48, 430-4).

Reference Anti-GD2 Antibodies

GD2 is a disialoganglioside abundant on tumors of neuroectodermal origin, including neuroblastoma and melonoma with highly restricted expression in normal tissues. At least two anti-GD2 antibody families have been tested clinically for the treatment of NB, i.e. 3F8 (Cheung et al., 1985, Cancer Res 45, 2642-9) and 14.18 (Mujoo et al., 1989, Cancer Res 49, 2857-61).

Chimeric ch14.18 consists of the variable region of murine MoAb 14.18 and the constant regions of human IgG1-K (Gillies et al., 1989, J Immunol Methods 125, 191-202). It demonstrates ADCC and CMC of NB and melanoma cells in vivo (Barker et al., 1991, Cancer Res 51, 144-9; Barker and Reisfeld, 1993, Cancer Res. 52, 362-7; Mueller et al., 1990, PNAS USA 87, 5702-05). Based on encouraging clinical responses in phase I studies, ch14.18 was tested in large phase II studies as consolidation therapy for stage 4 NB (German NB90 and NB97 studies). For the 166 patients >12 months at diagnosis, even though event-free survival (EFS) was similar in patients receiving ch14.18 when compared to patients on maintenance chemotherapy, overall survival (OS) was improved, and the rate of BM relapse reduced in patients treated with ch14.18 (Simon et al., 2004, J Clin Oncol 22, 3549-57).

In 2001, the Children's Oncology Group (COG) initiated a randomized phase III trial to study the efficacy of the combination of ch14.18 with GMCSF and IL-2 in preventing NB relapse in patients in complete remission (CR) after autologous stem-cell transplantation (ASCT) (ClinicalTrials.gov NCT00026312) (Gilman et al., J Clin Oncol 27:85-91, 2009), where a significant improvement in progression free survival (PFS) and OS at 2 years was found (Yu et al., N Engl J Med 363:1324-1334, 2010).

3F8, a murine IgG3 MoAb specific for GD2, induces cell death, and mediates efficient ADCC and CMC against NB in vitro (Cheung et al., 2007, supra). Among patients with chemoresistant marrow disease despite dose-intensive induction plus an aggressive salvage regimen, 80% achieved BM remission usually after 1 to 2 cycles of 5-day antibody plus GM-CSF therapy (Kushner et al., 2007, Proc Amer Soc Clin Oncol 25, 526s). Given the activity of m3F8 against chemoresistant marrow disease, the use of m3F8 was expanded to patients in their first remission with encouraging results. These favorable clinical outcomes in children could be improved if m3F8 is given as maintenance therapy over the first 3-5 years of highest recurrence risk. However, human anti-mouse antibody response (HAMA) is a limiting factor when the immune system recovers when chemotherapy is finished. One strategy to reduce HAMA is to chimerize or humanize 3F8.

We have previously described the engineering and isolation of humanized 3F8 (hu3F8-IgG1 H1L1, hereafter hu3F8V1) (described in WO 2011/160119 and Cheung et al., 2012, Oncoimmunology 1: 477-486, both incorporated in their entirety by reference thereto). These antibodies were made using standard recombinant methods, and selected for high expression by CHO-DG44 cell lines in serum free medium. Measured using surface Plasmon resonance used by Biacore systems, humanized 3F8 maintained a KD similar to that of m3F8. In contrast to other anti-GD2 antibodies, hu3F8V1 had substantially slower koff, which translated into a slower wash off in vitro. Like m3F8, humanized 3F8 inhibited cell growth in vitro, not typical for other anti-GD2 antibodies. Both blood mononuclear cell (PBMC)-ADCC and neutrophil (PMN)-ADCC of hu3F8V1, were superior (10 to >1000 fold) to that of m3F8, while CMC was inferior. This superiority was consistently observed in ADCC assays, irrespective of donors or if NK92 transfected with human CD16 or CD32 were used as killers. Hu3F8V1 showed superior anti-tumor effect against NB xenografts when compared to m3F8.

Provided Antibody Agents

The present invention encompasses the recognition that, in order to enhance therapeutic efficiency, new humanized forms of the antibody with enhanced affinity are needed. The present invention encompasses the recognition that it would be desirable to develop antibodies (or other antibody agents) that are variants of 3F8 and/or of hu3F8V1. The present invention particularly provides such antibodies and antibody agents. That is, the present invention provides various antibody agents that show significant structural identity with 3F8 and/or of hu3F8V1 and moreover show improved functional characteristics (e.g., stabilization and/or affinity or specificity) as compared with that observed with 3F8 and/or of hu3F8V1. In a preferred specific embodiment, the invention encompasses a molecule comprising a variant Fc region, wherein said variant Fc region comprises at least one amino acid modification relative to a wild-type Fc region, such that said molecule has an altered affinity for an FcγR, provided that said variant Fc region does not have a substitution at positions that make a direct contact with FcγR based on crystallographic and structural analysis of Fc-FcγR interactions such as those disclosed by Sondermann et al., 2000 (Nature, 406: 267-273 which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that makes a direct contact with an FcγR based on structural and crystallographic analysis.

One aspect of the invention includes hu3F8 antibody with altered affinities for activating and/or inhibitory receptors, having variant Fc regions with one or more amino acid modifications, wherein said one or more amino acid modification is a substitution at position 239 with aspartic acid, at position 330 with Leucine and at position 332 with glutamic acid.

The invention encompasses molecules comprising a variant Fc region with additions, deletions, and/or substitutions to one or more amino acids in the Fc region of an antibody of the present invention relative to a reference antibody (e.g., a reference 3F8 antibody) Fc region, for example in order to alter effector function, or enhance or diminish affinity of the provided Fc to FcR. It is within the skill of a person in the art, given the guidance provided herein, to prepare and use such variant Fc regions. Therefore, the invention encompasses molecules comprising variant Fc regions that bind with a greater affinity to one or more FcγRs. Such molecules preferably mediate effector function more effectively as discussed infra.

In some embodiments, the invention encompasses molecules comprising a variant Fc region that bind with a weaker affinity to one or more FcγRs than does a reference antibody (e.g., a reference 3F8 antibody) Fc region. Reduction or elimination of effector function is desirable in certain cases for example in the case of antibodies whose mechanism of action involves blocking or antagonism but not killing of the cells bearing a target antigen. Reduction or elimination of effector function would be desirable in cases of autoimmune disease where one would block FcγR activating receptors in effector cells (This type of function would be present in the host cells). In general increased effector function would be directed to tumor and foreign cells.

In certain embodiments, Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In some embodiments, Fc variants of the present invention are incorporated into an antibody agent (e.g., an antibody or an Fc fusion) that comprises one or more engineered glycoforms, i.e., a carbohydrate composition that is covalently attached to a molecule comprising an Fc region, wherein said carbohydrate composition differs chemically from that of a parent molecule comprising an Fc region.

The invention encompasses antibodies with modified glycosylation sites, preferably without altering the functionality of the antibody, e.g., binding activity GD2. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. An Fc-glycoform, hu3F8-H1L1-IgG1n that lacked certain oligosaccharides including fucose and terminal N-acetylglucosamine was produced in special CHO cells and exhibited enhanced ADCC effector function.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of an antibody of the invention by deleting one or more endogenous carbohydrate moieties of the antibody. In a specific embodiment, the invention encompasses deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, JMB, 336: 1239-49 each of which is incorporated herein by reference in its entirety.

Also included as polypeptides of the present invention are fragments, derivatives, analogs, or variants of the foregoing polypeptides, and any combination thereof. The terms "fragment," "variant," "derivative" and "analog" when referring to Anti-GD2 antibodies or antibody polypeptides include any polypeptides which retain at least some of the antigen-binding properties of the corresponding native antibody or polypeptide, i.e., those polypeptides that retain the ability to bind to one or more epitopes on GD2.

Fragments of polypeptides of the present invention include proteolytic fragments, as well as deletion fragments, in addition to specific antibody fragments discussed elsewhere herein.

Variants of Anti-GD2 antibodies and antibody polypeptides useful in accordance with the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques or unnatural amino acids. Variant polypeptides may comprise conservative or non-conservative amino acid substitutions, deletions or additions.

Derivatives of Anti-GD2 antibodies and antibody polypeptides useful in accordance with the present invention are polypeptides which have been altered so as to exhibit additional features not found on the native polypeptide. Examples include fusion proteins. Variant polypeptides may also be referred to herein as "polypeptide analogs." As used herein a "derivative" of an Anti-GD2 antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

In some embodiments, provided antibody agents show functional properties as set forth in the Examples herein. For example, in some embodiments, provided agents show improved binding relative to a parent 3F8 antibody and/or a humanized version thereof (e.g., hu3F8V1). Exemplary humanized versions include those having one or more structural features as described herein. In some certain embodiments, a structural feature includes one or more amino acid substutions that corresponds to a sequence that appears in a human frawework region of an immunoglobulin variable region sequence. In some certain embodiments, a structural feature includes one or more amino acid substitutions that corresponds to a sequence that appears in a human CDR region of an immunoglobulin variable region sequence. In some certain embodiments, a structural feature includes one or more amino acid substitutions that reduce immunogenicity of the provided agent relative to a parent antibody. In some certain embodiments, a structural feature includes one or more amino acid substutions that reduces, ameliorates or eliminates a T cell epitope of the provided agent relative to a parent antibody. In some embodiments, provided agents have a structural feature that includes those shown in Table 2.

In some embodiments, provided antibody agents bind to GD2 with an affinity of at least 5%, 10%, 15%, 20%, 25%, 30%, 35%, 40%, 45%, 50%, 55%, 60%, 65%, 70%, 75%, 80%, 85%, 90% or more than the affinity of a different antibody that binds GD2. In some embodiments, provided antibody agents bind GD2 with an affinity of at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold more than the affinity of a different antibody for GD2. In some embodiments, provided antibody agents bind GD2 with an affinity of greater than 20-fold, greater than 30-fold, greater than 40-fold, greater than 50-fold, greater than 60-fold, greater than 70-fold, greater than 80-fold, greater than 90-fold, or greater than 100-fold than that of a different antibody that binds GD2. In some embodiments, provided antibody agents show binding affinities for different gangliosides, such as, e.g., GD1b, that are within 2, within 3, within 4, within 5, within 6, within 7, within 8, within 9, or within 10-fold affinity of one another.

In some embodiments, provided antibody agents show a relative potency (e.g., ratio of 3F8 $EC_{50}$/antibody $EC_{50}$ or hu3F8V1 $EC_{50}$/antibody $EC_{50}$) in an ADCC or CMC assay within a range as described and/or exemplified herein. In some embodiments, provided antibody agents show a relative potency of at least 1.0, at least 1.5, at least 2.0, at least 2.5, at least 3.0, at least 3.5, at least 4.0, at least 4.5, at least 5.0, at least 5.5, at least 6.0, at least 6.5, at least 7.0, at least 7.5, at least 8.0, at least 8.5, at least 9.0, at least 9.5, at least 10.0, at least 10.5, at least 11.0, at least 11.5, at least 12.0, at least 12.5, at least 13.0, at least 13.5, at least 14.0, at least 14.5, at least 15.0, at least 15.5, at least 16.0, at least 16.5, at least 17.0, at least 17.5, at least 18.0, at least 18.5, at least 19.0, at least 19.5, at least 20.0, at least 20.5, at least 21.0, at least 21.5, at least 22.0, at least 22.5, at least 23.0, at least 23.5, at least 24.0, at least 24.5, at least 25.0, at least 25.5, at least 26.0, at least 26.5, at least 27.0, at least 27.5, at least 28.0, at least 28.5, at least 29.0, at least 29.5, or at least 30.0 as compared to a parent antibody that binds GD2.

In some embodiments, provided antibody agents show binding to GD2 with a $K_D$ (nM) less than 100 nM, less than 90 nM, less than 80 M, less than 70 nM, less than 60 nM, less than 50 nM, less than 40 nM, less than 30 nM, less than 20 nM, or less than 10 nM. In some certain embodiments, provided antibody agents show binding to GD2 with a $K_D$ (nM) less than 9 nM, less than 8 nM, less than 7 nM, less than 6 nM, less than 5 nM, less than 4 nM, less than 3 nM, less than 2 nM, or less than 1 nM. In some certain embodiments, provided antibody agents show binding to GD2 with a $K_D$ (nM) of about 0.2 nM, about 0.3 nM, about 0.4 nM, about 0.5 nM, about 0.6 nM, about 0.7 nM, about 0.8 nM, about 0.9 nM, about 1.0 nM, about 1.1 nM, about 1.2 nM, about 1.3 nM, about 1.4 nM, about 1.5 nM, about 1.6 nM, about 1.7 nM, about 1.8 nM, about 1.9 nM, about 2.0 nM, about 2.1 nM, about 2.2 nM, about 2.3 nM, about 2.4 nM, about 2.5 nM, about 2.6 nM, about 2.7 nM, about 2.8 nM, about 2.9 nM, or about 3.0 nM. In some certain embodiments, provided antibody agents show binding to GD2 with a $K_D$ (nM) of about 1 nM, about 2 nM, about 3 nM, about 4 nM, about 5 nM, about 6 nM, about 7 nM, about 8 nM, or about 9 nM.

In some embodiments, provided antibody agents show binding to GD2 with a $K_{off}(s^{-1})$ whose lower bound is about $2.0\times10^{-4}$ $s^{-1}$ and upper bound is about $20.0\times10^{-4}$ $s^{-1}$. In some embodiments, provided antibody agents show binding to GD2 with a $K_{off}(s^{-1})$ whose lower bound is selected from the group consisting of $2\times10^{-4}$ $s^{-1}$, $3\times10^{-4}$ $s^{-1}$, $4\times10^{-4}$ $s^{-1}$, $5\times10^{-4}$ $s^{-1}$, $6\times10^{-4}$ $s^{-1}$, $7\times10^{-4}$ $s^{-1}$, $8\times10^{-4}$ $s^{-1}$, $9\times10^{-4}$ $s^{-1}$, or more, and whose upper bound is higher than the lower bound and is selected from the group consisting of $10\times10^{-4}$ $s^{-1}$, $11\times10^{-4}$ $s^{-1}$, $12\times10^{-4}$ $s^{-1}$, $13\times10^{-4}$ $s^{-1}$, $14\times10^{-4}$ $s^{-1}$, $15\times10^{-4}$ $s^{-1}$, $16\times10^{-4}$ $s^{-1}$, $17\times10^{-4}$ $s^1$, $18\times10^{-4}$ $s^{-1}$, $19\times10^{-4}$ $s^{-1}$, $20\times10^{-4}$ $s^{-1}$, or more. In some certain embodiments, provided antibody agents show binding to GD2 with a $K_{off}(s^{-1})$ of about $2.9\times10^{-4}$ $s^{-1}$, $5.1\times10^{-4}$ $s^{-1}$, $6.9\times10^4$ $s^{-1}$, $8.8\times10^{-4}$ $s^{-1}$, or $18.5\times10^{-4}$ $s^{-1}$.

Humanized Antibody Agents

In one embodiment, the antibodies provided by the present invention are monoclonal antibodies, which in a preferred embodiment are humanized versions of cognate Anti-GD2 antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Similarly, forward mutations may be made to revert back to murine sequence for a desired reason, e.g. stability or affinity to antigen. For example, for hu3F8-H1L1 (or hu3F8V1) backmutations were necessary at 19 positions in the heavy chain sequence and 17 positions in the light chain in order to maintain the in vitro affinity of binding. Humanized antibodies generally are less likely to elicit an immune response in humans as compared to chimeric human antibodies because the former contain considerably fewer non-human components.

Suitable methods for making humanized antibodies of the present invention are described in, e.g., Winter EP 0 239 400; Jones et al., Nature 321:522-525 (1986); Riechmann et al., Nature 332:323-327 (1988); Verhoeyen et al., Science 239: 1534-1536 (1988); Queen et al., Proc. Nat. Acad. ScL USA 86:10029 (1989); U.S. Pat. No. 6,180,370; and Orlandi et al., Proc. Natl. Acad. Sd. USA 86:3833 (1989); the disclosures of all of which are incorporated by reference herein in their entireties. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs, encoding the CDRs are inserted into the corresponding regions of a human antibody heavy or light chain variable domain coding sequences, attached to human constant region gene segments of a desired isotype (e.g., γ1 for CH and κ for CL), are gene synthesized. The humanized heavy and light chain genes are co-expressed in mammalian host cells (e.g., CHO or NSO cells) to produce soluble humanized antibody. To facilitate large scale production of antibodies, it is often desirable select for high expressor using a DHFR gene or GS gene in the producer line. These producer cell lines are cultured in bioreactors, or hollow fiber culture system, or WAVE technology, to produce bulk cultures of soluble antibody, or to produce transgenic mammals (e.g., goats, cows, or sheep) that express the antibody in milk (see, e.g., U.S. Pat. No. 5,827,690).

Using the above-described approaches, humanized and chimeric versions of the 3F8 antibody, were generated. The cDNAs encoding the murine 3F8 variable regions of the light and heavy chains were used to construct vectors for expression of murine-human chimeras in which the murine 3F8 variable regions were linked to human IgG1 (for heavy chain) and human kappa (for light chain) constant regions, as described previously. In addition, novel forms of hu3F8 with variant glycosylation were created, in order to enhance binding to the Fc receptor and enhance antigen affinity.

In order to produce humanized 3F8 antibodies, the human acceptor framework domains were chosen by homology matching to human germline sequences. Using these chosen human acceptor frameworks, the light and heavy chain variable domains were designed and a number of variants/versions of each were generated and expressed, as described below in Examples.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies produced using other techniques but retaining the variable regions of the Anti-GD2 antibody of the present invention are part of this invention. Human antibodies can also be produced using transgenic mice which are incapable of expressing functional endogenous mouse immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human MoAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

As used herein, an "Anti-GD2 antibody", "Anti-GD2 antibody portion," or "Anti-GD2 antibody fragment" and/or "Anti-GD2 antibody variant" and the like include any protein or peptide containing molecule that comprises at least a portion of an immunoglobulin molecule, containing at least one complementarity determining region (CDR) of a heavy or light chain or a ligand binding portion thereof derived from a any of the monoclonal antibodies described herein, in combination with a heavy chain or light chain variable region, a heavy chain or light chain constant region, a framework region, or any portion thereof, of non-murine origin, preferably of human origin, which can be incorporated into an antibody of the present invention. Alternatively, the term "Anti-GD2 antibody" shall refer collectively or individually to hu3F8V1 IgGs with a single mutation, e.g. hu3F8V1-E1K, hu3F8V1-D32H, hu3F8V1-G54I; hu3F8V1 IgGs with a double mutation, e.g. hu3F8V1-E1KD32H, hu3F8V1-E1KG54I, and hu3F8V1-D32HG54I; hu3F8V1 IgGs with a triple mutation, e.g. hu3F8V1-E1KD32HG54I; hu3F8V5 IgG; hu3F8V5 IgGs with a single mutation, e.g. hu3F8V5-E1K, hu3F8V5-D32H, hu3F8V5-G54I; hu3F8V5 IgGs with a double mutation, e.g. hu3F8V5-E1KD32H, hu3F8V5-E1KG54I, and hu3F8V5-D32HG54I; and hu3F8V5 IgGs with a triple mutation, e.g. hu3F8V5-E1KD32HG54I antibodies, and combinations thereof, as well fragments and regions thereof such as single chain variable fragments of the present invention including hu3F8V1-E1K scFv, hu3F8V1-D32H scFv, hu3F8V1-G54I scFv; hu3F8V1 scFv with a double mutation, e.g. hu3F8V1-E1KD32H scFv, hu3F8V1-E1KG54I scFv, and hu3F8V1-D32HG54I scFv; hu3F8V1 scFv with a triple mutation, e.g. hu3F8V1-E1KD32HG54I scFv; hu3F8V5 scFv; hu3F8V5 scFv with a single mutation, e.g. hu3F8V5-E1K scFv, hu3F8V5-D32H scFv, hu3F8V5-G54I scFv; hu3F8V5 scFv with a double mutation, e.g. hu3F8V5-E1KD32H scFv, hu3F8V5-E1KG54I scFv, and hu3F8V5-D32HG54I scFv; hu3F8V5 scFv with a triple mutation, e.g. hu3F8V5-E1KD32HG54I scFv, and combinations thereof. Such antibody is capable of modulating, decreasing, antagonizing, mitigating, alleviating, blocking, inhibiting, abrogating and/or interfering with at least one cell function in vitro, in situ and/or in vivo, wherein said cell expresses GD2. As a non-limiting example, a suitable Anti-GD2 antibody, specified portion or variant of the present invention can bind with high affinity to an epitope of human GD2.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof, each containing at least one CDR derived from an Anti-GD2 antibody. Functional fragments include antigen-binding fragments that bind to a mammalian GD2. For example, antibody fragments capable of binding to GD2 or portions thereof, including, but not limited to Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

As used herein "chimeric" antibodies or "humanized" antibodies or "CDR-grafted" include any combination of the herein described Anti-GD2 Abs, or any CDR derived therefrom combined with one or more proteins or peptides derived from a non-murine, preferably, human antibody. In accordance with the invention, chimeric or humanized antibodies include those wherein the CDR's are derived from one or more of the Anti-GD2 Abs described herein and at least a portion, or the remainder of the antibody is derived from one or more human antibodies. Thus, the human part of the antibody may include the framework, CL, CH domains (e.g., CH1, CH2, CH3), hinge, (VL, VH)) regions which are substantially non-immunogenic in humans. The regions of the antibody that are derived from human antibodies need not have 100% identity with human antibodies. In a preferred embodiment, as many of the human amino acid residues as possible are retained in order for the immunogenicity to be negligible, but the human residues may be modified as necessary to support the antigen binding site formed by the CDR's while simultaneously maximizing the humanization of the antibody. Such changes or variations optionally and preferably retain or reduce the immunogenicity in humans or other species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about twenty glycine or other amino acid residues, preferably 8-15 glycine or other amino acid residues, which connects the variable region of the heavy chain and the variable region of the light chain. Such linker peptides are considered to be of human origin.

Antibody humanization can be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

Antibody Humanization can be used to evolve mouse or other non-human antibodies into "fully human" antibodies. The resulting antibody contains only human sequence and no mouse or non-human antibody sequence, while maintaining similar binding affinity and specificity as the starting antibody.

For full length antibody molecules, the immunoglobulin genes can be obtained from genomic DNA or mRNA of hybridoma cell lines. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

At least one Anti-GD2 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, antibodies, a Laboratory Manual, Cold Spring Harbor, N.Y. (1989). Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A), or the like, or heteromyelomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Antibodies of the present invention can also be prepared using at least one Anti-GD2 antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616, 5,565,362; 5,304,489, and the like, each of which is entirely incorporated herein by reference.

Antibodies of the present invention can additionally be prepared using at least one Anti-GD2 antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

An Anti-GD2 antibody can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified antibodies can be characterized by, for example, ELISA, ELISPOT, flow cytometry, immunocytology, BIA-CORE™ analysis, SAPIDYNE KINEXA™ kinetic exclusion assay, SDS-PAGE and Western blot, or by HPLC analysis as well as by a number of other functional assays disclosed herein.

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as DHFR, GPT, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

In accordance with the present invention, the Anti-GD2 antibodies comprise any one of hu3F8V1-E1K, hu3F8V1-D32H, hu3F8V1-G54I; hu3F8V1 with a double mutation, e.g. hu3F8V1-E1KD32H, hu3F8V1-E1KG54I, and hu3F8V1-D32HG54I; hu3F8V1 with a triple mutation, e.g. hu3F8V1-E1KD32HG54I; hu3F8V5 IgG; hu3F8V5 with a single mutation, e.g. hu3F8V5-E1K, hu3F8V5-D32H, hu3F8V5-G54I; hu3F8V5 with a double mutation, e.g. hu3F8V5-E1KD32H, hu3F8V5-E1KG54I, and hu3F8V5-D32HG54I; and hu3F8V5 IgGs with a triple mutation, e.g. hu3F8V5-E1KD32HG54I antibodies or an antibody in which the variable region or CDRs are derived from any one of hu3F8V1-E1K, hu3F8V1-D32H, hu3F8V1-G54I; hu3F8V1 with a double mutation, e.g. hu3F8V1-E1KD32H, hu3F8V1-E1KG54I, and hu3F8V1-D32HG54I; hu3F8V1 with a triple mutation, e.g. hu3F8V1-E1KD32HG54I; hu3F8V5 IgG; hu3F8V5 with a single mutation, e.g. hu3F8V5-E1K, hu3F8V5-D32H, hu3F8V5-G54I; hu3F8V5 with a double mutation, e.g. hu3F8V5-E1KD32H, hu3F8V5-E1KG54I, and hu3F8V5-D32HG54I; and hu3F8V5 with a triple mutation, e.g. hu3F8V5-E1KD32HG54I antibody and the framework and constant regions of the antibody are derived from one or more human antibodies. The variable region or CDRs derived from the antibody preferably have from about 90% to about 100% identity with the variable region or CDRs of any one of hu3F8V1-E1K, hu3F8V1-D32H, hu3F8V1-G54I; hu3F8V1 with a double mutation, e.g. hu3F8V1-E1KD32H, hu3F8V1-E1KG54I, and hu3F8V1-D32HG54I; hu3F8V1 with a triple mutation, e.g. hu3F8V1-E1KD32HG54I; hu3F8V5; hu3F8V5 with a single mutation, e.g. hu3F8V5-E1K, hu3F8V5-D32H, hu3F8V5-G54I; hu3F8V5 with a double mutation, e.g. hu3F8V5-E1KD32H, hu3F8V5-E1KG54I, and hu3F8V5-D32HG54I; and hu3F8V5 with a triple mutation, e.g. hu3F8V5-E1KD32HG54I although any and all modifications, including substitutions, insertions and deletions, either from natural mutation or from human manipulation are contemplated so long as the antibody maintains the ability to bind to GD2. The regions of the chimeric, humanized or CDR-grafted antibodies that are derived from human antibodies need not have 100% identity with the human antibodies. In a preferred embodiment, as many of the human amino acid residues as possible are retained in order that immunogenicity is negligible, but the human residues, in particular residues of the framework region, are substituted as required and as taught herein below in accordance with the present invention. Such modifications as disclosed herein are necessary to support the antigen binding site formed by the CDRs while simultaneously maximizing the humanization of the antibody.

Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given Anti-GD2 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an Anti-GD2 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least binding to GD2. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255: 306-312 (1992)).

An Anti-GD2 antibody can further optionally comprise a polypeptide of at least one of 70-100% of the contiguous amino acids of the CDRs derived from at least one of sequence described herein.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of at least one sequence in Tables 1-4.

Exemplary heavy chain and light chain variable regions sequences are provided herein. The antibodies of the present invention, or specified variants thereof, can comprise any number of contiguous amino acid residues from an antibody of the present invention, wherein that number is selected from the group of integers consisting of from 10-100% of the number of contiguous residues in an Anti-GD2 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

In accordance with the present invention, the nucleic acid sequences set forth in SEQ ID NOs: 32-45 and the deduced amino acid sequences of the Anti-GD2 antibodies are set forth in SEQ ID NOs:1-31. Each of the heavy and light chain variable regions contain three CDRs that combine to form the antigen binding site. The three CDRs are surrounded by four framework regions that primarily function to support the CDRs. The sequences of the CDRs within the sequences of the variable regions of the heavy and light chains can be identified by computer-assisted alignment according to Kabat et al. (1987) in Sequences of Proteins of Immunological Interest, 4th ed., United States Department of Health and Human Services, U.S. Government Printing Office, Washington, D.C., or by molecular modeling of the variable regions, for example utilizing the ENCAD program as described by Levitt (1983) J. Mol. Biol. 168:595.

Human genes which encode the constant (C) regions of the humanized antibodies, fragments and regions of the present invention can be derived from a human fetal liver library, by known methods. Human C region genes can be derived from any human cell including those which express and produce human immunoglobulins. The human CH region can be derived from any of the known classes or isotypes of human H chains, including gamma, mu, alpha, delta, epsilon, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the CH region is derived from gamma 1 (IgG1) or gamma 4 (IgG4).

The human CL region can be derived from either human L chain isotype, kappa or lambda, preferably kappa.

Genes encoding human immunoglobulin C regions are obtained from human cells by standard cloning techniques (Sambrook, et al. (Molecular Cloning: A Laboratory Manual, 2.sup.nd Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof.

The sequences of the variable regions of the antibody may be modified by insertions, substitutions and deletions to the extent that the chimeric antibody maintains the ability to bind to human GD2. The ordinarily skilled artisan can ascertain the maintenance of this activity by performing the functional assays described hereinbelow. The variable regions can have, for example, from about 50% to about 100% homology to the variable regions identified below. In a preferred embodiment, the variable regions of the antibody have from about 80% to about 100% homology to the variable regions identified below. In a more preferred embodiment the variable regions have from about 90% to about 100% homology to the variable regions identified below.

In one specific aspect, preferred Anti-GD2 Mabs of the disclosure comprise variable light chain regions having 95%, 96%, 97%, 98% or 99% amino acid sequence homology to sequences identified herein and further comprise variable heavy chain regions having 95%, 96%, 97%, 98% or 99% amino acid sequence homology to sequences in identified herein.

Preferably, the antibody or antigen-binding fragment of an antibody or specified portion or variant thereof of the present invention binds human GD2 and, thereby partially or substantially neutralizes one GD2 protein or fragment and thereby inhibit activities mediated through GD2. As used herein, the term "neutralizing antibody" refers to an antibody that can inhibit GD2 dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an Anti-GD2 antibody to inhibit a GD2-dependent activity is preferably assessed by at least one suitable assay, as described herein and/or as known in the art.

As stated, the invention also relates to antibodies, antigen-binding fragments, immunoglobulin chains and CDRs comprising amino acids in a sequence that is substantially the same as an amino acid sequence described herein. Such Anti-GD2 antibodies can include one or more amino acid substitutions, deletions or additions, either from natural mutations or human manipulation, as specified herein. Preferably, such antibodies or antigen-binding fragments and antibodies comprising such chains or CDRs can bind human GD2 with high affinity.

As those of skill in the art will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group.

In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane, e.g. polylysine. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate, n-tetradecanoate, n-octadecanoate, n-eicosanoate, n-docosanoate, n-triacontanoate, n-tetracontanoate, cis-.delta.9-octadecanoate, all cis-.delta.5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetraethylene glycol, —(CH2)3-, —NH—, to name a few. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

The antibodies of the invention can bind human GD2 with a wide range of affinities ($K_D$) as shown below.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters are preferably made with standardized solutions of antibody and antigen, and a standardized buffer, such as the buffer described herein.

Anti-GD2 antibodies useful in the methods and compositions of the present invention are characterized by binding to GD2 and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (Elliott et al., Lancet 344:1125-1127 (1994), entirely incorporated herein by reference).

Bispecific, heterospecific, heteroconjugate or similar antibodies can also be used that are monoclonal, humanized, antibodies that have binding specificities for at least two different antigens. In the present case, one of the binding specificities is for at least one GD2 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986); Chan and Carter, 2010, Nature Rev. 10, 301-316; Weiner et al., 2010, Nature Rev. 10, 317-327; each entirely incorporated herein by reference.

In certain embodiments, the antibodies, that bind to GD2 can be used in unconjugated form. In other embodiments, the antibodies that bind to GD2 can be conjugated, e.g., to a detectable label, a drug, a prodrug or an isotope.

In certain methods of the invention described in more detail below, such as methods of detecting GD2 expression in cells or tissues as a measure of the metastatic potential of tumor cells, or as a way of identifying in situ carcinomas (e.g., DCIS or LCIS) in tissues, the Anti-GD2 antibodies are conjugated to one or more detectable labels. For such uses, antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid.

Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include 3H, 111In, 125I, 131I, 32P, 35S, 14C, 51Cr, 57To, 58Co, 59Fe, 75Se, 152Eu, 90Y, 67Cu, 217Ci, 211At, 212Pb, 47Sc, 109Pd, etc. 111In is a preferred isotope where in vivo imaging is used since its avoids the problem of dehalogenation of the 125I or 131I-labeled GD2-binding antibodies by the liver. In addition, this radionucleotide has a more favorable gamma emission energy for imaging (Perkins et al, Eur. J. Nucl. Med. 70:296-301 (1985); Carasquillo et ah, J. Nucl. Med. 25:281-287 (1987)). For example, 111In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Examples of suitable non-radioactive isotopic labels include 157Gd, 55Mn, 162Dy, 52Tr, and 56Fe.

Examples of suitable fluorescent labels include an 152Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to Anti-GD2 antibodies, are provided by Kennedy et at., Clin. CMm. Acta 70:1-31 (1976), and Schurs et al, Clin. CMm. Acta 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

For use in certain therapeutic approaches of the invention such as ablation of residual tumor cells following surgery, or prevention of metastasis, the Anti-GD2 antibodies can be conjugated to one or more drugs, prodrugs or isotopes. Preferred such conjugates comprise one or more ligands, e.g., one or more antibodies or fragments, derivatives or variants thereof, that bind to GD2, conjugated to one or more cytotoxic agents; such conjugates are useful in the methods of treatment and prevention of tumor metastasis provided by the invention. According to certain such embodiments of the invention, the Anti-GD2 antibody, is conjugated to a cytotoxic agent. Cytotoxic, e.g., chemotherapeutic, agents useful in the generation of Anti-GD2 antibody-cytotoxic agent conjugates are well known in the art, and include but are not limited to cisplatin, carboplatin, oxaliplatin, paclitaxel, melphalan, doxorubicin, methotrexate, 5-fluorouracil, etoposide, mechlorethamine, cyclophosphamide, bleomycin, microtubule poisons, and annonaceous acetogenins. Other chemotherapeutic agents suitable' for use in accordance with this aspect of the invention are well-known and will be familiar to the ordinarily skilled artisan.

The use of conjugates of one or more Anti-GD2 antibody, and one or more small molecule toxins, such as a calicheamicin, a maytansine (U.S. Pat. No. 5,208,020), a trichothene, and CC1065, are also contemplated herein. In one embodiment of the invention, the Anti-GD2 antibody is conjugated to one or more maytansine molecules (e.g. about 1 to about 10 maytansine molecules per Anti-GD2 antibody). Maytansine may, for example, be converted to May-SS-Me which may be reduced to May-SH3 and reacted with modified Anti-GD2 antibody (Chari et al. Cancer Research 52: 127-131 (1992)) to generate a maytansinoid-Anti-GD2 antibody conjugate.

Alternatively, the Anti-GD2 antibody can be conjugated to one or more calicheamicin molecules. The calicheamicin family of antibiotics are capable of producing double-stranded DNA breaks at sub-picomolar concentrations. Structural analogues of calicheamicin which may be used (Hinman et al. Cancer Research 53: 3336-3342 (1993) and Lode et al. Cancer Research 58: 2925-2928 (1998)).

Enzymatically active toxins and fragments thereof which can be used to produce conjugates with one or more Anti-GD2 antibody, include diphtheria A chain, nonbinding active fragments of diphtheria toxin, exotoxin A chain (from *Pseudomonas aeruginosa*), ricin A chain, abrin A chain, modeccin A chain, alpha-sarcin, Aleuritesfordii proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published in the English language on Oct. 28, 1993, the disclosure of which is incorporated herein by reference in its entirety. Mytansinoids may also be conjugated to one or more Anti-GD2 antibody.

The present invention further contemplates Anti-GD2 antibody conjugated with a compound with nucleolytic activity (e.g., a ribonuclease or a DNA endonuclease such as a deoxyribonuclease; DNase).

Exemplary Alternative Formats

In some particular embodiments, provided Anti-GD2 antibody agents, or sequences thereof, are utilized in multispecific (e.g., bispecific) formats. In some embodiments, bspecific MoAb may be comprised of dual variable domains, with one domain having anti-3F8 variable domain and the other domain chosen from a group consisting of anti-OKT3 for retargeting T cells for tumor cytotoxicity, or DOTA-metal, C8.2.5 for multistep pretargeting, or Clone 35, CD137, for ADCC with anti-41BB-scFv as agonist, or with CD137, 41BBL for ADC with 41 BBL as agonist. A N297A mutation in the CH2 domain results in aglycosylation leading to no FcR or Clq binding. The amino acid sequence of (hu3F8V1-scFv)-(huOKT3-scFv) with linker and spacer is shown in SEQ ID NO:29, and without spacer in SEQ ID NO:30. The amino acid sequence of hu3F8V1 scFv)-(C8.2.5-scFv) (based on Orcutt et al., 2010, Protein Eng Design and Selection 23, 221) is shown in SEQ ID NO:31.

Bispecific antibody (anti-GD2 and anti-DOTA) can be used in a first step of a multistep pretargeting, followed by blood clearance using DOTA(metal)-Dextran as clearing agent, with a third step introducing DOTA(metal)-conjugated therapeutics such as DOTA(metal)-radioactive metal, DOTA(metal)-nanoparticles, DOTA(metal-liposomes, DOTA(metal)-drugs, DOTA(metal)-DNA, DOTA(metal)-RNA, and DOTA (metal)-toxins. Since C8.2.5 has different affinities for each type of DOTA-metal comples, the affinity of the pretargeted C8.2.5 for the clearing agent and the DOTA-ligand can be precisely controlled.

The amino acid sequence of hu3F8 and its variants presented herein, can be used to construct chimeric antigen receptor (CAR) as was previously shown for other anti-GD2 antibodies (Krause et al., 1998, J Exp Med 188, 619-626). The CAR strategy of retargeting immune effector cells is independent of the MHC-peptide-TCR interaction and allows cells to react against a large variety of cell surface antigens (Davies and Maher, 2010, Achivum immunologiae et therapiae experimentalis 58, 165-178). Several methods have been used in the design of CARs, with most of them employing the antigen binding domain of a monoclonal antibody in the form of a single-chain variable fragment (scFv) for antigen recognition. The initial T cell activating receptors originated from studies which allowed researchers to elucidate the role of the CD3ζ chain (Irving and Weiss, 1991, Cell 64, 891-901; Romeo et al., 1992, Cell 68, 889-897). In subsequent studies, scFvs of interest were fused to the CD3ζ chain (Eshhar et al., 1993, PNAS USA 90, 720-724) or FcεRIγ (Weijtens et al., 1996, J Immunol 157, 836-843), and both were found to be sufficient for T cell activation. While this laid the blueprint for CAR construction, the incorporation of costimulatory molecules came about after it was found that first generation CARs were able to induce T cell proliferation only up to 2-3 cell divisions, followed rapidly by cell death (Gong et al., 1999, Neoplasia 1, 123-127). By expressing CD80 on the target tumor cell, researchers were able to show that CAR expressing cells could be restimulated, leading to further increases in T cell numbers. The first CARs which incorporated the CD28 costimulatory molecule alongside the CD3ζ chain showed vast improvements over those which expressed the CD3ζ chain alone (Krause et al., 1998, supra; Haynes et al., 2002, Blood 100, 3155-3163; Maher et al., 2002, Nature Biotech 20, 70-75); this included an absolute increase in T cell numbers as well as an increase in IL-2 production. Since then, several other groups began to use other costimulatory molecules, either in combination with CD3ζ alone or with both CD3ζ and CD28. These additional signaling molecules include 4-1BB (Wang et al., 2007, Human Gene Ther 18, 712-725; Brentjens et al., 2007, Clin Cncer Res 13, 5426-5432; Imai et al., 2004, Leukemia 18, 676-684; Finney et al., 2004, J Immunol 172, 104-113), DAP10 (Brentjens et al., 2007, supra), OX40 (Brentjens et al., 2007, supra; Finney et al., 2004, supra; Wilkie et al., 2008, J Immunol 180, 4901-4909; Nguyen and Geiger, 2003, Gene Therapy 10, 594-604; Pule et al., 2005, Mol Ther 12, 933-941) and ICOS (Finney et al., 2004, supra), and have been applied in the context of T cells as well as NK cells (Daldrup-Link et al., 2005, Eropean radiology 15, 4-13; Imai and Campana, 2004, J Biol Reg Homeostatic Ag 18, 62-71; Roberts et al., 1998, J Immunol 375-384; Kruschinski et al., 2008, PNAS USA 105, 17481-17486; Pegram et al., 2008, J Immunol 181, 3449-3455). While first generation CARs are the only ones which have been tested in the clinic up to this point, both in vitro and in vivo comparisons have demonstrated a clear superiority with second and third generation CARs (Haynes et al., 2002, supra; Brentjens et al., 2007, supra; Teng et al., 2004, Human Gene Ther 15, 699-708; Haynes et al., 2002, J Immunol 169, 5780-5786; Kowolik et al., 2006, Cancer Res 66, 10995-11004; Loskog et al., 2006, Leukemia 20, 1819-1928; Moeller et al., 2004, Cancer Gene Therapy 11, 371-379; Vera et al., 2006, Blood 108, 3890-3897).

Currently, most researchers use bulk human peripheral T cells, however others have recently began to use EBVspecific T cells (Rossig et al., 2002, Blood 99, 2009-2016), lymphoid progenitor cells (Zakrzewski et al., 2006, Nature Med 12, 1039-1047; Zakrzewski et al., 2008, Nature Biotech 26, 453-461), and unfractionated bone marrow cells (Papapetrou et al., 2009, J clin Invest 119, 157-168; Wang et al., 1998, Nature Med 4, 168-172). Killer leukemia cell lines (e.g. NK92, NK92MI, KHYG-1) that are cytolytic and easy to culture can also provide a continuous supply of CAR expressing effector cells for pre-clinical and clinical testing. NK92MI is a human NK cell line derived from a non-Hodgkin's lymphoma and transduced with human IL-2 cDNA; previous studies have demonstrated its strong cytotoxic abilities in mouse models (Tam et al., 1999, J Hematol 8, 281-290; Korbelik and Sun, 2001, Inter J Cancer 93, 269-274). In addition, NK92 cells have also been used in the clinical setting and proven safe after a number of Phase I studies in patients with renal cell carcinoma and melanoma (Arai et al., 2008, Cytotherapy 10, 625-632). Because of their ease of maintenance in vitro and relatively short doubling-times, these cells are ideal effectors for various cytotoxicity assays to test a variety of targeting approaches. While studies using the original IL-2-dependent NK92 cell line have shown minimal toxicities in both mice and humans, the IL-2-transduced NK92MI cells may have a greater leukemogenic potential. One method by which researchers try and avoid leukemogenesis in SCID mice using NK92 cells is by irradiating the effectors with 3000 cGy before inoculation. In phase I clinical trials, this is sufficient in preventing NK92MI cells from proliferating uncontrollably inside of the immunocompromised patient. An alternative safety mechanism is that which involves the employment of suicide genes. One common example is the use of the herpesvirus thymidine kinase gene, which works by killing a cell which expresses the gene by administration of acyclovir or ganciclovir (Helene et al., 1997, J Immunol 5079-5082).

Nucleic Acids

The nucleotide and amino acid sequence of the heavy and light chain variable regions of the MoAbs of the invention are described in this application. The invention further provides polynucleotides comprising a nucleotide sequence encoding an antibody of the invention and fragments thereof. The invention also encompasses polynucleotides that hybridize under stringent or lower stringency hybridization conditions to polynucleotides that encode an antibody of the present invention.

The polynucleotides may now be obtained by any method known in the art. For example, since the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Since the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules comprising the coding sequence for an Anti-GD2 antibody or variable region; and nucleic acid molecules which comprise a nucleotide sequence substantially different from those described above but which, due to the degeneracy of the genetic code, still encode at least one Anti-GD2 antibody as described herein and/or as known in the art.

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

A vector comprising any of the above-described isolated or purified nucleic acid molecules, or fragments thereof, is further provided by the present invention. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. For example, a cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI110, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or nonnative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Optionally, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, e.g., Gateway® (Invitrogen)). See, also, U.S. Pat. No. 5,314,995.

In view of the foregoing, the present invention also provides a composition comprising an above-described isolated or purified nucleic acid molecule, optionally in the form of a vector. The composition can comprise other components as described further herein.

isotopes are also available for the production of radio-conjugated Anti-GD2 antibody for use in therapeutic methods of the invention. Examples include 211At, 131I, 125I, 90Y, 186Re, 188Re, 153Sm, 212Bi, 32P and radioactive isotopes of Lu.

Conjugates of the Anti-GD2 antibody and cytotoxic agents may be made using a variety of bifunctional protein coupling agents such as N-succinimidyl-3-(2-pyridyldithiol) propionate (SPDP), succinimidyl-4-(N-maleimidomethyl) cyclohexane-I-carboxylate, iminothiolane (IT), bifunctional derivatives of imidoesters (such as dimethyl adipimidate HCl), active esters (such as disuccinimidyl suberate), aldehydes (such as glutaraldehyde), his-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). 14Carbon-labeled 1-isothiocyanatobenzyl-3-methyldiethylene triaminepentaacetic acid (MX-DTPA) is an exemplary chelating agent for conjugation of radionucleotide to the Anti-GD2 antibody. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52:127-131 (1992)) may be used.

Alternatively, a fusion protein comprising the Anti-GD2 antibody ligand and cytotoxic agent may be made, e.g. by recombinant techniques or peptide synthesis.

Compositions

Anti-GD2 antibody compositions of the present invention include any suitable and effective amount of a composition or pharmaceutical composition comprising at least one Anti-GD2 antibody agent, for use in delivering the provided antibody agent to a cell, tissue, organ, animal or patient in need of such modulation, treatment or therapy.

The present invention also provides at least one Anti-GD2 antibody composition comprising at least one, at least two, at least three, at least four, at least five, at least six or more Anti-GD2 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the Anti-GD2 antibody amino acid sequence selected from the group consisting of 70-100% of the contiguous amino acids of the CDR regions of the antibodies described herein, or specified fragments, domains or variants thereof. Preferred Anti-GD2 antibody compositions include at least one or two full length, fragments, domains or variants as at least one CDR or LBR containing portions of the Anti-GD2 antibody sequences described herein. Further preferred compositions comprise 40-99% of at least one of 70-100% of a CDR region of an Anti-GD2 Ab described herein. Such composition percentages are by weight, volume, concentration, molarity, or molality as liquid or dry solutions, mixtures, suspension, emulsions or colloids, as known in the art or as described herein.

Anti-GD2 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18$^{th}$ Edition, Mack Publishing Co. (Easton, Pa.) 1990. Pharmaceutically acceptable carriers can be routinely selected that are suitable for the mode of administration, solubility and/or stability of the Anti-GD2 antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-GD2 antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, Anti-GD2 antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the Anti-GD2 antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one Anti-GD2 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one Anti-GD2 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one Anti-GD2 antibody, and a second vial comprising an aqueous diluent of prescribed buffer or preservative, wherein said packaging material comprises a label that instructs a patient to reconstitute the at least one Anti-GD2 antibody in the aqueous diluent to form a solution that can be held over a period of twenty-four hours or greater.

The range of at least one Anti-GD2 antibody in the product of the present invention includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, PLURONIC® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one Anti-GD2 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one Anti-GD2 antibody and preservative in an aqueous diluent is carried out using conventional dissolution and mixing procedures. To prepare a suitable formulation, for example, a measured amount of at least one Anti-GD2 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one Anti-GD2 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one Anti-GD2 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one Anti-GD2 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one Anti-GD2 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD AUTOJECTOR®, HUMAJECT®, e.g., as made or developed by Becton Dickensen (Franklin Lakes, N.J.), Disetronic (Burgdorf, Switzerland; Bioject, Portland, Oreg.; National Medical Products, Weston Medical (Peterborough, UK), Medi-Ject Corp (Minneapolis, Minn.). Recognized devices comprising a dual vial system include those pen-injector systems for reconstituting a lyophilized drug in a cartridge for delivery of the reconstituted solution such as the HUMATROPEN®.

The products presently claimed include packaging material. The packaging material provides, in addition to the information required by the regulatory agencies, the conditions under which the product can be used. The packaging material of the present invention provides instructions to the patient to reconstitute the at least one Anti-GD2 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one Anti-GD2 antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one Anti-GD2 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one Anti-GD2 antibody in either the stable or presented formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

In one embodiment of the present invention, the pharmaceutical compositions comprising an anti-GD2 antibody of the disclosure facilitate administration of humanized antibodies to an organism, preferably an animal, preferably a mammal Particular mammals include bovine, canine, equine, feline, ovine, and porcine animals, non-human primates, and humans. Humans are particularly preferred.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Combination Therapy

In some embodiments, provided Anti-GD2 antibodies are administered, optionally further comprising at least one selected from at least one TNF antagonist (e.g., but not limited to a TNF antibody or fragment a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist, and cell therapies. Non-limiting examples of such cytokines include, but are not limited to, any of IL-1 to IL-34. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157: H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella* cholera-suis, *Salmonella enteritidis*), *Clostridium* species (e.g., *Clostridium perfringens. Clostridium difficile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, N.Y. (1990); Berkow et al, eds., The Merck Manual, 16th edition, Merck and Co., Rahway, N. J., 1992; Wood et al, FEMS Microbiology Immunology, 76:121-134 (1991); Marrack et al, Science, 248:705-711 (1990), the contents of which references are incorporated entirely herein by reference.

Production

The at least one Anti-GD2 antibody used in accordance with the present invention can be produced by recombinant means, including from mammalian cell or transgenic preparations, or can be purified from other biological sources, as described herein or as known in the art.

Also in view of the above, the present invention provides a host cell comprising an above-described isolated or purified nucleic acid molecule, optionally in the form of a vector. It is most preferable that the cell of the present invention expresses the vector, such that the oligonucleotide, or fragment thereof, is both transcribed and translated efficiently by the cell. Examples of cells include, but are not limited to, a human cell, a human cell line, *E. coli* (e.g., *E. coli* TB-1, TG-2, DH5α, XL-Blue MRF' (Stratagene), SA2821 and Y1090), *B. subtilis, P. aerugenosa, S. cerevisiae, N. crassa*, insect cells (e.g., Sf9, Ea4) and others set forth herein below. The host cell can be present in a host, which can be an animal, such as a mammal, in particular a human.

In a specific embodiment, using routine recombinant DNA techniques, one or more of the CDRs identified herein may be inserted within framework regions. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds GD2. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Applications

A high affinity, neutralizing chimeric or human antibody to GD2 would be desirable to be used in diseases where GD2 is expressed, for example, GD2 is expressed in >50% of melanoma (Zhang et al., 1997, Int. J. Cancer. 73, 42-49), 88% of osteosarcoma (Heiner et al., 1987, Cancer Res. 47, 5377-5388), and 93% of soft tissue sarcomas including liposarcoma, fibrosarcoma, malignant fibrous histiocytoma, leiomyosarcoma, and spindle cell sarcoma (Chang et al., 1992, Cancer 70, 633-638), as well as brain tumors (Longee et al., 1991, Acta Neuropathol. 82, 45-54). Anti-GD2 antibodies have been tested in patients with melanoma (Saleh et al, 1992, Hum. Antibodies Hybridomas 3, 19-24; Cheung et al., 1987, J. Clin. Oncol. 5, 1430-1440; Choi et al., 2006, Cancer Immunol. Immunother. 55, 761-774), sarcomas (Choi et al., 2006, supra; Yeh et al., 1992, The fifth Asia and Oceania Congress of Nuclear Medicine and Biology Proceedings, p. 104), small cell lung cancer (Grant et al., 1996, Eur. J. Nucl. Med. 23, 145-149), brain tumors (Arbit et al., 1995, Eur. J. Nucl. Med. 22, 419-426), by iv injection as well as by compartmental therapy using Ommaya reservoirs (Kramer et al., 2007, J. Clin. Oncol. 25, 5465-5470). GD2 is also a tumor target for retinoblastoma (Chantada et al., 2006, J. Pediatr. Hematol. Oncol. 28, 369-373) and HTLV-1 infected T cells leukemia cells (Furukawa et al., 1993, PNAS USA 90, 1972-1976). In one preferred aspect, an Anti-GD2 antibody of the disclosure can be used to treat neuroblastoma. Anti-GD2 antibodies or derivatives thereof can be used either as a single agent or in combination with other therapeutic agents. In addition, these Mabs can be used as a chemosensitizer whereby their use can increase therapeutic efficacy of cytotoxic agents. These antibodies can be used as a radiosensitizer whereby their use can improve efficacy of radiation. They can also be used in combination with other tumor-immunomodulating agents such as IL-2, IL-12 and/or IFNalpha. Additionally, the Anti-GD2 antibodies can be used in combination with other monoclonal antibodies such as anti-TNF-alpha, IL-12/IL-23, IL-2, GpIIb/IIIa receptor, CD52, CD20, RSV proteins, HER2/neu receptor, and the like; as well as with commercially approved antibodies including Rituxan, Herceptin, Mylotarg, Campath, Zevalin, Bexxar, Erbitux, Avastin and Vectibix.

Thus, the present invention also provides a method for modulating or treating at least one GD2 related disease, in a cell, tissue, organ, animal, or patient, as known in the art or as described herein, using at least one Anti-GD2 antibody of the present invention.

Adoptive immunotherapy trials in 1986 using lymphokine-activated killer cells (LAK) and tumor infiltrating lymphocytes (TIL) reported occasional tumor responses in patients. Donor lymphocyte infusions have shown even more successes in patients with chronic myelogenous leukemia following allogeneic stem cell transplant or in patients with post-transplant EBV-associated lymphoproliferative disease (PTLD). In solid tumors, CTL was successful in treating malignant melanoma during the lymphopenic phase created by high dose chemotherapy. Bispecific antibodies are made by fusing two hybridomas to create hybrid immunoglobulin molecules with two binding sites. The antibodies not only handcuff tumors to T-cells; they cross-link CD3 on T-cells and initiate the activation cascade. This way, TCR-based cytotoxicity is redirected to desired tumor targets bypassing MHC restrictions. Arming of polyclonally activated T cells (ATC) with anti-CD3× anti-TAA (BsAb or BiTE antibody) combines the targeting specificity of MoAb (e.g. hu3F8 where TAA is GD2) with the non-MHC-restricted perforin/granzyme mediated cytotoxicity of T cells. BsAb or BiTE can arm ex vivo expanded activated T cells before infusion into a patient. This strategy converts every ATC into a specific CTL (Thakur and Lum, 2010, Curr Opin Mol Ther 12, 340-349; Grabert et al., 2006, Clin Cancer Res 12, 569-576).

Tumors evade T cells by a number of mechanisms: low or no expression of MHC (e.g. in NB), derailing T cell signaling, decreased presentation of tumor peptides on MHC, absence of co-stimulatory molecules, and induction of regulatory T-cells that inhibit CTL and humoral responses. Since the killing carried out by BsAb or BiTE armed ATC is non-MHC-restricted, this strategy should overcome some of these tumor escape mechanisms. Tumors secrete TGF-β shifting the T-cell immune response to a Th2 type, down-regulating interleukin 2 (IL-2) and IFN-γ secretion, while upregulating IL-10 and IL-6, all leading to immune suppression. T-cells redirected by BsAb or BiTE may bypass these negative effects of regulatory cytokines, since armed ATC lyse tumor targets in an IL-2 independent manner. Patients treated with BsAb or BiTE armed T cells directed at their tumors have increased levels of TNF-α and IFN-γ, which should shift the T-cells towards a Th1 response. In addition, cytotoxic T cells kill through their Fas ligand (FasL) that engage Fas receptors (CD95) on tumor cells. Unfortunately, FasL on tumors cells can also induce apoptosis of T cells. TCR stimulation through CD3 cascade protects CD8+ cells from CD95-mediated suicide. Armed ATC resist CD95-induced cell death through crosslinking of the TCR with BsAb or BiTE. The ability of T-cells to kill serially, i.e. one T-cell killing consecutive tumor targets, proliferate during the process, and move into lymphatics and soft tissues increased the chance of catching NB cells while they metastasize out of the marrow space to form tumor masses. Recent studies using BsAb or BiTE targeting human cancers have shown promise.

There is mounting evidence, particularly from analyses of patients who have received allogenic hematopoietic cell transplants, supporting the potential of T-cells to suppress or eradicate lymphomas and certain forms of leukemia (O'reilly et al., 2010, Semin Immunol 22, 162-172). However, there are no convincing data supporting a role for T-cells in the control of solid tumors in children. This is consistent with the fact that several of these tumors either do not express inherited class I or II HLA alleles (e.g. neuroblastoma) (Raffaghello et al., 2005, Oncogene 24, 4634-4644; Wolfl et al., 2005, Cancer Immunol Immunother 54, 400-406) or express only class I alleles and at low levels (e.g. rhabdomyosarcomas) (Prados et al., 2006, Neoplasma 53, 226-231). Furthermore, expression of critical costimulatory molecules such as B7.1 and ICAM-1 is often low or undetectable. As a result, the capacity of these tumors to elicit T-cell responses is poor and the potential of effector T-cells to engage the tumors through T-cell receptor by binding tumor antigens presented by HLA alleles is limited. Furthermore, the most effective therapies currently available for neuroblastoma, rhabdomyosarcoma, Ewing's sarcoma and desmoplastic small round cell tumors employ immunosuppressive alkylating agents, particularly cyclophosphamide at doses inducing profound T-lymphopenia. Bifunctional antibodies permit the targeted engagement of T-cells and exploitation of their effector functions through HLA-non-restricted CD3-mediated activation rather than their antigen-specific HLA-restricted TCRs. Studies of certain bifunctional monoclonal antibodies specific for CD3 and a tumor antigen such as CD-19, HER-2 NEU, or CEA have demonstrated the capacity of these antibodies to link cytotoxic T-cells to tumor cells expressing the other targeted antigen (Bargou et al., 2008, Science 321, 974-977; Topp et al., 2009, Blood (ASH Annual Meeting Abstracts) 114, 840; Kiewe et al., 2006, Clin Cancer Res 12, 3085-3091; Lutterbuese et al., 2009, J Immnother 32, 341-352). Once both antibody receptors are engaged, a cytotoxic T-cell response is initiated against the tumor cells. The T-cell response involves formation of a cytotoxic synapse between the T-cell receptor and the tumor cell as well as perforin and granzyme mediated induction of tumor cell apoptosis (Offner et al., 2006, Mol Immunol 43, 763-771; Brischwein et al., 2006, Mol Immunol 43, 1129-1143). Engagement of CD3 also activates the T-cells, inducing proliferation and generation of effector cytokines that potentiate the antitumor effect (Brischwein et al., 2006, supra; Brischwein et al., 2007, J Immunother 30, 798-807). Strikingly, the activated T-cells upregulate an anti-apoptotic protein c-FLIP which protects them from the cytotoxic effects of TNF and Fas ligand generated during T-cell activation (Dreir et al., 2002, Int J Cancer 100, 690-697). As a result, the T-cell response is magnified. As a consequence, picogram levels of the bifunctional antibody can exert significant antitumor effects in vitro (Lutterbuese et al., 2009, supra; Brandl et al., 2007, Cancer Immunol Immunother 56, 1551-1563) and in vivo, as shown in preclinical animal models and particularly in the results of initial clinical trials of the CD3/CD19 bispecific in the treatment of B-cell lymphomas and ALL (Topp et al., 2009, supra; Kiewe et al., 2006, supra). It has been hypothesized that the T-cell responses induced can also recruit naïve T-cells and stimulate the generation of tumor-specific T-cells at tumor sites (Koehne et al., 2002, Blood 99, 1730-1740). Bispecific antibodies can also be used to retarget other effector cells besides T-lymphocytes. These effector cells include NK cells, B-lymphocytes, dendritic cells, monocytes, macrophages, neutrophils, mesenchymal stem cells, neural stem cells and other stem cells to cells, tissues or organs that express GD2. When the tissue is tumor, these effector cells can be exploited to kill or to deposit proteins (e.g. cytokines, antibodies, enzymes, or toxins), radioactive isotopes for diagnosis or for therapy. When the tissue is a normal organ, the effector cells can be similarly exploited to deliver proteins or isotopes for diagnosis or for therapy.

The present invention includes a method for modulating or treating at least one malignant disease in a cell, tissue, organ, animal or patient, including, but not limited to, at least one of: multiple myeloma, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, renal cell carcinoma, pancreatic carcinoma, prostatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia; and the treatment of inflammatory diseases such as mesangial proliferative glomerulonephritis and the like. Such a method can optionally be used in combination with, by administering before, concurrently or after administration of such GD2 antibody, radiation therapy, an anti-angiogenic agent, a chemotherapeutic agent, a farnesyl transferase inhibitor or the like.

The present invention also provides a method for modulating or treating at least one GD2 mediated immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, hone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited to asthenia, anemia, cachexia, and the like), chronic salicylate intoxication, sleep apnea, obesity, heart failure, sinusitis, inflammatory bowel disease, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, *E. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, and the like;

Any of such methods can optionally comprise administering an effective amount of at least one composition or pharmaceutical composition comprising at least one Anti-GD2 antibody to a cell, tissue, organ, animal or patient in need of such modulation, treatment or therapy.

Any method of the present invention can comprise administering an effective amount of a composition or pharmaceutical composition comprising at least one Anti-GD2 antibody to a cell, tissue, organ, animal or patient in need of such modulation, treatment or therapy. Such a method can optionally further comprise co-administration or combination therapy for treating such immune diseases or malignant diseases, wherein the administering of said at least one Anti-GD2 antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an IL-18 antibody or fragment, small molecule IL-18 antagonist or IL-18 receptor binding protein, an IL-1 antibody (including both IL-1 alpha and IL-1 beta) or fragment, a soluble IL-1 receptor antagonist, an antirheumatic (e.g., methotrexate, auranofin, aurothioglucose, azathioprine, etanercept, gold sodium thiomalate, hydroxychloroquine sulfate, leflunomide, sulfasalazine, radiation therapy, an anti-angiogenic agent, a chemotherapeutic agent, Thalidomidea muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which is entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

Any method of the present invention can comprise a method for treating a GD2 mediated disorder or a disorder characterized by GD2 expression, comprising administering an effective amount of a composition or pharmaceutical composition comprising at least one Anti-GD2 antibody to a cell, tissue, organ, animal or patient in need of such modulation, treatment or therapy. Such a method can optionally further comprise co-administration or combination therapy for treating such immune diseases, wherein the administering of said at least one Anti-GD2 antibody, specified portion or variant thereof, further comprises administering, before concurrently, and/or after, at least one agent as described above.

Typically, treatment of pathologic conditions is effected by administering an effective amount or dosage of at least one Anti-GD2 antibody composition that total, on average, a range from at least about 0.01 to 500 milligrams of at least one Anti-GD2 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 ug/ml serum concentration per single or multiple administration. Suitable dosages are known to medical practitioners and will, of course, depend upon the particular disease state, specific activity of the composition being administered, and the particular patient undergoing treatment in some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 1.6, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000·mu·g/ml serum concentration per single or multiple administration, or any range, value or fraction thereof Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

The invention further relates to the administration of at least one Anti-GD2 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intraocular, intravitreous, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one Anti-GD2 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90, Marcel Dekker, Inc. New York 1994, entirely incorporated herein by reference), or with oxidizing agents that enable the application of formulations containing proteins and peptides onto the skin (WO 98/53 847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

For pulmonary administration, preferably at least one Anti-GD2 antibody composition is delivered in a particle size effective for reaching the lower airways of the lung or sinuses. According to the invention, at least one Anti-GD2 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., WO 94/16970, WO 98/35888). Dry powder inhalers like TURBUHALER™ (Astra), ROTAHALER® (Glaxo), DISKUS®(Glaxo), devices marketed by Inhale Therapeutics, to name a few, use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like the ULTRAVENT® nebulizer (Mallinckrodt), and the ACORN II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one Anti-GD2 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g. less than about 10 um, preferably about 1-5 um, for good respirability.

A spray including GD2 antibody composition protein can be produced by forcing a suspension or solution of at least one Anti-GD2 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one Anti-GD2 antibody composition protein delivered by a sprayer have a particle size less than about 10 um, preferably in the range of about 1 um to about 5 um, and most preferably about 2 um to about 3 um.

Formulations of at least one Anti-GD2 antibody composition protein suitable for use with a sprayer typically include antibody composition protein in an aqueous solution at a concentration of about 0.1 mg to about 100 mg of at least one Anti-GD2 antibody composition protein per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as GD2 antibodies, or specified portions, or variants, can also be included in the formulation.

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 um, preferably in the range of about 1 um to about 5 um, and most preferably about 2 um to about 3 um.

Formulations of at least one Anti-GD2 antibody suitable for use with a nebulizer, either jet or ultrasonic, typically include a concentration of about 0.1 mg to about 100 mg of at least one Anti-GD2 antibody protein per ml of solution. The formulation can include agents such as an excipient, a buffer, an isotonicity agent, a preservative, a surfactant, and, preferably, zinc. The formulation can also include an excipient or agent for stabilization of the at least one Anti-GD2 antibody composition protein, such as a buffer, a reducing agent, a bulk protein, or a carbohydrate. Bulk proteins useful in formulating at least one Anti-GD2 antibody composition proteins include albumin, protamine, or the like. Typical carbohydrates useful in formulating at least one Anti-GD2 antibody include sucrose, mannitol, lactose, trehalose, glucose, or the like. The at least one Anti-GD2 antibody formulation can also include a surfactant, which can reduce or prevent surface-induced aggregation of the at least one Anti-GD2 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

In a metered dose inhaler (MDI), a propellant, at least one Anti-GD2 antibody, and any excipients or other additives are contained in a canister as a mixture including a liquefied compressed gas. Actuation of the metering valve releases die mixture as an aerosol, preferably containing particles in the size range of less than about 10 um, preferably about 1 um to about 5 um, and most preferably about 2 um to about 3 um. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one Anti-GD2 antibody for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one Anti-GD2 antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one Anti-GD2 antibody compositions via devices not described herein.

Formulations for oral administration rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug deliver systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 are used to deliver biologically active agents orally are known in the art.

For absorption through mucosal surfaces, compositions and methods of administering at least one Anti-GD2 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

For transdermal administration, the at least one Anti-GD2 antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

It can be sometimes desirable to deliver the compounds of the present invention to the subject over prolonged periods of time, for example, for periods of one week to one year or more from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or disulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

EXAMPLES

The invention will be further illustrated by the following non-limiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Antibody Purification of Murine 3F8 and Fab Fragment Preparation

Murine anti-GD2 MoAb 3F8 (IgG3) was purified from concentrated hybridoma supernatant, as previously described (Cheung et al., 1985, Cancer Res 45, 2642-2649). Fab fragments of m3F8 were generated by papain digestion using a standard Fab preparation kit (Pierce Biotechnology, Rockford, Ill.).

Crystallization and Data Collection

The purified 3F8 Fab fragment was concentrated to 12 mg/ml in 20 mM HEPES pH 6.5 and was crystallized in a hanging drop by vapor diffusion at 16° C. against a reservoir containing Hampton Index reagent D7 containing 0.1M BIS-TRIS, pH 6.5, 25% PEG 3350 (Hampton Research, Aliso Viejo, Calif.). The droplet was formed by mixing 1 μl of protein solution and 1 μl of reservoir solution. The crystals were protected by cryoprotectant containing 25% glycerol, 0.1M BIS-TRIS, pH 6.5, 25% PEG 3350. Data was collected at the Argonne Advanced Photon Source beamline 24IDC. The crystals belonged to the space group C2 and diffracted to 1.65 Å resolution.

Structure Determination and Refinement

The Fab structure was solved by molecular replacement with search model PDB entry 2AJU using Phaser (CCP4 suite) (Mccoy, et al., 2007, j. Appl. Crystallogr 40, 658-674). The best molecular replacement model was refined using Refmac5 (Murshudov et al., 1997, Acta Crystallogr D 53, 240-255), manual fitting was performed with O (Bailey, S., 1994, Acta Crystallogr D 50, 760-763), adding solvent with Arp-Warp (Lamzin and Wildon, 1993, Acta Crystallogr D 49, 129-147). The final model contained two polypeptide chains of m3F8 Fab and 585 solvent molecules. The final model was deposited in the Protein Data Bank (access code 3VFG).

Molecular Docking Simulations and in Silico Mutagenesis

GLIDE docking was performed using Schrodinger Suite 2009 platform (Schrodinger, New York, N.Y.). OPLS force fields were used to parameterize the proteins and ligands. Top ligand poses were clustered within a root-mean-square deviation of 2.0 Å and scored by GlideScore. CDOCKER docking and interaction energy measurements were performed using Discovery Studio 3.0 (Accelrys, San Diego, Calif.). CHARMm force fields were used to parameterize the proteins and ligands. Top ligand poses were clustered within a root-mean-square deviation of 2.0 Å and scored by CDOCKER Interaction Energy. For all docking studies involving GD2, the ceramide tail was replaced by a methyl group (data not shown). Docking simulations were done under rigid-body conditions where ligand conformations were docked onto proteins/antibodies with rigid side chains. Final docked complexes were energy minimized with CHARMm using Smart Minimizer algorithm on Discovery Studio 3.0 (Accelrys, San Diego, Calif.). In silico mutagenesis was done by calculating the free energy of binding of the docked antibody:antigen model using CHARMm force fields and the Calculate Mutation Energy protocol on Discovery Studio 3.0 (Accelrys, San Diego, Calif.).

Image Rendering

Molecular structure images were rendered with Pymol (Schrödinger, New York, N.Y.) for docking studies, or with Discovery Studio 3.0 (Accelrys, San Diego, Calif.) for electrostatic potential surfaces.

Modeling of Exposed Hydrophobic Surface Area

The antigen binding site of MoAb 3F8 and MoAb 3F8 H:Gly54Ile was modeled on Discovery Studio 3.0 (Accelrys, San Diego, Calif.). Exposed hydrophobic surfaces were rendered using Spatial Aggregation Propensity algorithm developed by Chennamsetty et al. (Chennamsetty et al., 2009, Proc Natl Acad Sci USA 106, 11937-99842), where patches of effective dynamically exposed hydrophobicity on a protein surface is quantitated and colored in red.

Cell Culture

Human neuroblastoma cell line LAN-1 was provided by Dr. Robert Seeger (Children's Hospital of Los Angeles). Melanoma cell lines M14 and OCM-1 from Dr. David Cobrinik (Children's Hospital of Los Angeles). All cell lines were grown in F10 RPMI 1640 medium supplemented with 10% fetal bovine serum (Hyclone, South Logan, Utah), 2 mM glutamine, 100 U/ml penicillin, and 100 μg/ml streptomycin at 37° C. in a 5% CO2 incubator.

Construction of the hu3F8 and Variants

Humanized 3F8 genes were synthesized for CHO cells (Blue Heron Biotechnology or Genscript) as previously described (Cheung et al., 2012, Oncoimmunology 1, 477-486). Using the bluescript vector (Eureka, Calif.), these heavy and light chain genes of hu3F8 were transfected into DG44 cells and selected with G418 (InVitrogen, Calif.).

Purification of Antibodies

Hu3F8 and chimeric 3F8 producer lines were cultured in Opticho serum free medium (InVitrogen) and the mature supernatant harvested as previously described (Cheung et al., 2012, supra). Protein A affinity column was pre-equilibrated with 25 mM sodium citrate buffer with 0.15 M NaCl, pH 8.2. Bound hu3F8 was eluted with 0.1 M citric acid/sodium citrate buffer, pH 3.9 and alkalinized (1:10 v/v ratio) in 25 mM sodium citrate, pH 8.5. It was passed through a Sartobind-Q membrane and concentrated to 5-10 mg/ml in 25 mM sodium citrate, 0.15 M NaCl, pH 8.2.

Quantitation of GD2 Binding by ELISA and Flow Cytometry

ELISA was performed as previously described (Cheung et al., 2012, supra). Microtiter plates were coated with GD2 at 20 ng per well. 150 μl per well of 0.5% BSA in PBS (diluent) was added to each plate for at least 30 min at ambient temperature to block excess binding sites. 100 μl of standard and samples (diluted 2-fold) were added to each well and incubated for 2.5 h at 37° C. After washing the plates with PBS, 100 μL of goat anti human-IgG (H+L) (Jackson Research Laboratory) diluted at 1:3500 in diluent was added to each well and incubated for 1 h at 4° C. ELISA color reaction was developed with chromogen OPD (Sigma) with the substrate hydrogen peroxide for 30 min at ambient temperature in the dark. The reaction was stopped with 5N H2SO4 and the optical density (OD) read with ELISA plate reader MRX (Dynex) at 490 nm To measure the retention of binding of MoAbs to antigen containing cells, antibodies were incubated with melanoma M14 cells and successively washed off Cells were initially collected at 1×106 cells per round bottom tube, centrifuged and rinsed with PBS, and resuspended in 100 μL PBS per assay tube. Cells were incubated with MoAbs hu3F8 or hu3F8-Ile ((1 μg MoAb/1×106 cells) for 30 minutes at 4° C. Cells then underwent successive rounds of washing using 5 ml PBS with 3 mM EDTA, followed by pelleting, discarding of supernatant and resuspension. With each successive wash, samples were incubated with R-Phycoerythrin (R-PE) conjugated anti-human IgG, Fcγ fragment specific secondary antibody (Jackson ImmunoResearch) for 30 minutes at 4° C. in the dark, washed, and then analyzed by flow cytometry using a BD FACS Calibur instrument. Samples were prepared in triplicate.

Antibody-Dependent Cell-Mediated Cytotoxicity (ADCC) by 51 Chromium Release

ADCC assays were performed using NK-92MI cells stably transfected with the human CD16 Fc receptor as previously described (Cheung et al., 2012, supra). LAN1-1, M14, OCM-1, U2OS, CRL1427, NCI—H345 target cells were detached with 2 mM EDTA in Ca2+ Mg2+ free PBS and washed in F10, before radiolabeling with 51Cr for ADCC assays.

Statistical Analyses

Curve fitting and statistical analyses were performed using GraphPad Prism 5.0. Student's T-test was used for calculations of significance.

EXAMPLE 1

In Silico Scanning Mutagenesis of 3F8:GD2 Model

In silico scanning mutagenesis was performed by taking the 12 residues that directly interacted with GD2 in the docked 3F8:GD2 model (L:Tyr37, L:Lys55, L:Val99, L:Leu102, H:Gly40, H:Tyr31, H:Asn32, H:Asn34, H:Ser56, H:Ser58, H:Gly97, and H:Met98), and analyzing the effect of single point mutations to all possibilities at each site. The models were energy minimized using CHARMm forcefields then analyzed for changes in interaction energies (electrostatic, van der Waals, entropic). The top mutations are shown in Table 1. Only 4 mutations were found to increase the interaction energy of the bound complex by more than 1 kcal/mol (Table 1). Only one point mutation was predicted to have substantially higher interaction energy (H:Gly54Ile) by a weighted mutation energy of −8 kcal/mol. The majority of this increase in interaction energy was due an increase in van der Waals contact with the antigen. The effects of double point and triple point mutations involving the 12 interacting residues was also computed, but no additional combination of mutations was found to increase the interaction energy. Table 1 sets forth the results of in silico scanning mutagenesis of CDR residues that directly interact with docked GD2 antigen. Energies are shown in units of kcal/mol.

TABLE 1

| Residue | Mutation | VDW Term | Electrostatic Term | Entropy Term | Weighted Mutation Energy | Effect of Mutation |
|---|---|---|---|---|---|---|
| HC: GLY54 | ILE | −18.84 | 0.21 | 0.19 | −8.23 | stabilizing |
| HC: GLY103 | LEU | −5.39 | 0.23 | −0.07 | −2.38 | stabilizing |
| HC: GLY103 | TRP | −4.44 | 0.23 | −0.01 | −1.9 | stabilizing |
| HC: GLY55 | THR | −2.96 | 0.07 | −0.1 | −1.38 | stabilizing |

Analysis of Antigen Binding Site of 3F8 and 3F8-Ile (H:Gly54Ile)

The single point mutation derived from in silico scanning mutagenesis simulations (H:Gly54Ile, termed 3F8-Ile) was modeled into the antigen binding site of 3F8 (data not shown). Because of the hydrophobic nature of the H:Gly54Ile mutation, an analysis of the hydrophobicity of the antigen binding site was performed, using the Spatial Aggregation Propensity algorithm (ials and Methods), which provides a measure of the hydrophobic solvent exposed patches). MoAb 3F8 has a hydrophobic patch at the GD2 binding site that centers around H:Ile56 (data not shown). H:Ile56 protrudes out of the binding cavity and may help the antibody interact with the membrane surface that surrounds the GD2 head group. Substitution of H:Gly54 to Ile increases the exposed hydrophobic surface area of the antigen binding site and also increases the van der Waals contact with GD2 in the docked model (data not shown).

Binding and Tumor Cell Killing Properties of hu3F8 and hu3F8-Ile H:Gly54Ile

To test whether the H:Gly54Ile mutation increases affinity to GD2 and ADCC of tumor cells, the mutation was engineered into the recently described humanized 3F8 (hu3F8) (Cheung et al., 2012, supra). Hu3F8 is less immunogenic than murine 3F8, retains the structural features of murine 3F8 found in this investigation, and is currently in phase I clinical trials. Hu3F8 and hu3F8 H:Gly54Ile (hu3F8-Ile) were constructed, expressed, purified, and tested for GD2 binding and ADCC. ELISA assays on GD2 showed that hu3F8-Ile had a negligible increase in binding efficiency relative to hu3F8 (EC50 of GD2 binding: hu3F8 48±13 ng/mL, hu3F8-Ile 38±11 ng/mL) (data not shown). To test the avidity of these antibodies to bind to GD2 in its native environment on the surface of tumor cells, a wash experiment was carried out where antibodies bound to the surface of M14, a GD2(+) melanoma cell line, were subjected to consecutive washing cycles with PBS-EDTA (see Material and Methods). Hu3F8-Ile showed a greater ability to resist being washed off tumor cells (t½ of hu3F8-Ile=3 washes, t½ of hu3F8=2 washes) (data not shown). No other mutation was found to enhance antigen binding.

Hu3F8 and hu3F8-Ile were then assayed for their efficiency in mediating ADCC of neuroblastoma LAN-1 in the presence of natural killer cell line NK-92MI transfected with human CD16 Fc receptor (data not shown). Hu3F8-Ile showed consistently a ~9-fold increase in cytotoxicity potency compared to hu3F8 (IC50 cell killing: hu3F8 1.35±0.15 ng/mL, hu3F8-Ile 0.15±0.01 ng/mL). A 6-7 fold increase in ADCC potency against melanomas M14 and OCM-1 cells was also observed (IC50 cell killing of M14 cells: hu3F8 25±2.2 ng/mL, hu3F8-Ile 3.7±1.1 ng/mL; IC50 cell killing of OCM-1 cells: hu3F8 8.5±0.8 ng/mL, hu3F8-Ile 1.5±0.1 ng/mL). These increases in ADCC potency for hu3F8-Ile relative to hu3F8 were highly significant ($p<0.001$).

To further optimize the potential clinical efficacy of humanized 3F8, we employed high throughput in silico scanning mutagenesis on the key interacting residues in the 3F8:GD2 docked model. We identified a single point mutation (H:Gly54Ile) that showed a modest increase in binding affinity in GD2-ELISA assays and an increase in the ability of hu3F8-Ile to retain binding to GD2 on a cell surface. More strikingly, we showed that hu3F8 had a ~6-9 fold increase in ADCC of GD2-positive tumor cell lines, including neuroblastoma, melanoma, osteosarcoma, and small cell lung cancer. The nature of the H:Gly54Ile mutation increases the exposed hydrophobic surface area at the antigen binding site. Since GD2 is embedded into the membrane surface by a ceramide moiety, the addition of an Ile at the antigen-binding site may potentiate ADCC, by enhancing the ability of MoAb 3F8 to stay bound to the membrane surface, as observed in the cell washing experiments.

Carbohydrate antigens play an important role in several biological pathways. The development of antibodies to target carbohydrates is important for investigating bacteria, tumors, blood groups, cell-cell adhesion interactions; viral, hormone, and toxin receptors; and the glycosylation of recombinant proteins (Heimburg-Molinaro and Rittenhouse-Olson, 2009, Methods Mol. Biol. 534, 341-357). Because the immune response to saccharides is T-cell independent, antibodies generated towards carbohydrate antigens are often produced as low affinity IgM antibodies (Heimburg-Molinaro and Rittenhouse-Olson, 2009, supra). In order to generate higher affinity antibodies for therapeutic application as in the case for cancer immunotherapy, affinity maturation techniques often need to be employed to enhance therapeutic effect. Traditional methods of antibody affinity maturation such as yeast/phage/ribosomal display rely on error-prone PCR that may not provide the full range of diversity at each of the amino acids in the CDR of the antibody. In this investigation we show that in silico scanning mutagenesis could be employed even if a high-resolution co-complex structure is not available. We additionally demonstrate that a modest increase in affinity can enhance the functional properties of MoAb 3F8 for therapeutic targeting to the tumor antigen GD2. Although an enhancement of ADCC is expected to translate into improved efficacy, this will have to be proven in a future clinical trial in patients. The use of these in silico techniques may provide a valuable addition to traditional experimental methods in developing the next generation of MoAb for the diagnosis or the treatment of not just cancer, but other human disorders where carbohydrate epitopes are druggable targets.

Design of New Framework hu3F8 Ver5

The framework structure of hu3F8 V1 (WO 2011/160119, Cheung et al., 2012, supra) was optimized for reduced immunogenicity based on computational methods. First, the hu3F8V1 heavy chain and light chain sequences were compared to human germline sequences humIGHV199 and humIGKV025, respectively (EMBL database, www.vbase2.org). Molecular simulations using CHARMm (CHemistry at Harvard Molecular mechanics) force fields (Brooks et al., 2009, J. Comp. Chem. 30, 1545-1615) were run on each potential humanizing mutation based on the crystal structure of murine 3F8 (protein data bank ascension 3VFG, http://www.pdb.org), to determine if the mutation was structurally permissive. Additionally, MHC class II T-cell eptiopes in hu3F8 V1 were identified using NN-align method on the Immune Epitope Database (http://www.iedb.org/), and minimized based on structurally permissive mutations. Based on a computational model of GD2 docked to the 3F8 crystal structure (built using CDOCKER and Discovery Studio softwares, Accelrys, San Diega, Calif.), CDR residues that were not modeled to directly interact with the GD2 antigen were considered for humanization mutations.

Selection of hu3F8 Mutants from the Yeast Libraries

The methodology for generating and isolating higher affinity mutants was as described in references (Zhao et al., Mol. Cancer Ther. 2011, 10, 1677-1685). Before FACS selection, yeast cells (1×10⁹) were incubated with 10 µg-GD2-conjugated magnetic beads for 1 h at room temperature in PBSA buffer (0.1% BSA in PBS), followed by the separation with a magnetic stand. The isolated beads were washed for 3 times with PBSA buffer, put into 10 ml of SDCAA (synthetic dextrose casmino acids) media and grown overnight in a 30° C. shaker with 250 rpm. The yeast cells recovered from magnetic beads were induced in SG/RCAA (synthetic galactose raffinose casamino acids)

media for 18 h at 20° C. with 250 rpm shaking. Approximately 1×108 yeast cells were pelleted, washed twice with PBSA buffer and resuspended in 1 ml PBSA buffer with biotinylated GD2 and a 1:100 dilution of mouse anti-c-myc antibody (Invitrogen). After incubation, yeast cells were washed 3 times and then resuspended in 1 ml PBSA buffer. Both 1:100 dilution of R-phycoerythrin conjugated Streptavidin (Invitrogen) and Alexa Fluor 488 conjugated goat anti-mouse IgG antibody (Invitrogen) was added to yeast cells, incubated at 4° C. for 30 min, and washed 3 times with PBSA buffer again, and then resuspended in PBSA buffer for sorting. Sorting gates were determined to select only the population with higher antigen binding signals. Collected cells were grown overnight in SDCAA media at 30° C. and induced in SG/RCAA for the next round of sorting. For the next three selections, approximately 1-2×107 yeast cells were used for staining with biotinylated IGF-1, respectively. Yeast plasmids were isolated using Zymoprep yeast Plasmid Miniprep II Kit (Zymo Research) according to the manufacturer's instructions and used for templates of library construction. Plasmids from 4rd round were prepared, sequenced and characterized.

Expression of hu3F8 scFv and IgG1

ScFvs were expressed and purified as previously described (Zhao et al., 2011, supra). HB2151 cells were transformed with pComb3x plasmid containing scFv sequences. Single fresh colonies were inoculated into 2YT medium containing 100 μg/mL ampicillin and 0.2% glucose. The culture was induced by isopropyl-L-thio-h-D-galactopyranoside (final concentration 0.5 mM). After overnight growth at 30° C., the bacteria were centrifuged at 5,000×g for 15 min. Soluble scFv was released from periplasm by incubating at 30° C. for 30 minutes. The clear supernatant was recovered for the purification on Ni-NTA column. Recombinant scFvs have FLAG and His tags. IgGs were expressed in CHO suspension cells as previously described (Cheung et al., 2012, supra). Hu3F8 V5 IgGs were transiently expressed using HEK293 cells (Invitrogen Freestyle Expression system). IgGs were purified on protein G column.

ELISA

For cross-reactivity with other gangliosides. GD2, GD1a, GD1b and were coated on polyvinyl microtiter plates at 20 ng per well in 90% ethanol. Following air drying, wells were blocked with 0.5% BSA in PBS at 150 ul per well for 1 h at room temperature. Antibodies were added in triplicates at 1 mg/ml (100 ml per well) in 0.5% BSA. Following incubation for 1 h at room temperature and washing with PBS, HRP-goat anti-human IgG at 1:5000 dilution for IgG antibodies or HRP-goat anti-Flag IgG at 1:5000 dilution for scFv antibodies were added. After incubation for 1 h at 4° C. and further washing, color reaction was performed and OD was read using ELISA plate reader at 490 nm.

Affinity Determination by Surface Plasmon Resonance

Affinity was measured using a Biacore T100. In brief, gangliosides were directly immobilized onto the CM5 sensor chip via hydrophobic interaction. Reference surface was immobilized with GM1. Active surface was immobilized with GD2 and GM1 in 1:1 ratio or GD1b alone. Diluted mixture of GD2 and GM1 (50 ug/ml) or GD1b was injected (300 ul) at a flow rate of 15 ul/min over 20 min. Extensive washing was followed with 10 mM NaOH (typically five washes of 20 ul at a flow rate of 5 ul/min) until a stable baseline was obtained.

Complement Mediated Cytotoxicity (CMC) Assay

Antibodies were tested for their direct effect on tumor cell growth and survival in the absence of human serum or human effector cells. Tumor targets were dissociated with 2 mM EDTA or Trypsin-EDTA, washed and plated onto 96-well flat bottom plates in with human serum. After incubation for 24 h in a 5% CO2 incubator at 37° C., increasing concentrations of antibodies in F10 are added to each well. Control wells received F10 alone. After incubation for 4 h at 37° C. in 5% CO2, WST-8 reagent (Cayman Chemical Co.) was added to each well and incubated in the dark in a CO2 incubator at 37° C. for 2-6 h. OD was read at 450 nm and 690 nm using ELISA plate reader. WST-8 assay was validated using direct cell counting using Trypan Blue (Sigma) or Beckman Coulter Counter (Beckman Coulter).

Antibody-Dependent Cell-Mediated Cytotoxicity (ADCC) by 51 Chromium Release

Target cells were detached with 2 mM EDTA in Ca2+ Mg2+ free PBS and washed in F10. Antigen density was estimated using Quantum Simply Cellular anti-Mouse IgG beads according the manufacturer's instructions (Bangs Laboratories, Inc.). For cytotoxicity assays, 100 uCi of 51Cr was incubated with 106 target cells in a final volume of 250 ul and incubated for 1 h at 37° C. with gentle resuspension of pellet at 15 min intervals. Cells were then washed and resuspended in 250 μl F10 and incubated for 30 min at 37° C. After washing, cells were counted and viability determined with Trypan Blue and quickly plated onto 96 well U-bottom plates. Peripheral blood from normal volunteers was collected into heparinized tubes. Blood was mixed with 3% dextran/PBS and kept at room temperature for 20 min to sediment the red cells. White cells were then ficolled and separated into peripheral blood mononuclear cells (PBMC) for PBMC-ADCC. Cells were washed in F10, counted and viability determined PBMC-ADCC was done in the presence of 10 U/ml of IL-2. Antibodies were diluted in F10 from 1 μg/ml in 10-fold dilutions. Plates were incubated in a 37° C., 5% CO2 incubator for 4 h. Released 51Cr in the ADCC supernatant was collected for gamma counting. Total release was determined using 10% sodium dodecyl sulfate (SDS) and background spontaneous release was determined with F10 only without effectors. An effector:target (E:T) ratio of 50:1 was generally used. Similarly, ADCC assays were performed using NK-92MI cells stably transfected with the human CD16 or human CD32 Fc receptors. Unlike PBMC, no cytokines were needed in the assay. E:T ratio was kept at 20:1.

Immunohistochemistry (IHC)

Tumors and normal tissues were obtained at Memorial Sloan-Kettering Cancer Center with institutional review board approval. Five- to seven-micrometer sections of snap-frozen tissues were fixed in acetone for 30 min at −20° C. Endogenous biotin-binding activity was blocked by sequential treatment with avidin and biotin (Vector avidin-biotin blocking kit; Invitrogen) for 20 min each. Sections were incubated with 3 ug/ml scFv-Flag at room temperature for 1 h. Following washing, sections were incubated with HRP anti-Flag antibodies for 30 min at room temperature and subsequent incubation with 3,3-diaminobenzidine for 5 min. H&E staining was also performed.

EXAMPLE 2

Construction of hu3F8V5

Nine point mutations were made in hu3F8 V1 to make hu3F8 V5 (see Table 2) in an effort to reduce the potential immunogenicity. All nine mutations were found be structurally permissive to the computational model of 3F8 bound to its antigen GD2. All of the mutations involve changing murine residues left in the humanization on 3F8, to the human germline sequences. Five of the mutations (LC: K24R, LC:S56T, LC:V58I, HC:I20L, HC:M92V) involve framework residues. We additionally found 4 mutations in CDR H2 (HC: A62S, HC: F63V, HC: M64K, HC: S56G) that removed a strong T-cell epitope as identified by in silico methods. While it is uncommon for one skilled in the art of antibody humanization by grafting methods to change CDR residues, our computational model of 3F8 bound to GD2 allowed us engineer these additional humanizing mutations.

Affinity Maturation of hu3F8

To perform affinity maturation based on yeast display methods, we synthesized a novel biotinylated GD2 derivative to use for selection. We had previously been unsuccessful using a standard biotinylated GD2 antigen. Using a synthetic GD2-azido derivative (FIG. 2), we fused it to a PEG spacer (see Example 7 below). Using this novel GD2 analog, we selected 2 mutations from a random library of hu3F8 ScFvs displayed on the surface of yeast, which had enhanced binding to the synthetic GD2 analog. The first one was LC:D32H which is located on CDR L1, and the second one was LC:E1K, which is a framework residue.

Two mutations (LC: E1K and LC: D32H) were tested in recombinantly expressed hu3F8V1 ScFv and hu3F8V5 ScFv constructs and binding affinities for native GD2 were measured using Biacore analysis. Based on structural modeling, all hu3F8 scFv were made in the VL-VH format, because it allows for less restricted access to the antigen binding pocket. This is in contrast to most conventional ScFvs, which are constructed in the VH-VL format. Several variants were also tested in the full IgG1 format. Table 2 sets forth the design of hu3F8V5.

TABLE 2

| Mutation made in hu3F8V1 to hu3F8V5 | Location | Rationale |
|---|---|---|
| LC: K24R | Framework | Humanizing mutation |
| LC: S56T | Framework | Humanizing mutation |
| LC: V58I | Framework | Humanizing mutation, Stabilizes structure |
| HC: I20L | Framework | Humanizing mutation |
| HC: A62S | CDR H2 | Humanizing mutation, reduces T cell epitope |
| HC: F63V | CDR H2 | Humanizing mutation, reduces T cell epitope |
| HC: M64K | CDR H2 | Humanizing mutation, reduces T cell epitope |
| HC: S65G | CDR H2 | Humanizing mutation, reduces T cell epitope |
| HC: M92V | Framework | Humanizing mutation, Stabilizes structure |

EXAMPLE 3

Binding Affinities

The binding affinities of the hu3F8 variants tested in the ScFv format (see Table 3) show a number of interesting findings. First, hu3F8V5 which was only designed to be less immunogenic than hu3F8V1, had a slightly stronger binding affinity to GD2 than hu3F8V1. The two affinity maturation mutations (LC: E1K and LC:D32H) when separately expressed, show an enhancement of binding to GD2. When expressed together in either the hu3F8V1 or hu3F8V5 scFv formats, a more significant enhancement in binding affinity is observed (7-12 fold lower $K_D$). When the double mutation (LC:E1K+LC:D32H) is combined with HC:G54I (based on in silico modeling, reference original patent), the binding affinity is not as strong as the double mutation alone, but still higher affinity that hu3F8V1. hu3F8 G54I has been shown to have a 7-10 fold increase in ADCC for GD2 positive tumor cell lines.

The binding affinities for the hu3F8 variants in the full IgG1 format are shown in Table 4. Similar to the ScFv data, the double mutation LC:E1K+LC:D32H shows a greater affinity than the single mutation LC:D32H in both the hu3F8 V1 and hu3F8 V5 formats. The overall enhancement of the LC:E1K+LC:D32H double mutation versus the parental is 8-10 fold in both hu3F8 V1 and hu3F8 V5 formats. The contribution of the LC:E1K to the enhancement in binding is unexpected since it is not a canonical CDR residue. Direct comparison of the binding affinities of hu3F8 V1 with the hu3F8 V5 IgG constructs cannot be made since the hu3F8 V5 constructs were transiently expressed in HEK 293 cells and may have altered structural properties that may affect binding. Table 3 sets forth the binding affinities of hu3F8 scFvs to GD2 as measured by Biacore. Table 4 sets forth the binding affinities of hu3F8 IgGs to GD2 as measured by Biacore.

TABLE 3

| Antibody | $K_D$ (M) | nM |
|---|---|---|
| hu3F8V1 scFv | 3.05E−08 | 31 |
| hu3F8V5 scFv | 2.37E−08 | 24 |
| hu3F8V1 E1K scFv | 1.15E−08 | 12 |
| hu3F8V1 D32H scFv | 7.84E−09 | 8 |
| hu3F8V5 D32H scFv | 5.52E−09 | 6 |
| hu3F8V1 E1K D32H scFv | 3.71E−09 | 4 |
| hu3F8V5 E1K D32H scFv | 1.96E−09 | 2 |
| hu3F8V1 E1K D32H G54I scFv | 6.89E−09 | 7 |
| hu3F8V1 ScFv - huOKT3 ScFv bispecific | 8.86E−09 | 9 |

TABLE 4

| Antibody | $K_D$ (M) | nM |
|---|---|---|
| hu3F8V1 IgG | 2.983E−9 | 3 |
| hu3F8V1 D32H IgG | 4.965E−10 | 0.5 |
| hu3F8V1 E1K D32H IgG | 2.696E−10 | 0.3 |
| hu3F8V5 IgG* | 1.32E−08 | 13 |
| hu3F8V5 D32H IgG* | 2.36E−09 | 2.4 |
| hu3F8V5 E1K D32H IgG* | 8.57E−10 | 1.6 |

*transiently expressed in HEK293 cells, can display different glycosylation than when stably expressed in CHO cells

EXAMPLE 4

Cross-Reactivity with Other Gangliosides

In cross-reactivity studies (Table 5, and data not shown), all of the hu3F8 variants had comparable cross-reactivity with GD1b (a ganglioside also present on Neuroblastoma tumors cells), and no significant cross-reactivity to other gangliosides tested (GD1a, GD1b, GD3) which demonstrates that hu3F8 variants retain the same specificity of the parental hu3F8V1. Table 5 sets forth the binding affinities of hu3F8 IgGs to GD1b as measured by Biacore.

TABLE 5

| Antibody | $K_D$ (M) | nM |
|---|---|---|
| hu3F8 V1 IgG | 9.30E−08 | 93 |
| hu3F8 V1 D32H IgG | 8.74E−08 | 87 |
| hu3F8 V1 E1K D32H IgG | 8.36E−08 | 84 |

EXAMPLE 5

Antibody Potency in ADCC and CMC

Anti-GD2 IgG1 antibodies were compared in ADCC assays using PBMC (peripheral blood mononuclear cells) or NK92-CD16 (CD16 positive cultured NK cells) as effectors and neuroblastoma LAN-1 cells as targets (data not shown). ADCC potencies of these antibodies were computed as the ratio (EC50 for 3F8)/(EC50 for MoAb). Relative to the parental hu3F8 V1 IgG, hu3F8 V1 LC:D32H and hu 3F8 V1 LC:E1K+LC:D32H were ~20-fold stronger in PBMC-ADCC, and 7-fold stronger in NK92-CD16-ADCC (see Table 6). Table 6 sets forth a summary of ADCC assays using hu3F8V1 IgGs.

TABLE 6

| | PBMC | | | NK92-CD16 | |
|---|---|---|---|---|---|
| Antibody | $EC_{50}$ (µg/ml) | relative potency* | Antibody | $EC_{50}$ (µg/ml) | relative potency* |
| hu3F8 V1 | 0.00021 | 1.00 | hu3F8 V1 | 0.002 | 1.00 |
| hu3F8 V1 D32H | 0.00003 | 7.00 | hu3F8 V1 D32H | 0.0001 | 20.00 |
| hu3F8 V1 E1K D32H | 0.00003 | 7.00 | hu3F8 V1 E1K D32H | 0.0001 | 20.00 |

*hu3F8 V1 is used as reference

The same antibodies were tested for their ability to induce CMC using human sera as effectors and LAN-1 cells as targets. (Table 7 and data not shown). The hu3F8 V1 LC:D32H shows a small enhancement in CMC whereas the hu3F8 V1 LC:E1K+LC:D32H showed relatively the same amount of CMC as the parental hu3F8 V1. The relatively low complement activation was desirable since complement activation is believed to mediate the pain side-effect associated with anti-GD2 immunotherapy. Table 7 sets forth a summary of CMC assays with hu3F8V1 IgGs.

TABLE 7

| Antibody | $EC_{50}$ (µg/ml) | relative potency * |
|---|---|---|
| hu3F8 V1 | 0.03 | 1.00 |
| hu3F8 VI D32H1 | 0.011 | 2.73 |
| hu3F8 V1 E1K D32H | 0.029 | 1.03 |

* hu3F8V1 is used as reference

EXAMPLE 6

Immunohistochemistry on Normal Tissues and Tumors

ScFv versions of hu3F8 V1, hu3F8 V1 LC:D32H, and hu3F8 LC:E1K+LC:D32H were tested for tissue specificity by IHC on human Neuroblastoma, osteosarcoma, Rhabdomyosarcoma, Ewing's sarcoma, Desmoplastic small round cell tumors and normal human tissues (see FIG. 1). Twelve normal tissues were also tested (see Table 8). Frontal lobe, pons, cerebellum, and spinal cord all stained positive with both affinity-matured clones (hu3F8 V1 LC:D32H and hu3F8 LC:E1K+LC:D32H) but not parental clone (hu3F8 V1) as expected, because GD2 is known to be present on neuronal tissues. In looking at IHC of different tumor samples, the affinity-matured clones (hu3F8 V1 LC:D32H, and hu3F8 LC:E1K+LC:D32H) showed a higher level of staining on GD2 positive tumors relative to the parental antibody (hu3F8 V1). Table 8 sets forth the strength of tissue staining with hu3F8V1 scFvs.

TABLE 8

| Tissue | V1 | V1 D32H | V1 E1K D32H |
|---|---|---|---|
| Stage 4 NB | 4 | 4 | 4 |
| Ileum | 0 | 0 | 0 |
| Skeletal Muscle | 0 | 0 | 0 |
| Cerebellum | 0 | 1 | 1 |
| Frontal Lobe | 0 | 1 | 1 |
| Pons | 0 | 1 | 1 |
| Stomach | 0 | 0 | 0 |
| Spinal Cord | 0 | 1 | 1 |
| Lung | 0 | 0 | 0 |
| Spleen | 0 | 0 | 0 |
| Thyroid | 0 | 0 | 0 |
| Kidney | 0 | 0 | 0 |
| Testes | 0 | 0 | 0 | scFv concentration is 3 µg/ml; NB, neuroblastoma; the strength is defined as 0, 1 (weak, heterogeneous membrane staining), 2 (weak, homogeneous membrane staining), 3 (strong, heterogeneous membrane staining) and 4 (strong, homogeneous membrane staining).

EXAMPLE 7

GD2 Biotinylation

For the small scale of reaction, the 100 µg of GD2-azido and 50 µg of DBCO-PEG4-biotin (Click Chemistry Tools) in 25 µl of water reacted overnight at 4° C. with gently rotation. In the next day, the excess DBCO-PEG4-biotin was inactivated by adding 30 µg of azido-PEG-azido (Click Chemistry Tools) and incubated for 1 h at room temperature. The product was diluted to reach the concentration of 0.5 mg/ml and stored at −80° C.

FACS Analysis

The yeast cells displaying Hu3F8 scFvs were grown and induced as for FACS analysis. The yeast cells (1×106) were incubated with 2 µg/ml biotinylated GD2-azido-PEG4-biotin or GD2-biotin a 1:100 dilution of mouse anti-c-myc antibody for 30 min on icee in PBS/0.1% BSA buffer. After once washing, cells were incubated with a 1:50 dilution of R-phycoerythrin conjugated Streptavidin Alexa Fluor 488 conjugated goat anti-mouse antibody for 30 min on ice, then washed again and resuspended in 0.5 ml PBSA buffer. Analysis was performed using a BD Bioscience FACS.

Results

Yeast cells displayed Hu3F8 scFv with cmyc tag on the cell surface, which were used to bind GD2 biotin conjugates with or without a PEG spacer. In flow cytometric analysis, the expression and GD2 binding of Hu3F8 scFv were detected as X- and Y-axle, respectively. We found the existing of PEG4 spacer is necessary for the GD2 observation in flow cytometric analysis, by comparing with GD2 without spacer (data not shown). See FIG. 2 for Biotin-PEG-GD2 chemical structure.

EXAMPLE 8

Measurement of MoAb Dissociation Rates by Surface Plasmon Resonance

Dissociation rates of hu3F8 IgGs with affinity enhancing mutations were measured by surface plasmon resonance (Biacore T100) using a high density GD2 model.

Briefly, gangliosides were directly immobilized onto a CM5 sensor chip via hydrophobic interaction. Reference surface was immobilized with GM1. Active surface was immobilized with pure GD2. GD2 (50 µg/mL) was injected (300 µl) at a flow rate of 15 µl/min over 20 minutes. Extensive washing was followed with 10 mM NaOH (typically five washes of 20 µl at a flow rate of 5 µl/min) until a stable baseline was obtained. The results are shown in Table 9 and FIG. 3.

TABLE 9

| Antibody | $K_{off}(S^{-1})$ | Fold change relative to hu3F8V1 |
|---|---|---|
| hu3F8V1 D32H G54I | $2.9 \times 10^{-4}$ | −6.4 |
| hu3F8V1 E1K D32H | $5.1 \times 10^{-4}$ | −3.6 |
| hu3F8V1 D32H | $6.9 \times 10^{-4}$ | −2.7 |
| hu3F8V1 E1K D32H G54I | $8.8 \times 10^{-4}$ | −2.1 |
| hu3F8V1 | $18.5 \times 10^{-4}$ | 1 |

As shown in Table 9 and FIG. 3, hu3F8 double mutants (hu3F8V1 LC:D32H HC:G54I and hu3F8V1 LC:E1K LC:D32H) demonstrated the slowest dissociation rates, which were 3.6 to 6.4 fold slower than hu3F8V1. The single mutant (hu3F8 V1 LC:D32H) and triple mutant (hu3F8V1 LC:E1K LC:D32H HC:G54I) demonstrated a 2.7 fold and 2.1 fold slower slower dissociation rate, respectively.

Antibody Potency in ADCC with Additional Tumor Cell Lines

Anti-GD2 IgG1 antibodies were compared in ADCC assays with NK92-CD16 (CD16 positive cultured NK cells) as effectors and either neuroblastoma IMR-32 or melanoma M14 as targets (as described above). ADCC potencies were calculated as the ratio of hu3F8V1 $EC_{50}$/antibody $EC_{50}$. The results are shown in Table 10.

TABLE 10

| | Target: IMR-32 | | Target: M14 | |
|---|---|---|---|---|
| Antibody | $EC_{50}$ (µg/ml) | Relative Potency | $EC_{50}$ (µg/ml) | Relative Potency |
| hu3F8V1 E1K D32H | 0.0005 | 140.0 | 0.0001 | 25.0 |
| hu3F8V1 D32H G54I | 0.0007 | 100.0 | 0.00011 | 22.7 |
| hu3F8V1 D32H | 0.0028 | 25.0 | 0.0005 | 5.0 |
| hu3F8V1 E1K D32H G54I | 0.0045 | 15.6 | 0.0007 | 3.6 |
| hu3F8V1 | 0.07 | 1.0 | 0.0025 | 1.0 |

The results show that relative to the parental hu3F8 V1 IgG, the double mutants (hu3F8V1 LC:D32H HC:G54I and hu3F8V1 LC:E1K) demonstrated a 100 to 140 fold increase in ADCC of IMR-32 cells and 22 to 25 fold increase in ADCC of M14 cells. The single mutant (hu3F8V1 LC:D32H) demonstrated a 25-fold increase in ADCC of IMR-32 cells and 5-fold increase in ADCC of M14 cells. The triple mutant (hu3F8V1 LC:E1K LC:D32H HC:G54I) demonstrated a 15.6 fold increase in ADCC of IMR-32 cells and a 3.6 fold increase in ADCC of M14 cells.

What is claimed is:

1. A high affinity anti-GD2 antibody or antigen-binding fragment thereof whose structure is characterized by a feature which reduces immunogenicity and increases affinity to GD2 as compared with an appropriate reference anti-GD2 antibody,
wherein the antibody or antigen-binding fragment thereof comprises HCDR1, HCDR2, HCDR3, LCDR1, LCDR2, and LCDR3 sequences as set forth in any one of SEQ ID NOs: 11-16 and 19, 21-25, and
wherein the feature is selected from the group consisting of:
a light chain D32H mutation as numbered according to Kabat;
a light chain E1K mutation as numbered according to Kabat; and combinations thereof.

2. The high affinity anti-GD2 antibody of claim 1, said antibody comprising a light chain variable domain sequence as set forth in SEQ ID NO: 1, 2, 7 or 8.

3. The high affinity anti-GD2 antibody of claim 1, comprising a heavy chain G54I mutation as numbered according to Kabat.

4. The high affinity anti-GD2 antibody of claim 1, said antibody comprising a heavy chain variable domain sequence as set forth in SEQ ID NO: 4, 5, or 10.

5. The high affinity anti-GD2 antibody of claim 1, said antibody comprising a light chain variable domain sequence as set forth in SEQ ID NO: 3 or 9.

6. The high affinity anti-GD2 antibody of claim 1, said antibody comprising a light chain variable domain sequence as set forth in SEQ ID NO: 1, 2, 7 or 8, and a heavy chain variable domain sequence as set forth in SEQ ID NO: 4, 5, or 10.

7. The high affinity anti-GD2 antibody of claim 5 comprising a light chain variable domain sequence as set forth in SEQ ID NO: 3 or 9, and a heavy chain variable domain sequence as set forth in SEQ ID NO: 4 or 10.

8. The high affinity anti-GD2 antibody of claim 1, wherein the antibody is a single chain variable fragment (scFv).

9. The high affinity anti-GD2 antibody of claim 8, wherein the scFv comprises a sequence identified as SEQ ID NO: 11, 13, 19, or 22.

10. The high affinity anti-GD2 antibody of claim 8, wherein the scFv comprises a sequence identified as SEQ ID NO: 12, 14, 15, 21, 23 or 24.

11. The high affinity anti-GD2 antibody of claim 8, wherein the scFv-comprises a sequence identified as SEQ ID NO: 16 or 25.

12. A bispecific antibody comprising a first binding site comprising any one of the scFvs comprising a sequence identified as any one of SEQ ID NOs: 11-16 and 18-19, and 21-25, and a second binding site.

13. The bispecific antibody of claim 12 wherein the second binding site comprises a scFv for huOKT3 comprising a sequence identified as SEQ ID NO: 26 or 27.

14. The bispecific antibody of claim 12 wherein the second binding site comprises a scFv for C825 comprising a sequence identified as SEQ ID NO: 28.

15. A composition comprising the antibody or antigen-binding fragment thereof of claim 1.

16. The composition of claim 15, wherein the antibody is conjugated to a cytotoxic agent.

17. A pharmaceutical composition comprising the antibody or antigen-binding fragment thereof of the composition of claim 15, and further comprising a pharmaceutically acceptable carrier or diluent.

18. The bispecific antibody of claim 12 wherein the second antigen binding site is associated with an immunological cell chosen from the group consisting of T-lymphocytes NK cell, B-lymphocytes, dendritic cells, monocytes, macrophages, neutrophils, mesenchymal stem cells, neural stem cells.

19. The bispecific antibody of claim 12 wherein the second antigen binding site is specific for CD3.

20. The composition of claim 15, further comprising a molecule comprising azido-GD2-oligosaccharide reacted with biotin-PEG-Alkyne.

21. The bispecific antibody of claim 12 wherein the second antigen binding site binds to a hapten.

22. The bispecific antibody of claim 21 wherein the hapten is labeled with a diagnostic detection label.

23. The bispecific antibody of claim 12 wherein the second antigen binding site binds to a cytokine or cytostatic agent.

24. The high affinity anti-GD2 antibody or antigen-binding fragment thereof of claim 1, wherein the antibody is radioactively labeled.

25. A therapeutic composition comprising the high affinity anti-GD2antibody or antigen-binding fragment thereof of claim 24.

26. A diagnostic composition comprising the high affinity anti-GD2antibody or antigen-binding fragment thereof of claim 24.

* * * * *

UNITED STATES PATENT AND TRADEMARK OFFICE
CERTIFICATE OF CORRECTION

PATENT NO. : 10,167,341 B2
APPLICATION NO. : 14/776298
DATED : January 1, 2019
INVENTOR(S) : Nai-Kong V. Cheung, Mahiuddin Ahmed and Qi Zhao It is certified that error appears in the above-identified patent and that said Letters Patent is hereby corrected as shown below:

On the Title Page

Left column under "(71) Applicant:", please delete: "Memorial Sloan-Kettering Cancer Center" and insert -- "Memorial Sloan Kettering Cancer Center" -- therefor.

In the Claims

In Claim 25, at Column 149, Line 23: please delete: "anti-GD2antibody" and insert -- "anti-GD2 antibody" -- therefor.

In Claim 26, at Column 149, Line 26: please delete: "anti-GD2antibody" and insert -- "anti-GD2 antibody" -- therefor.

Signed and Sealed this
Nineteenth Day of March, 2019

Andrei Iancu
*Director of the United States Patent and Trademark Office*

SEQUENCE LISTING

```
<160> NUMBER OF SEQ ID NOS: 46

<210> SEQ ID NO 1
<211> LENGTH: 211
<212> TYPE: PRT
<213> ORGANISM: artificial sequence
<220> FEATURE:
<223> OTHER INFORMATION: synthetic

<400> SEQUENCE: 1

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190
```

Val Thr His Gln Gly Leu Ser Ser Pro Val Thr Lys Ser Phe Asn Arg
        195                 200                 205

Gly Glu Cys
    210

<210> SEQ ID NO 2
<211> LENGTH: 211
<212> TYPE: PRT
<213> ORGANISM: artificial sequence
<220> FEATURE:
<223> OTHER INFORMATION: synthetic

<400> SEQUENCE: 2

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 3
<211> LENGTH: 211
<212> TYPE: PRT
<213> ORGANISM: artificial sequence
<220> FEATURE:
<223> OTHER INFORMATION: synthetic

<400> SEQUENCE: 3

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
50                  55                  60

```
Ser Gly Tyr Gly Thr Glu Phe Thr Phe Thr Ile Ser Ser Val Gln Ser
 65                  70                  75                  80

Glu Asp Phe Ala Val Tyr Phe Cys Gln Gln Asp Tyr Ser Ser Phe Gly
                 85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210
```

<210> SEQ ID NO 4
<211> LENGTH: 449
<212> TYPE: PRT
<213> ORGANISM: artificial sequence
<220> FEATURE:
<223> OTHER INFORMATION: synthetic

<400> SEQUENCE: 4

```
Gln Val Gln Leu Val Glu Ser Gly Pro Gly Val Val Gln Pro Gly Arg
  1               5                  10                  15

Ser Leu Arg Ile Ser Cys Ala Val Ser Gly Phe Ser Val Thr Asn Tyr
                 20                  25                  30

Gly Val His Trp Val Arg Gln Pro Pro Gly Lys Gly Leu Glu Trp Leu
             35                  40                  45

Gly Val Ile Trp Ala Ile Gly Ile Thr Asn Tyr Asn Ser Ala Phe Met
     50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Met Tyr Tyr Cys Ala
                 85                  90                  95

Ser Arg Gly Gly His Tyr Gly Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 5
<211> LENGTH: 449
<212> TYPE: PRT
<213> ORGANISM: artificial sequence
<220> FEATURE:
<223> OTHER INFORMATION: synthetic

<400> SEQUENCE: 5

Gln Val Gln Leu Val Glu Ser Gly Pro Gly Val Val Gln Pro Gly Arg
1               5                   10                  15

Ser Leu Arg Leu Ser Cys Ala Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ser Val Lys
    50                  55                  60

Gly Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Arg Gly Gly His Tyr Gly Tyr Ala Leu Asp Tyr Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 6
<211> LENGTH: 211
<212> TYPE: PRT
<213> ORGANISM: artificial sequence
<220> FEATURE:
<223> OTHER INFORMATION: synthetic

<400> SEQUENCE: 6

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
```

```
                    20                  25                  30
Val Thr Trp Tyr Gln Gln Lys Pro Gly Gln Ala Pro Arg Leu Leu Ile
            35                  40                  45
Tyr Ser Ala Ser Asn Arg Tyr Thr Gly Ile Pro Ala Arg Phe Ser Gly
        50                  55                  60
Ser Gly Tyr Gly Thr Glu Phe Thr Phe Thr Ile Ser Ser Val Gln Ser
65                  70                  75                  80
Glu Asp Phe Ala Val Tyr Phe Cys Gln Gln Asp Tyr Ser Ser Phe Gly
                85                  90                  95
Gln Gly Thr Lys Leu Glu Ile Lys Arg Thr Val Ala Ala Pro Ser Val
            100                 105                 110
Phe Ile Phe Pro Pro Ser Asp Glu Gln Leu Lys Ser Gly Thr Ala Ser
        115                 120                 125
Val Val Cys Leu Leu Asn Asn Phe Tyr Pro Arg Glu Ala Lys Val Gln
    130                 135                 140
Trp Lys Val Asp Asn Ala Leu Gln Ser Gly Asn Ser Gln Glu Ser Val
145                 150                 155                 160
Thr Glu Gln Asp Ser Lys Asp Ser Thr Tyr Ser Leu Ser Ser Thr Leu
                165                 170                 175
Thr Leu Ser Lys Ala Asp Tyr Glu Lys His Lys Val Tyr Ala Cys Glu
            180                 185                 190
Val Thr His Gln Gly Leu Ser Ser Pro Val Thr Lys Ser Phe Asn Arg
        195                 200                 205
Gly Glu Cys
    210

<210> SEQ ID NO 7
<211> LENGTH: 211
<212> TYPE: PRT
<213> ORGANISM: artificial sequence
<220> FEATURE:
<223> OTHER INFORMATION: synthetic

<400> SEQUENCE: 7

Glu Ile Val Met Thr Gln Thr Pro Ala Thr Leu Ser Val Ser Ala Gly
1               5                   10                  15
Glu Arg Val Thr Ile Thr Cys Arg Ala Ser Gln Ser Val Ser Asn His
            20                  25                  30
Val Thr Trp Tyr Gln Gln Lys Pro Gly Gln Ala Pro Arg Leu Leu Ile
        35                  40                  45
Tyr Ser Ala Ser Asn Arg Tyr Thr Gly Ile Pro Ala Arg Phe Ser Gly
    50                  55                  60
Ser Gly Tyr Gly Thr Glu Phe Thr Phe Thr Ile Ser Ser Val Gln Ser
65                  70                  75                  80
Glu Asp Phe Ala Val Tyr Phe Cys Gln Gln Asp Tyr Ser Ser Phe Gly
                85                  90                  95
Gln Gly Thr Lys Leu Glu Ile Lys Arg Thr Val Ala Ala Pro Ser Val
            100                 105                 110
Phe Ile Phe Pro Pro Ser Asp Glu Gln Leu Lys Ser Gly Thr Ala Ser
        115                 120                 125
Val Val Cys Leu Leu Asn Asn Phe Tyr Pro Arg Glu Ala Lys Val Gln
    130                 135                 140
Trp Lys Val Asp Asn Ala Leu Gln Ser Gly Asn Ser Gln Glu Ser Val
145                 150                 155                 160
Thr Glu Gln Asp Ser Lys Asp Ser Thr Tyr Ser Leu Ser Ser Thr Leu
```

```
                    165                 170                 175
Thr Leu Ser Lys Ala Asp Tyr Glu Lys His Lys Val Tyr Ala Cys Glu
                180                 185                 190

Val Thr His Gln Gly Leu Ser Ser Pro Val Thr Lys Ser Phe Asn Arg
            195                 200                 205

Gly Glu Cys
    210

<210> SEQ ID NO 8
<211> LENGTH: 211
<212> TYPE: PRT
<213> ORGANISM: artificial sequence
<220> FEATURE:
<223> OTHER INFORMATION: synthetic

<400> SEQUENCE: 8

Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 9
<211> LENGTH: 211
<212> TYPE: PRT
<213> ORGANISM: artificial sequence
<220> FEATURE:
<223> OTHER INFORMATION: synthetic

<400> SEQUENCE: 9

Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
            20                  25                  30
```

Val Thr Trp Tyr Gln Gln Lys Pro Gly Gln Ala Pro Arg Leu Leu Ile
            35                  40                  45

Tyr Ser Ala Ser Asn Arg Tyr Thr Gly Ile Pro Ala Arg Phe Ser Gly
 50                  55                  60

Ser Gly Tyr Gly Thr Glu Phe Thr Phe Thr Ile Ser Ser Val Gln Ser
 65                  70                  75                  80

Glu Asp Phe Ala Val Tyr Phe Cys Gln Gln Asp Tyr Ser Ser Phe Gly
                 85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 10
<211> LENGTH: 449
<212> TYPE: PRT
<213> ORGANISM: artificial sequence
<220> FEATURE:
<223> OTHER INFORMATION: synthetic

<400> SEQUENCE: 10

Gln Val Gln Leu Val Glu Ser Gly Pro Gly Val Val Gln Pro Gly Arg
 1               5                  10                  15

Ser Leu Arg Leu Ser Cys Ala Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Ile Gly Ile Thr Asn Tyr Asn Ser Ser Val Lys
 50                  55                  60

Gly Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Ser Arg Gly Gly His Tyr Gly Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 11
<211> LENGTH: 239
<212> TYPE: PRT
<213> ORGANISM: artificial sequence
<220> FEATURE:
<223> OTHER INFORMATION: synthetic

<400> SEQUENCE: 11

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
                20                  25                  30

Val Thr Trp Tyr Gln Gln Lys Pro Gly Gln Ala Pro Arg Leu Leu Ile
            35                  40                  45

Tyr Ser Ala Ser Asn Arg Tyr Ser Gly Val Pro Ala Arg Phe Ser Gly
        50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly

```
                        85                  90                  95
Gln Gly Thr Lys Leu Glu Ile Lys Arg Gly Gly Gly Ser Gly Gly
            100                 105                 110

Gly Gly Ser Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
            165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
            195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser
225                 230                 235

<210> SEQ ID NO 12
<211> LENGTH: 239
<212> TYPE: PRT
<213> ORGANISM: artificial sequence
<220> FEATURE:
<223> OTHER INFORMATION: synthetic

<400> SEQUENCE: 12

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
            165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
            195                 200                 205

Asp Thr Ala Met Tyr Tyr Cys Ala Ser Arg Gly Gly His Tyr Gly Tyr
```

```
Ala Leu Asp Tyr Trp Gly Gln Gly Thr Leu Val Thr Val Ser Ser
225                 230                 235

<210> SEQ ID NO 13
<211> LENGTH: 239
<212> TYPE: PRT
<213> ORGANISM: artificial sequence
<220> FEATURE:
<223> OTHER INFORMATION: synthetic

<400> SEQUENCE: 13

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Gly Ser Gly Gly
            100                 105                 110

Gly Gly Ser Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
        130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser
225                 230                 235

<210> SEQ ID NO 14
<211> LENGTH: 239
<212> TYPE: PRT
<213> ORGANISM: artificial sequence
<220> FEATURE:
<223> OTHER INFORMATION: synthetic

<400> SEQUENCE: 14

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45
```

```
Tyr Ser Ala Ser Asn Arg Tyr Ser Gly Val Pro Ala Arg Phe Ser Gly
        50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
                100                 105                 110

Gly Gly Ser Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
        130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ala Phe Met Ser Arg Leu Thr Ile Ser Lys Asp
                180                 185                 190

Asn Ser Lys Asn Thr Val Tyr Leu Gln Met Asn Ser Leu Arg Ala Glu
            195                 200                 205

Asp Thr Ala Met Tyr Tyr Cys Ala Ser Arg Gly Gly His Tyr Gly Tyr
        210                 215                 220

Ala Leu Asp Tyr Trp Gly Gln Gly Thr Leu Val Thr Val Ser Ser
225                 230                 235

<210> SEQ ID NO 15
<211> LENGTH: 239
<212> TYPE: PRT
<213> ORGANISM: artificial sequence
<220> FEATURE:
<223> OTHER INFORMATION: synthetic

<400> SEQUENCE: 15

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
                20                  25                  30

Val Thr Trp Tyr Gln Gln Lys Pro Gly Gln Ala Pro Arg Leu Leu Ile
            35                  40                  45

Tyr Ser Ala Ser Asn Arg Tyr Ser Gly Val Pro Ala Arg Phe Ser Gly
        50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
                100                 105                 110

Gly Gly Ser Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
        130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175
```

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser
225                 230                 235

<210> SEQ ID NO 16
<211> LENGTH: 239
<212> TYPE: PRT
<213> ORGANISM: artificial sequence
<220> FEATURE:
<223> OTHER INFORMATION: synthetic

<400> SEQUENCE: 16

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser
225                 230                 235

<210> SEQ ID NO 17
<211> LENGTH: 239
<212> TYPE: PRT
<213> ORGANISM: artificial sequence
<220> FEATURE:
<223> OTHER INFORMATION: synthetic

<400> SEQUENCE: 17

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser
225                 230                 235

<210> SEQ ID NO 18
<211> LENGTH: 239
<212> TYPE: PRT
<213> ORGANISM: artificial sequence
<220> FEATURE:
<223> OTHER INFORMATION: synthetic

<400> SEQUENCE: 18

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Leu Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
            165                 170                 175

Thr Asn Tyr Asn Ser Val Lys Gly Arg Leu Thr Ile Ser Lys Asp
        180                 185                 190

Asn Ser Lys Asn Thr Val Tyr Leu Gln Met Asn Ser Leu Arg Ala Glu
        195                 200                 205

Asp Thr Ala Val Tyr Tyr Cys Ala Ser Arg Gly Gly His Tyr Gly Tyr
        210                 215                 220

Ala Leu Asp Tyr Trp Gly Gln Gly Thr Leu Val Thr Val Ser Ser
225                 230                 235

<210> SEQ ID NO 19
<211> LENGTH: 239
<212> TYPE: PRT
<213> ORGANISM: artificial sequence
<220> FEATURE:
<223> OTHER INFORMATION: synthetic

<400> SEQUENCE: 19

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Ser Gln Val Gln Leu Val Glu Ser Gly
        115                 120                 125

Pro Gly Val Val Gln Pro Gly Arg Ser Leu Arg Leu Ser Cys Ala Val
        130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
            165                 170                 175

Thr Asn Tyr Asn Ser Val Lys Gly Arg Leu Thr Ile Ser Lys Asp
        180                 185                 190

Asn Ser Lys Asn Thr Val Tyr Leu Gln Met Asn Ser Leu Arg Ala Glu
        195                 200                 205

Asp Thr Ala Val Tyr Tyr Cys Ala Ser Arg Gly Gly His Tyr Gly Tyr
        210                 215                 220

Ala Leu Asp Tyr Trp Gly Gln Gly Thr Leu Val Thr Val Ser Ser
225                 230                 235

<210> SEQ ID NO 20
<211> LENGTH: 239
<212> TYPE: PRT
<213> ORGANISM: artificial sequence
<220> FEATURE:
<223> OTHER INFORMATION: synthetic

<400> SEQUENCE: 20

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
            115                 120                 125

Pro Gly Val Val Gln Pro Gly Arg Ser Leu Arg Leu Ser Cys Ala Val
            130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
                165                 170                 175

Thr Asn Tyr Asn Ser Val Lys Gly Arg Leu Thr Ile Ser Lys Asp
                180                 185                 190

Asn Ser Lys Asn Thr Val Tyr Leu Gln Met Asn Ser Leu Arg Ala Glu
            195                 200                 205

Asp Thr Ala Val Tyr Tyr Cys Ala Ser Arg Gly Gly His Tyr Gly Tyr
            210                 215                 220

Ala Leu Asp Tyr Trp Gly Gln Gly Thr Leu Val Thr Val Ser Ser
225                 230                 235

<210> SEQ ID NO 21
<211> LENGTH: 239
<212> TYPE: PRT
<213> ORGANISM: artificial sequence
<220> FEATURE:
<223> OTHER INFORMATION: synthetic

<400> SEQUENCE: 21

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Gly Ser Gly Gly

Gly Gly Ser Gly Gly Gly Ser Gln Val Gln Leu Val Glu Ser Gly
            115                 120                 125
Pro Gly Val Val Gln Pro Gly Arg Ser Leu Arg Leu Ser Cys Ala Val
        130                 135                 140
Ser Gly Phe Ser Val Thr Asn Tyr Gly Val His Trp Val Arg Gln Pro
145                 150                 155                 160
Pro Gly Lys Gly Leu Glu Trp Leu Gly Val Ile Trp Ala Gly Ile
            165                 170                 175
Thr Asn Tyr Asn Ser Ser Val Lys Gly Arg Leu Thr Ile Ser Lys Asp
            180                 185                 190
Asn Ser Lys Asn Thr Val Tyr Leu Gln Met Asn Ser Leu Arg Ala Glu
            195                 200                 205
Asp Thr Ala Val Tyr Tyr Cys Ala Ser Arg Gly Gly His Tyr Gly Tyr
        210                 215                 220
Ala Leu Asp Tyr Trp Gly Gln Gly Thr Leu Val Thr Val Ser Ser
225                 230                 235

<210> SEQ ID NO 22
<211> LENGTH: 239
<212> TYPE: PRT
<213> ORGANISM: artificial sequence
<220> FEATURE:
<223> OTHER INFORMATION: synthetic

<400> SEQUENCE: 22

Lys Ile Val Met Thr Gln Thr Pro Ala Thr Leu Ser Val Ser Ala Gly
1               5                   10                  15
Glu Arg Val Thr Ile Thr Cys Arg Ala Ser Gln Ser Val Ser Asn Asp
            20                  25                  30
Val Thr Trp Tyr Gln Gln Lys Pro Gly Gln Ala Pro Arg Leu Leu Ile
        35                  40                  45
Tyr Ser Ala Ser Asn Arg Tyr Thr Gly Ile Pro Ala Arg Phe Ser Gly
    50                  55                  60
Ser Gly Tyr Gly Thr Glu Phe Thr Phe Thr Ile Ser Ser Val Gln Ser
65                  70                  75                  80
Glu Asp Phe Ala Val Tyr Phe Cys Gln Gln Asp Tyr Ser Ser Phe Gly
                85                  90                  95
Gln Gly Thr Lys Leu Glu Ile Lys Arg Gly Gly Gly Gly Ser Gly Gly
            100                 105                 110
Gly Gly Ser Gly Gly Gly Ser Gln Val Gln Leu Val Glu Ser Gly
            115                 120                 125
Pro Gly Val Val Gln Pro Gly Arg Ser Leu Arg Leu Ser Cys Ala Val
        130                 135                 140
Ser Gly Phe Ser Val Thr Asn Tyr Gly Val His Trp Val Arg Gln Pro
145                 150                 155                 160
Pro Gly Lys Gly Leu Glu Trp Leu Gly Val Ile Trp Ala Gly Ile
            165                 170                 175
Thr Asn Tyr Asn Ser Ser Val Lys Gly Arg Leu Thr Ile Ser Lys Asp
            180                 185                 190
Asn Ser Lys Asn Thr Val Tyr Leu Gln Met Asn Ser Leu Arg Ala Glu
            195                 200                 205
Asp Thr Ala Val Tyr Tyr Cys Ala Ser Arg Gly Gly His Tyr Gly Tyr
        210                 215                 220
Ala Leu Asp Tyr Trp Gly Gln Gly Thr Leu Val Thr Val Ser Ser

<210> SEQ ID NO 23
<211> LENGTH: 239
<212> TYPE: PRT
<213> ORGANISM: artificial sequence
<220> FEATURE:
<223> OTHER INFORMATION: synthetic

<400> SEQUENCE: 23

```
Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
            115                 120                 125

Pro Gly Val Val Gln Pro Gly Arg Ser Leu Arg Leu Ser Cys Ala Val
130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
                165                 170                 175

Thr Asn Tyr Asn Ser Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Val Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser
225                 230                 235
```

<210> SEQ ID NO 24
<211> LENGTH: 239
<212> TYPE: PRT
<213> ORGANISM: artificial sequence
<220> FEATURE:
<223> OTHER INFORMATION: synthetic

<400> SEQUENCE: 24

```
Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60
```

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
            115                 120                 125

Pro Gly Val Val Gln Pro Gly Arg Ser Leu Arg Leu Ser Cys Ala Val
            130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
            165                 170                 175

Thr Asn Tyr Asn Ser Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
            195                 200                 205

Asp Thr Ala Val Tyr Tyr Cys Ala Ser Arg Gly Gly His Tyr Gly Tyr
            210                 215                 220

Ala Leu Asp Tyr Trp Gly Gln Gly Thr Leu Val Thr Val Ser Ser
225                 230                 235

<210> SEQ ID NO 25
<211> LENGTH: 239
<212> TYPE: PRT
<213> ORGANISM: artificial sequence
<220> FEATURE:
<223> OTHER INFORMATION: synthetic

<400> SEQUENCE: 25

Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
                20                  25                  30

Val Thr Trp Tyr Gln Gln Lys Pro Gly Gln Ala Pro Arg Leu Leu Ile
            35                  40                  45

Tyr Ser Ala Ser Asn Arg Tyr Thr Gly Ile Pro Ala Arg Phe Ser Gly
        50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
            115                 120                 125

Pro Gly Val Val Gln Pro Gly Arg Ser Leu Arg Leu Ser Cys Ala Val
            130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
            165                 170                 175

Thr Asn Tyr Asn Ser Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
            195                 200                 205

Asp Thr Ala Val Tyr Tyr Cys Ala Ser Arg Gly Gly His Tyr Gly Tyr
210                 215                 220

Ala Leu Asp Tyr Trp Gly Gln Gly Thr Leu Val Thr Val Ser Ser
225                 230                 235

<210> SEQ ID NO 26
<211> LENGTH: 262
<212> TYPE: PRT
<213> ORGANISM: artificial sequence
<220> FEATURE:
<223> OTHER INFORMATION: synthetic

<400> SEQUENCE: 26

Ala Ser Thr Lys Gly Pro Gly Gly Gly Ser Gly Gly Gly Ser
1               5                   10                  15

Gly Gly Gly Gly Ser Gln Val Gln Leu Val Gln Ser Gly Gly Gly Val
            20                  25                  30

Val Gln Pro Gly Arg Ser Leu Arg Leu Ser Cys Lys Ala Ser Gly Tyr
        35                  40                  45

Thr Phe Thr Arg Tyr Thr Met His Trp Val Arg Gln Ala Pro Gly Lys
    50                  55                  60

Gly Leu Glu Trp Ile Gly Tyr Ile Asn Pro Ser Arg Gly Tyr Thr Asn
65                  70                  75                  80

Tyr Asn Gln Lys Phe Lys Asp Arg Phe Thr Ile Ser Arg Asp Asn Ser
                85                  90                  95

Lys Asn Thr Ala Phe Leu Gln Met Asp Ser Leu Arg Pro Glu Asp Thr
            100                 105                 110

Gly Val Tyr Phe Cys Ala Arg Tyr Tyr Asp Asp His Tyr Cys Leu Asp
        115                 120                 125

Tyr Trp Gly Gln Gly Thr Pro Val Thr Val Ser Ser Gly Gly Gly Gly
130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Ser Ala Ser Ser Ser Val Ser Tyr Met Asn Trp Tyr Gln Gln
            180                 185                 190

Thr Pro Gly Lys Ala Pro Lys Arg Trp Ile Tyr Asp Thr Ser Lys Leu
        195                 200                 205

Ala Ser Gly Val Pro Ser Arg Phe Ser Gly Ser Gly Ser Gly Thr Asp
    210                 215                 220

Tyr Thr Phe Thr Ile Ser Ser Leu Gln Pro Glu Asp Ile Ala Thr Tyr
225                 230                 235                 240

Tyr Cys Gln Gln Trp Ser Ser Asn Pro Phe Thr Phe Gly Gln Gly Thr
                245                 250                 255

Lys Leu Gln Ile Thr Arg
            260

<210> SEQ ID NO 27
<211> LENGTH: 256
<212> TYPE: PRT
<213> ORGANISM: artificial sequence
<220> FEATURE:
<223> OTHER INFORMATION: synthetic

<400> SEQUENCE: 27

Gly Gly Gly Gly Ser Gly Gly Gly Ser Gly Gly Gly Ser Gln
1               5                   10                  15

Val Gln Leu Val Gln Ser Gly Gly Val Val Gln Pro Gly Arg Ser
            20                  25                  30

Leu Arg Leu Ser Cys Lys Ala Ser Gly Tyr Thr Phe Thr Arg Tyr Thr
        35                  40                  45

Met His Trp Val Arg Gln Ala Pro Gly Lys Gly Leu Glu Trp Ile Gly
    50                  55                  60

Tyr Ile Asn Pro Ser Arg Gly Tyr Thr Asn Tyr Asn Gln Lys Phe Lys
65              70                  75                  80

Asp Arg Phe Thr Ile Ser Arg Asp Asn Ser Lys Asn Thr Ala Phe Leu
                85                  90                  95

Gln Met Asp Ser Leu Arg Pro Glu Asp Thr Gly Val Tyr Phe Cys Ala
                100                 105                 110

Arg Tyr Tyr Asp Asp His Tyr Cys Leu Asp Tyr Trp Gly Gln Gly Thr
        115                 120                 125

Pro Val Thr Val Ser Ser Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
                180                 185                 190

Lys Arg Trp Ile Tyr Asp Thr Ser Lys Leu Ala Ser Gly Val Pro Ser
                195                 200                 205

Arg Phe Ser Gly Ser Gly Ser Gly Thr Asp Tyr Thr Phe Thr Ile Ser
        210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Gln Ile Thr Arg
                245                 250                 255

<210> SEQ ID NO 28
<211> LENGTH: 244
<212> TYPE: PRT
<213> ORGANISM: artificial sequence
<220> FEATURE:
<223> OTHER INFORMATION: synthetic

<400> SEQUENCE: 28

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65              70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
                100                 105                 110

Thr Thr Val Thr Val Ser Ser Gly Gly Gly Ser Gly Gly Gly
            115                 120                 125

Ser Gly Gly Gly Ser Gln Ala Val Val Ile Gln Glu Ser Ala Leu
    130                 135                 140

Thr Thr Pro Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
                180                 185                 190

Gly Val Pro Ala Arg Phe Ser Gly Ser Leu Ile Gly Asp Lys Ala Ala
                195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Thr Arg Leu
225                 230                 235                 240

Thr Val Leu Gly

<210> SEQ ID NO 29
<211> LENGTH: 501
<212> TYPE: PRT
<213> ORGANISM: artificial sequence
<220> FEATURE:
<223> OTHER INFORMATION: synthetic

<400> SEQUENCE: 29

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

```
Ala Leu Asp Tyr Trp Gly Gln Gly Thr Leu Thr Val Ser Ser Ala
225                 230                 235                 240

Ser Thr Lys Gly Pro Gly Gly Gly Ser Gly Gly Gly Ser Gly
            245                 250                 255

Gly Gly Gly Ser Gln Val Gln Leu Val Gln Ser Gly Gly Val Val
                260                 265                 270

Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
        290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
        355                 360                 365

Trp Gly Gln Gly Thr Pro Val Thr Val Ser Ser Gly Gly Gly Gly Ser
        370                 375                 380

Gly Gly Gly Gly Ser Gly Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
        435                 440                 445

Ser Gly Val Pro Ser Arg Phe Ser Gly Ser Gly Ser Gly Thr Asp Tyr
        450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg
            500

<210> SEQ ID NO 30
<211> LENGTH: 495
<212> TYPE: PRT
<213> ORGANISM: artificial sequence
<220> FEATURE:
<223> OTHER INFORMATION: synthetic

<400> SEQUENCE: 30

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
                20                  25                  30

Val Thr Trp Tyr Gln Gln Lys Pro Gly Gln Ala Pro Arg Leu Leu Ile
            35                  40                  45

Tyr Ser Ala Ser Asn Arg Tyr Ser Gly Val Pro Ala Arg Phe Ser Gly
        50                  55                  60

Ser Gly Tyr Gly Thr Glu Phe Thr Phe Thr Ile Ser Ser Val Gln Ser
65                  70                  75                  80
```

```
Glu Asp Phe Ala Val Tyr Phe Cys Gln Gln Asp Tyr Ser Ser Phe Gly
                85                  90                  95
Gln Gly Thr Lys Leu Glu Ile Lys Arg Gly Gly Gly Ser Gly Gly
            100                 105                 110
Gly Gly Ser Gly Gly Gly Gly Ser Gln Val Gln Leu Val Glu Ser Gly
            115                 120                 125
Pro Gly Val Val Gln Pro Gly Arg Ser Leu Arg Ile Ser Cys Ala Val
            130                 135                 140
Ser Gly Phe Ser Val Thr Asn Tyr Gly Val His Trp Val Arg Gln Pro
145                 150                 155                 160
Pro Gly Lys Gly Leu Glu Trp Leu Gly Val Ile Trp Ala Gly Gly Ile
                165                 170                 175
Thr Asn Tyr Asn Ser Ala Phe Met Ser Arg Leu Thr Ile Ser Lys Asp
                180                 185                 190
Asn Ser Lys Asn Thr Val Tyr Leu Gln Met Asn Ser Leu Arg Ala Glu
            195                 200                 205
Asp Thr Ala Met Tyr Tyr Cys Ala Ser Arg Gly Gly His Tyr Gly Tyr
            210                 215                 220
Ala Leu Asp Tyr Trp Gly Gln Gly Thr Leu Val Thr Val Ser Ser Gly
225                 230                 235                 240
Gly Gly Gly Ser Gly Gly Gly Gly Ser Gly Gly Gly Gly Ser Gln Val
                245                 250                 255
Gln Leu Val Gln Ser Gly Gly Val Val Gln Pro Gly Arg Ser Leu
            260                 265                 270
Arg Leu Ser Cys Lys Ala Ser Gly Tyr Thr Phe Thr Arg Tyr Thr Met
            275                 280                 285
His Trp Val Arg Gln Ala Pro Gly Lys Gly Leu Glu Trp Ile Gly Tyr
            290                 295                 300
Ile Asn Pro Ser Arg Gly Tyr Thr Asn Tyr Asn Gln Lys Phe Lys Asp
305                 310                 315                 320
Arg Phe Thr Ile Ser Arg Asp Asn Ser Lys Asn Thr Ala Phe Leu Gln
                325                 330                 335
Met Asp Ser Leu Arg Pro Glu Asp Thr Gly Val Tyr Phe Cys Ala Arg
            340                 345                 350
Tyr Tyr Asp Asp His Tyr Cys Leu Asp Tyr Trp Gly Gln Gly Thr Pro
            355                 360                 365
Val Thr Val Ser Ser Gly Gly Gly Gly Ser Gly Gly Gly Gly Ser Gly
            370                 375                 380
Gly Gly Ser Asp Ile Gln Met Thr Gln Ser Pro Ser Ser Leu Ser
385                 390                 395                 400
Ala Ser Val Gly Asp Arg Val Thr Ile Thr Cys Ser Ala Ser Ser Ser
                405                 410                 415
Val Ser Tyr Met Asn Trp Tyr Gln Gln Thr Pro Gly Lys Ala Pro Lys
                420                 425                 430
Arg Trp Ile Tyr Asp Thr Ser Lys Leu Ala Ser Gly Val Pro Ser Arg
                435                 440                 445
Phe Ser Gly Ser Gly Ser Gly Thr Asp Tyr Thr Phe Thr Ile Ser Ser
            450                 455                 460
Leu Gln Pro Glu Asp Ile Ala Thr Tyr Tyr Cys Gln Gln Trp Ser Ser
465                 470                 475                 480
Asn Pro Phe Thr Phe Gly Gln Gly Thr Lys Leu Gln Ile Thr Arg
                485                 490                 495
```

```
<210> SEQ ID NO 31
<211> LENGTH: 498
<212> TYPE: PRT
<213> ORGANISM: artificial sequence
<220> FEATURE:
<223> OTHER INFORMATION: synthetic

<400> SEQUENCE: 31

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
210                 215                 220

Ala Leu Asp Tyr Trp Gly Gln Gly Thr Leu Val Thr Val Ser Ser Gly
225                 230                 235                 240

Gly Gly Gly Ser Gly Gly Gly Ser Gly Gly Gly Ser His Val
                245                 250                 255

Lys Leu Gln Glu Ser Gly Pro Gly Leu Val Gln Pro Ser Gln Ser Leu
            260                 265                 270

Ser Leu Thr Cys Thr Val Ser Gly Phe Ser Leu Thr Asp Tyr Gly Val
        275                 280                 285

His Trp Val Arg Gln Ser Pro Gly Lys Gly Leu Glu Trp Leu Gly Val
290                 295                 300

Ile Trp Ser Gly Gly Thr Ala Tyr Asn Thr Ala Leu Ile Ser Arg
305                 310                 315                 320

Leu Asn Ile Tyr Arg Asp Asn Ser Lys Asn Gln Val Phe Leu Glu Met
                325                 330                 335

Asn Ser Leu Gln Ala Glu Asp Thr Ala Met Tyr Tyr Cys Ala Arg Arg
            340                 345                 350

Gly Ser Tyr Pro Tyr Asn Tyr Phe Asp Ala Trp Gly Cys Gly Thr Thr
        355                 360                 365

Val Thr Val Ser Ser Gly Gly Gly Gly Ser Gly Gly Gly Gly Ser Gly
```

```
                370             375             380
Gly Gly Gly Ser Gln Ala Val Val Ile Gln Glu Ser Ala Leu Thr Thr
385             390                 395                 400

Pro Pro Gly Glu Thr Val Thr Leu Thr Cys Gly Ser Ser Thr Gly Ala
                405                 410                 415

Val Thr Ala Ser Asn Tyr Ala Asn Trp Val Gln Glu Lys Pro Asp His
                420                 425                 430

Cys Phe Thr Gly Leu Ile Gly Gly His Asn Asn Arg Pro Pro Gly Val
                435                 440                 445

Pro Ala Arg Phe Ser Gly Ser Leu Ile Gly Asp Lys Ala Ala Leu Thr
                450                 455                 460

Ile Ala Gly Thr Gln Thr Glu Asp Glu Ala Ile Tyr Phe Cys Ala Leu
465                 470                 475                 480

Trp Tyr Ser Asp His Trp Val Ile Gly Gly Gly Thr Arg Leu Thr Val
                485                 490                 495

Leu Gly
```

<210> SEQ ID NO 32
<211> LENGTH: 633
<212> TYPE: DNA
<213> ORGANISM: artificial sequence
<220> FEATURE:
<223> OTHER INFORMATION: synthetic

<400> SEQUENCE: 32

```
gaaatcgtca tgactcagac tcctgctact ctgtccgtct ccgctgggga aagggtcact   60
atcacttgta aggcatcaca gtccgtgagt aaccacgtga cttggtacca gcagaagcca  120
ggacaggcac ccaggctgct gatctactca gcctccaata gatatagcgg agtgccagca  180
cgcttcagcg gtctggtta tggcaccgag ttcacctta caatttccag cgtgcagtct  240
gaagacttcg ctgtctactt tgccagcag gattattcta gttttggaca ggggacaaag  300
ctggagatca aacgaaccgt ggccgccccc tccgtgttca tcttccccc ctccgacgag  360
cagctgaagt ccggcaccgc ctccgtggtg tgcctgctga caacttcta cccccgggag  420
gccaaggtgc agtggaaggt ggacaacgcc ctgcagtccg gcaactccca ggagtccgtg  480
accgagcagg actccaagga ctccacctac tccctgtcct ccaccctgac cctgtccaag  540
gccgactacg agaagcacaa ggtgtacgcc tgcgaggtga cccaccaggg cctgtcctcc  600
cccgtgacca gtccttcaa ccggggcgag tgc                                 633
```

<210> SEQ ID NO 33
<211> LENGTH: 633
<212> TYPE: DNA
<213> ORGANISM: artificial sequence
<220> FEATURE:
<223> OTHER INFORMATION: synthetic

<400> SEQUENCE: 33

```
aaaatcgtca tgactcagac tcctgctact ctgtccgtct ccgctgggga aagggtcact   60
atcacttgta aggcatcaca gtccgtgagt aaccacgtga cttggtacca gcagaagcca  120
ggacaggcac ccaggctgct gatctactca gcctccaata gatatagcgg agtgccagca  180
cgcttcagcg gtctggtta tggcaccgag ttcacctta caatttccag cgtgcagtct  240
gaagacttcg ctgtctactt tgccagcag gattattcta gttttggaca ggggacaaag  300
ctggagatca aacgaaccgt ggccgccccc tccgtgttca tcttccccc ctccgacgag  360
```

```
cagctgaagt ccggcaccgc ctccgtggtg tgcctgctga caacttcta ccccgggag      420 gccaaggtgc agtggaaggt ggacaacgcc ctgcagtccg gcaactccca ggagtccgtg      480
accgagcagg actccaagga ctccacctac tccctgtcct ccaccctgac cctgtccaag      540
gccgactacg agaagcacaa ggtgtacgcc tgcgaggtga cccaccaggg cctgtcctcc      600
cccgtgacca gtccttcaa ccggggcgag tgc                                   633
```

<210> SEQ ID NO 34
<211> LENGTH: 1347
<212> TYPE: DNA
<213> ORGANISM: artificial sequence
<220> FEATURE:
<223> OTHER INFORMATION: synthetic

<400> SEQUENCE: 34

```
caggtccagc tggtcgaatc tggtcctggg gtcgtgcagc ctggaggtc tctgcgtctg       60 agttgtgccg tgtccgggtt ttccgtgact aactacggag tgcactgggt cagacagcca     120
cctgggaagg gtctggagtg gctggagtg atctgggcag gcggaattac caactacaat     180
tccagcgtca aaggcaggct gaccatctct aaggacaaca gtaaaaatac agtgtatctg     240
cagatgaatt ccctgagggc cgaagataca gctgtctact attgcgcctc tcggggcggt     300
cattatggct acgcactgga ttactgggga cagggaactc tggtcaccgt ctcatcagcc     360
tccaccaagg gcccatcggt cttccccctg cacccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ccgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc cccatcccg ggatgagctg     1080 accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                         1347
```

<210> SEQ ID NO 35
<211> LENGTH: 633
<212> TYPE: DNA
<213> ORGANISM: artificial sequence
<220> FEATURE:
<223> OTHER INFORMATION: synthetic

<400> SEQUENCE: 35

```
gaaatcgtca tgactcagac tcctgctacc ctgtccgtgt cagctgggga gcgtgtcact       60
attacttgtc gggcttcaca gagcgtgtct aacgacgtga catggtacca gcagaagccc     120
```

```
ggtcaggccc ctagactgct gatctactct gctagtaata ggtatactgg cattccagca      180
cggttctcag gctccggata tgggaccgag ttcaccttta caatctccag cgtgcagagc      240
gaagactttg ccgtctattt ttgccagcag gattattcat cattcggcca gggaactaaa      300
ctggaaatca agagaaccgt ggccgccccc tccgtgttca tcttcccccc ctccgacgag      360
cagctgaagt ccggcaccgc ctccgtggtg tgcctgctga acaacttcta ccccgggag       420 gccaaggtgc agtggaaggt ggacaacgcc ctgcagtccg gcaactccca ggagtccgtg      480
accgagcagg actccaagga ctccacctac tccctgtcct ccaccctgac cctgtccaag      540
gccgactacg agaagcacaa ggtgtacgcc tgcgaggtga cccaccaggg cctgtcctcc      600
cccgtgacca agtccttcaa ccggggcgag tgc                                   633

<210> SEQ ID NO 36
<211> LENGTH: 633
<212> TYPE: DNA
<213> ORGANISM: artificial sequence
<220> FEATURE:
<223> OTHER INFORMATION: synthetic

<400> SEQUENCE: 36
gaaatcgtca tgactcagac tcctgctacc ctgtccgtgt cagctgggga gcgtgtcact      60
attacttgtc gggcttcaca gagcgtgtct aaccacgtga catggtacca gcagaagccc     120
ggtcaggccc ctagactgct gatctactct gctagtaata ggtatactgg cattccagca     180
cggttctcag gctccggata tgggaccgag ttcaccttta caatctccag cgtgcagagc     240
gaagactttg ccgtctattt ttgccagcag gattattcat cattcggcca gggaactaaa     300
ctggaaatca agagaaccgt ggccgccccc tccgtgttca tcttcccccc ctccgacgag     360
cagctgaagt ccggcaccgc ctccgtggtg tgcctgctga acaacttcta ccccgggag      420 gccaaggtgc agtggaaggt ggacaacgcc ctgcagtccg gcaactccca ggagtccgtg     480
accgagcagg actccaagga ctccacctac tccctgtcct ccaccctgac cctgtccaag     540
gccgactacg agaagcacaa ggtgtacgcc tgcgaggtga cccaccaggg cctgtcctcc     600
cccgtgacca agtccttcaa ccggggcgag tgc                                  633

<210> SEQ ID NO 37
<211> LENGTH: 633
<212> TYPE: DNA
<213> ORGANISM: artificial sequence
<220> FEATURE:
<223> OTHER INFORMATION: synthetic

<400> SEQUENCE: 37
aaaatcgtca tgactcagac tcctgctacc ctgtccgtgt cagctgggga gcgtgtcact      60
attacttgtc gggcttcaca gagcgtgtct aaccacgtga catggtacca gcagaagccc    120
ggtcaggccc ctagactgct gatctactct gctagtaata ggtatactgg cattccagca    180
cggttctcag gctccggata tgggaccgag ttcaccttta caatctccag cgtgcagagc    240
gaagactttg ccgtctattt ttgccagcag gattattcat cattcggcca gggaactaaa    300
ctggaaatca agagaaccgt ggccgccccc tccgtgttca tcttcccccc ctccgacgag    360
cagctgaagt ccggcaccgc ctccgtggtg tgcctgctga acaacttcta ccccgggag     420 gccaaggtgc agtggaaggt ggacaacgcc ctgcagtccg gcaactccca ggagtccgtg    480
accgagcagg actccaagga ctccacctac tccctgtcct ccaccctgac cctgtccaag    540
```

```
gccgactacg agaagcacaa ggtgtacgcc tgcgaggtga cccaccaggg cctgtcctcc    600
cccgtgacca gtccttcaa ccggggcgag tgc                                  633
```

<210> SEQ ID NO 38
<211> LENGTH: 1404
<212> TYPE: DNA
<213> ORGANISM: artificial sequence
<220> FEATURE:
<223> OTHER INFORMATION: synthetic

<400> SEQUENCE: 38

```
caggtccagc tggtcgaatc tggtcctggg gtcgtgcagc ctgggaggtc tctgcgtctg    60
agttgtgccg tgtccgggtt ttccgtgact aactacggag tgcactgggt cagacagcca    120
cctgggaagg gtctggagtg gctgggagtg atctgggcaa tcggaattac caactacaat    180
tccagcgtca aaggcaggct gaccatctct aaggacaaca gtaaaaatac agtgtatctg    240
cagatgaatt ccctgagggc cgaagataca gctgtctact attgcgcctc tcggggcggt    300
cattatggct acgcactgga ttactgggga caggaactc tggtcaccgt ctcatcacat     360
tatggctacg cactggatta ctggggacag ggaactctgg tcaccgtctc atcagcctcc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttccgcggcg tcctacagtc ctcaggactc    600
tactccctca gcagcgtggt gaccgtgccc tccagcagct gggcaccca gacctacatc     660 tgcaacgtga atcacaagcc cagcaacacc aaggtggaca gagagttga gcccaaatct     720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac    1020
aagtgcaagg tctccaacaa agccctccca gccccategg agaaaaccat ctccaaagcc    1080
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                            1404
```

<210> SEQ ID NO 39
<211> LENGTH: 717
<212> TYPE: DNA
<213> ORGANISM: artificial sequence
<220> FEATURE:
<223> OTHER INFORMATION: synthetic

<400> SEQUENCE: 39

```
gaaatcgtca tgactcagac tcctgctact ctgtccgtct ccgctgggga aagggtcact    60
atcacttgta aggcatcaca gtccgtgagt aaccacgtga cttggtacca gcagaagcca    120
ggacaggcac ccaggctgct gatctactca gcctccaata gatatagcgg agtgccagca    180
cgcttcagcg gtctggtta tggcaccgag ttcaccttta caatttccag cgtgcagtct    240
```

```
gaagacttcg ctgtctactt ttgccagcag gattattcta gttttggaca ggggacaaag    300
ctggagatca aacgaggagg aggaggtagc ggaggaggag gttctggcgg aggggggtagt    360 caggtgcagc tggtcgaatc cggtcctgga gtggtccagc caggcaggtc cctgcggatt    420
agctgtgcag tgagtggttt ctcagtcaca aactacggag tgcactgggt caggcagcca    480
cctggaaaag ggctggagtg gctgggagtg atctgggctg gcggaattac taactacaat    540
tccgccttca tgagtagact gactatctca aaggacaact ccaaaaatac cgtgtatctg    600
cagatgaatt cactgcgagc cgaagataca gctatgtact attgcgcttc ccgtggcggt    660
cattacggtt acgctctgga ttactggggt cagggaactc tggtcactgt ctcctcc       717

<210> SEQ ID NO 40
<211> LENGTH: 717
<212> TYPE: DNA
<213> ORGANISM: artificial sequence
<220> FEATURE:
<223> OTHER INFORMATION: synthetic

<400> SEQUENCE: 40
aaaatcgtca tgactcagac tcctgctact ctgtccgtct ccgctgggga aagggtcact     60
atcacttgta aggcatcaca gtccgtgagt aaccacgtga cttggtacca gcagaagcca    120
ggacaggcac ccaggctgct gatctactca gcctccaata gatatagcgg agtgccagca    180
cgcttcagcg ggtctggtta tggcaccgag ttcacctttta caatttccag cgtgcagtct    240
gaagacttcg ctgtctactt ttgccagcag gattattcta gttttggaca ggggacaaag    300
ctggagatca aacgaggagg aggaggtagc ggaggaggag gttctggcgg aggggggtagt    360 caggtgcagc tggtcgaatc cggtcctgga gtggtccagc caggcaggtc cctgcggatt    420
agctgtgcag tgagtggttt ctcagtcaca aactacggag tgcactgggt caggcagtca    480
cctggaaaag ggctggagtg gctgggagtg atctgggctg gcggaattac taactacaat    540
tccgccttca tgagtagact gactatctca aaggacaact ccaaaaatac cgtgtatctg    600
cagatgaatt cactgcgagc cgaagataca gctatgtact attgcgcttc ccgtggcggt    660
cattacggtt acgctctgga ttactggggt cagggaactc tggtcactgt ctcctcc       717

<210> SEQ ID NO 41
<211> LENGTH: 717
<212> TYPE: DNA
<213> ORGANISM: artificial sequence
<220> FEATURE:
<223> OTHER INFORMATION: synthetic

<400> SEQUENCE: 41
aaaatcgtca tgactcagac tcctgctact ctgtccgtct ccgctgggga aagggtcact     60
atcacttgta aggcatcaca gtccgtgagt aaccacgtga cttggtacca gcagaagcca    120
ggacaggcac ccaggctgct gatctactca gcctccaata gatatagcgg agtgccagca    180
cgcttcagcg ggtctggtta tggcaccgag ttcacctttta caatttccag cgtgcagtct    240
gaagacttcg ctgtctactt ttgccagcag gattattcta gttttggaca ggggacaaag    300
ctggagatca aacgaggagg aggaggtagc ggaggaggag gttctggcgg aggggggtagt    360 caggtgcagc tggtcgaatc cggtcctgga gtggtccagc caggcaggtc cctgcggatt    420
agctgtgcag tgagtggttt ctcagtcaca aactacggag tgcactgggt caggcagtca    480
cctggaaaag ggctggagtg gctgggagtg atctgggcta tcggaattac taactacaat    540
```

```
tccgccttca tgagtagact gactatctca aaggacaact ccaaaaatac cgtgtatctg    600
cagatgaatt cactgcgagc cgaagataca gctatgtact attgcgcttc ccgtggcggt    660
cattacggtt acgctctgga ttactgtgggt cagggaactc tggtcactgt ctcctcc     717
```

<210> SEQ ID NO 42
<211> LENGTH: 717
<212> TYPE: DNA
<213> ORGANISM: artificial sequence
<220> FEATURE:
<223> OTHER INFORMATION: synthetic

<400> SEQUENCE: 42

```
gaaatcgtca tgactcagac tcctgctacc ctgtccgtgt cagctgggga gcgtgtcact    60
attacttgtc gggcttcaca gagcgtgtct aacgacgtga catggtacca gcagaagccc    120
ggtcaggccc ctagactgct gatctactct gctagtaata ggtatactgg cattccagca    180
cggttctcag gctccggata tgggaccgag ttcaccttta caatctccag cgtgcagagc    240
gaagactttg ccgtctattt tgccagcag gattattcat cattcggcca gggaactaaa    300
ctggaaatca agagaggagg aggaggtagc ggaggaggag gttctggcgg aggggtagt     360 caggtccagc tggtcgaatc tggtcctggg gtcgtgcagc ctgggaggtc tctgcgtctg    420
agttgtgccg tgtccgggtt ttccgtgact aactacggag tgcactgggt cagacagcca    480
cctgggaagg gtctggagtg gctgggagtg atctgggcag gcggaattac caactacaat    540
tccagcgtca aaggcaggct gaccatctct aaggacaaca gtaaaaatac agtgtatctg    600
cagatgaatt ccctgagggc cgaagataca gctgtctact attgcgcctc tcggggcggt    660
cattatggct acgcactgga ttactgggga cagggaactc tggtcaccgt ctcatca      717
```

<210> SEQ ID NO 43
<211> LENGTH: 717
<212> TYPE: DNA
<213> ORGANISM: artificial sequence
<220> FEATURE:
<223> OTHER INFORMATION: synthetic

<400> SEQUENCE: 43

```
gaaatcgtca tgactcagac tcctgctacc ctgtccgtgt cagctgggga gcgtgtcact    60
attacttgtc gggcttcaca gagcgtgtct aaccacgtga catggtacca gcagaagccc    120
ggtcaggccc ctagactgct gatctactct gctagtaata ggtatactgg cattccagca    180
cggttctcag gctccggata tgggaccgag ttcaccttta caatctccag cgtgcagagc    240
gaagactttg ccgtctattt tgccagcag gattattcat cattcggcca gggaactaaa    300
ctggaaatca agagaggagg aggaggtagc ggaggaggag gttctggcgg aggggtagt     360 caggtccagc tggtcgaatc tggtcctggg gtcgtgcagc ctgggaggtc tctgcgtctg    420
agttgtgccg tgtccgggtt ttccgtgact aactacggag tgcactgggt cagacagcca    480
cctgggaagg gtctggagtg gctgggagtg atctgggcag gcggaattac caactacaat    540
tccagcgtca aaggcaggct gaccatctct aaggacaaca gtaaaaatac agtgtatctg    600
cagatgaatt ccctgagggc cgaagataca gctgtctact attgcgcctc tcggggcggt    660
cattatggct acgcactgga ttactgggga cagggaactc tggtcaccgt ctcatca      717
```

<210> SEQ ID NO 44
<211> LENGTH: 717
<212> TYPE: DNA
<213> ORGANISM: artificial sequence
<220> FEATURE:
<223> OTHER INFORMATION: synthetic

<400> SEQUENCE: 44

```
aaaatcgtca tgactcagac tcctgctacc ctgtccgtgt cagctgggga gcgtgtcact    60
attacttgtc gggcttcaca gagcgtgtct aaccacgtga catggtacca gcagaagccc   120
ggtcaggccc ctagactgct gatctactct gctagtaata ggtatactgg cattccagca   180
cggttctcag gctccggata tgggaccgag ttcacctta caatctccag cgtgcagagc    240
gaagactttg ccgtctattt ttgccagcag gattattcat cattcggcca gggaactaaa   300
ctggaaatca gagaggagg aggagtagc ggaggaggag gttctggcgg aggggtagt      360
caggtccagc tggtcgaatc tggtcctggg gtcgtgcagc ctgggaggtc tctgcgtctg   420
agttgtgccg tgtccgggtt ttccgtgact aactacggag tgcactgggt cagacagcca   480
cctgggaagg gtctggagtg gctgggagtg atctgggcag gcggaattac caactacaat   540
tccagcgtca aaggcaggct gaccatctct aaggacaaca gtaaaaatac agtgtatctg   600
cagatgaatt ccctgagggc cgaagataca gctgtctact attgcgcctc tcggggcggt   660
cattatggct acgcactgga ttactgggga caggaactc tggtcaccgt ctcatca      717
```

<210> SEQ ID NO 45
<211> LENGTH: 717
<212> TYPE: DNA
<213> ORGANISM: artificial sequence
<220> FEATURE:
<223> OTHER INFORMATION: synthetic

<400> SEQUENCE: 45

```
aaaatcgtca tgactcagac tcctgctacc ctgtccgtgt cagctgggga gcgtgtcact    60
attacttgtc gggcttcaca gagcgtgtct aaccacgtga catggtacca gcagaagccc   120
ggtcaggccc ctagactgct gatctactct gctagtaata ggtatactgg cattccagca   180
cggttctcag gctccggata tgggaccgag ttcacctta caatctccag cgtgcagagc    240
gaagactttg ccgtctattt ttgccagcag gattattcat cattcggcca gggaactaaa   300
ctggaaatca gagaggagg aggagtagc ggaggaggag gttctggcgg aggggtagt      360
caggtccagc tggtcgaatc tggtcctggg gtcgtgcagc ctgggaggtc tctgcgtctg   420
agttgtgccg tgtccgggtt ttccgtgact aactacggag tgcactgggt cagacagcca   480
cctgggaagg gtctggagtg gctgggagtg atctgggcaa tcggaattac caactacaat   540
tccagcgtca aaggcaggct gaccatctct aaggacaaca gtaaaaatac agtgtatctg   600
cagatgaatt ccctgagggc cgaagataca gctgtctact attgcgcctc tcggggcggt   660
cattatggct acgcactgga ttactgggga caggaactc tggtcaccgt ctcatca      717
```

<210> SEQ ID NO 46
<211> LENGTH: 239
<212> TYPE: PRT
<213> ORGANISM: artificial sequence
<220> FEATURE:
<223> OTHER INFORMATION: synthetic

<400> SEQUENCE: 46

```
Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30
```

-continued

```
Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
 50                  55                  60

Ser Gly Tyr Gly Thr Glu Phe Thr Phe Thr Ile Ser Ser Val Gln Ser
 65                  70                  75                  80

Glu Asp Phe Ala Val Tyr Phe Cys Gln Gln Asp Tyr Ser Ser Phe Gly
                 85                  90                  95

Cys Gly Thr Lys Leu Glu Ile Lys Arg Gly Gly Gly Ser Gly Gly
             100                 105                 110

Gly Gly Ser Gly Gly Gly Ser Gln Val Gln Leu Val Glu Ser Gly
             115                 120                 125

Pro Gly Val Val Gln Pro Gly Arg Ser Leu Arg Ile Ser Cys Ala Val
             130                 135                 140

Ser Gly Phe Ser Val Thr Asn Tyr Gly Val His Trp Val Arg Gln Pro
145                 150                 155                 160

Pro Gly Lys Cys Leu Glu Trp Leu Gly Val Ile Trp Ala Gly Gly Ile
             165                 170                 175

Thr Asn Tyr Asn Ser Ala Phe Met Ser Arg Leu Thr Ile Ser Lys Asp
             180                 185                 190

Asn Ser Lys Asn Thr Val Tyr Leu Gln Met Asn Ser Leu Arg Ala Glu
             195                 200                 205

Asp Thr Ala Met Tyr Tyr Cys Ala Ser Arg Gly Gly His Tyr Gly Tyr
             210                 215                 220

Ala Leu Asp Tyr Trp Gly Gln Gly Thr Leu Val Thr Val Ser Ser
225                 230                 235
```